(12) United States Patent
Tsou et al.

(10) Patent No.: US 6,608,048 B2
(45) Date of Patent: Aug. 19, 2003

(54) TRICYCLIC PROTEIN KINASE INHIBITORS

(75) Inventors: Hwei-Ru Tsou, New City, NY (US); Elsebe Geraldine Overbeek-Klumpers, Bergentheim (NL); Allan Wissner, Ardsley, NY (US)

(73) Assignee: Wyeth Holdings, Madison, NJ (US)

( * ) Notice: Subject to any disclaimer, the term of this patent is extended or adjusted under 35 U.S.C. 154(b) by 0 days.

(21) Appl. No.: 09/820,132

(22) Filed: Mar. 28, 2001

(65) Prior Publication Data

US 2003/0065180 A1 Apr. 3, 2003

Related U.S. Application Data

(60) Provisional application No. 60/304,206, filed on Mar. 28, 2000.

(51) Int. Cl.[7] .................. C07D 498/04; C07D 513/04; A61K 31/542; A61K 31/5365; A61P 35/00
(52) U.S. Cl. .................. 514/183; 514/211.15; 514/218; 514/224.5; 514/229; 540/467; 540/470; 540/544; 540/553; 540/575; 544/34; 544/60; 544/73; 544/101
(58) Field of Search ............................ 514/183, 211.15, 514/218, 224.5, 229.1; 540/467, 470, 544, 553, 575; 544/34, 60, 73, 101

(56) References Cited

U.S. PATENT DOCUMENTS

| | | | |
|---|---|---|---|
| 5,480,883 A | 1/1996 | Spada et al. ................ 514/249 |
| 5,780,482 A | 7/1998 | Armitage et al. ........... 514/300 |
| 6,002,008 A | 12/1999 | Wissner et al. ............. 546/160 |

FOREIGN PATENT DOCUMENTS

| | | |
|---|---|---|
| EP | 456 442 A1 | 11/1991 |
| EP | 0 412 848 B1 | 1/1995 |
| FR | 2 712 290 A | 5/1995 |
| WO | 92/02508 | 2/1992 |
| WO | WO 95/00511 | 1/1995 |
| WO | 96/09294 | 3/1996 |
| WO | 98/13350 | 4/1998 |
| WO | 98/43960 | 10/1998 |

OTHER PUBLICATIONS

PCT International Search Jul. 25, 2001.
English Abstracts of FR 2 712 290 A (listed in AR).
Ellis, L.M., J. Biol. Chem., 273, 1052 (1998).
Schwarzberg, P.L., Oncogene, 17, 1463–1468 (1998).
Campbell, S.L., Oncogene, 17, 1395–1413 (1998).
Tilton, R.G. et al., J. Clin. Invest., 99, 2192–2202 (1997).
Jackson, J.R. et al., FASEB J., 11, 457–465 (1997).
Staley et al., Cell Growth & Differentiation, 8, 269–74, (1997).
Sivaraman, V.S.; Wang, H.–Y.; Nuovo, G.J.; Malbon, C.C., J. Clin. Invest. 99, 1478 (1997).
Braunwalder, A.F., Yarwood, D.R., Sills, M.A., and Lipson, K.E., Anal. Biochem. 238, 159–164 (1996).
Gazit A., et al., J. Med. Chem., 39(11), 2170 (1996).
Borgstrom, P. et al., Cancer Res., 56, 4032–4039 (1996).
Kaji, M., et al. Cancer Gene Therapy, 3, 393–404 (1996).
Jeffers, M., et al. J. of Molecular Medicine 74, 505 (1996).
Aiello, L.P. et al., Proc. Nat. Acad. Sci., 92, 10457–10461 (1995).
Folkman, J., Nature Medicine, 1, 27–31 (1995).
Toi, M. et al., Breast Cancer Res. and Treat., 36, 192–204 (1995).
Dudley, D.T. et al.Proc. Nat. Acad. Sci., 92, 7686 (1995).
Seger, R.; Krebs, E.G., FASEB, 9, 726 (1995).
Gattone, V.H., Developmental Biology, 169(2), 504 (1995).
Nauta, J., Pediatric res., 37 (6), 755–763 (1995).
Du, J., Amer. J. Physiol., 269 (2 Pt 1), 487–495 (1995).
Dolle, R.E., et al., J. Med. Chem., 37(17) 2627 (1994).
Kim, J.K. et al., Nature, 362, 841–844 (1993).
Wilson, P.D., Eur. J. Cell Biol., 61(1), 131 (1993).
Wilks, A.F., Adv. Cancer Res., 60, 43–73 (1993).
Parsons, J.T. et al., Important Advances in Onclogy, DeVita, V.T. Ed., J.B. Lippincott Co.,Phila., 3(1993).
Ife, R.J., et al., J. Med. Chem., 35(18), 3413 (1992).
Gullick, W.J., Brit. Med. Bull., 47, 87 (1991).
Reiss, M., Cancer Res., 51, 6254–6262 (1991).
Philip Skehan et al., J. Natl. Canc. Inst., 82, 1107–1112 (1990).
Slamon, D.J., Science, 244, 707–712 (1989).
Macias, A., Anticancer Res., 7, 459–464 (1987).
Science, 235, 177–82 (1987).
Garcia–Echeverria, C., et al., Med. Res. Rev. 20, 28–57 (2000).
Bridges, A.J., Current Medicinal Chemistry, 6, 825–843 (1999).
Loganzo, F., Hardy, C., American Biotechnology Laboratory 16(13), 26–28 (1998).

*Primary Examiner*—Richard L. Raymond
*Assistant Examiner*—Thomas McKenzie
(74) *Attorney, Agent, or Firm*—Joy S. Goudie

(57) ABSTRACT

This invention provides compounds of Formula (I),

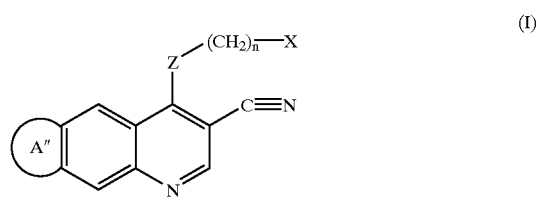

where A″, Z, X and n are defined herein, or a pharmaceutically acceptable salt thereof which are useful as antineoplastic agents and in the treatment of polycystic kidney disease.

51 Claims, No Drawings

TRICYCLIC PROTEIN KINASE INHIBITORS

CROSS REFERENCE TO RELATED APPLICATIONS

This application claims benefit of U.S. Provisional Application No. 60/304,206 which was converted from U.S. patent application Ser. No. 09/536,919 filed Mar. 28, 2000 pursuant to a petition filed under 37 C.F.R. 1.53 (c) (2) filed Jul. 11, 2000.

BACKGROUND OF THE INVENTION

1. Field of the Invention

This invention relates to certain substituted fused tricyclic compounds containing quinolinonitrile rings as well as the pharmaceutically acceptable salts thereof. The compounds of the present invention inhibit the action of certain growth factor receptor protein tyrosine kinases (PTK) and other protein kinases thereby inhibiting the abnormal growth of certain cell types. The compounds of this invention are therefore useful for the treatment of certain diseases that are the result of deregulation of these PTKs. The compounds of this invention are anti-cancer agents and are useful for the treatment of cancer in mammals. In addition, the compounds of this invention are useful for the treatment or inhibition of polycystic kidney disease and colonic polyps in mammals. This invention also relates to the manufacture of said substituted fused tricyclic compounds, their use for the treatment of cancer and polycystic kidney disease, and the pharmaceutical preparations containing them.

2. Description of the Prior Art

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of this is uncontrolled cell proliferation which can lead ti tumor growth and ultimately to the disease known as cancer [Wilks, A. F., *Adv. Cancer Res.*, 60, 43 (1993) and Parsons, J. T.; Parsons, S. J., *Important Advances in Oncology*, DeVita, V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., *Science*, 244, 707 (1989) and *Science*, 235, 1146 (1987)]. Deregulation of EGF-R kinase has been associated with epidermoid tumors [Reiss, M., et. al., *Cancer Res.*, 51, 6254 (1991)], breast tumors [Macias, A., et. al., *Anticancer Res.*, 7, 459 (1987)], and tumors involving other major organs [Gullick, W. J., *Brit. Med. Bull.*, 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Garcia-Echeverria, C., et al. *Med. Res. Rev.* 20, 28–57 (2000) and Bridges, A. J. *Current Medicinal Chemistry*, 6, 825–843 (1999)]. The compounds of this invention inhibit the kinase activity of EGF-R and are therefore useful for treating certain disease states, such as cancer, that result, at least in part, from deregulation of this receptor. The compounds of this invention are also useful for the treatment and prevention of certain pre-cancerous conditions, such as the growth of colon polyps, that result, at least in part, from deregulation of this receptor.

It is also known that deregulation of EGF receptors is a factor in the growth of epithelial cysts in the disease described as polycystic kidney disease [Du, J.; Wilson, P. D., *Amer. J. Phlysiol.*, 269(2 Pt 1), 487 (1995); Nauta, J., et al., *Pediatric Research*, 37(6), 755 (1995); Gattone, V. H., et al., *Developmental Biology*, 169(2), 504 (1995); Wilson, P. D., et al., *Eur. J. Cell Biol.*, 61(1), 131, (1993)]. The compounds of this invention, which inhibit the catalytic function of the EGF receptors, are consequently useful for the treatment of this disease.

The mitogen-activated protein kinase (MAPK) pathway is a major pathway in the cellular signal transduction cascade from growth factors to the cell nucleus. The pathway involves kinases at two levels: MAP kinase kinases (MAPKK), and their substrates MAP kinases (MAPK). There are different isoforms in the MAP kinase family. [For review, see Seger, R.; Krebs, E. G., *FASEB*, 9, 726 (1995)]. The compounds of this invention can inhibit the action of two of these kinases: MEK, a MAP kinase kinase, and its substrate ERK, a MAP kinase. MEK is activated by phosphorylation on two serine residues by upstream kinases such as members of the raf family. When activated, MEK catalyzes phosphorylation on a threonine and a tyrosine residue of ERK. The activated ERK then phosphorylates and activates transcription factors in the nucleus, such as fos and jun, or other cellular targets with PXT/SP sequences. ERK, a p42 MAPK is found to be essential for cell proliferation and differentiation. Overexpression and/or over-activation of MEK or ERK has been found to be associated with various human cancers [For example, Sivaraman, V. S.; Wang, H. -Y.; Nuovo, G. J.; Malbon, C. C., *J. Clin. Invest.* 99, 1478 (1997)]. It has been demonstrated that inhibition of MEK prevents activation of ERK and subsequent activation of ERK substrates in cells, resulting in inhibition of cell growth stimulation and reversal of the phenotype of ras-transformed cells [Dudley, D. T.; Pang, L.; Decker, S. J.; Bridges, A. J.; Saltiel, A. R., *Proc. Nat. Acad. Sci.*, 92, 7686, (1995)]. Since, as demonstrated below, the compounds of this invention can inhibit the coupled action of MEK and ERK, they are useful for the treatment of diseases such as cancer which are characterized by uncontrolled cell proliferation and which, at least in part, depend on the MAPK pathway.

Members of the raf family of kinases phosphorylate serine residues on MEK. There are three serine/threonine kinase members of the raf family known as a-raf, b-raf and c-raf. While mutations in the raf genes are rare in human cancers, c-raf is activated by the ras oncogene which is mutated in a wide number of human cancers. Therefore inhibition of the kinase activity of c-raf may provide a way to prevent ras mediated tumor growth [Campbell, S. L., *Oncogene*, 17, 1395 (1998)].

c-Met, a receptor tyrosine kinase, and its ligand, scatter factor (SF), are involved in epithelial cell proliferation and motility, and c-Met is overexpressed in a variety of neoplastic tissues. Simultaneous expression of HGF (hepatocyte growth factor) and c-Met in a non-tumor murine cell line results in transformation and metastasis in vivo [review: Jeffers, M., et al, *J. of Molecular Medicine* 74, 505 (1996)]. Kaji et al reported that antisense oligonucleotides which bind the start codon of c-Met, result in significantly decreased cell number of gastric carcinoma cell lines [Kaji, M., et al, *Cancer Gene Therapy*, 3, 393 (1996)]. The compounds of this invention can inhibit c-Met kinase, and are consequently useful for treatment of this disease.

Epithelial Cell Kinase (ECK) is a receptor protein tyrosine kinase (RPTK) belonging to the EPH (Erythropoietin Producing Hepatoma) family. Although originally identified as an epithelial lineage-specific tyrosine kinase, ECK has subsequently been shown to be expressed on vascular endothelial cells, smooth muscle cells, and fibroblasts. ECK is a type I transmembrane glycoprotein with the extracellular ligand-binding domain consisting of a cysteine-rich region followed by three fibronectin type m repeats. The intracellular domain of ECK possesses a tyrosine kinase catalytic domain that initiates a signal transduction cascade reflecting the ECK function. ECK binds and is subsequently activated by its counter-receptor, Ligand for Eph-Related Kinase (LERK)-1, which is an immediate early response gene product readily inducible in a lineage-unrestricted manner with proinflammatory cytokines such as IL-1 or TNF. Soluble LERK-1 has been shown to stimulate angiogenesis in part by stimulating ECK in a murine model of corneal angiogenesis. Unlike their normal counterparts, tumor cells of various lineages constitutively express LERK-1 and this expression can further be upregulated by hypoxia and proinflammatory cytokines. Many of these tumor cells also express ECK at higher levels than their normal counterparts, thereby creating an opportunity for autocrine stimulation via ECK: LERK-1 interaction. The increased expression of both ECK and LERK-1 has been correlated with the transformation of melanomas from the noninvasive horizontal phase of growth into very invasive vertically growing metastatic melanomas. Together, the ECK LERK-1 interaction is believed to promote tumor growth via its tumor growth promoting and angiogenic effects. Thus, the inhibition of the ECK tyrosine kinase activity mediating signaling cascade induced by its binding and cross-linking to LERK-1 may be therapeutically beneficial in cancer, inflammatory diseases, and hyperproliferative disorders.

The Src family of cytoplasmic protein tyrosine kinases consists of at least eight members (Src, Fyn, Lyn, Yes, Lck, Fgr, Hck and Blk) that participate in a variety of signaling pathways [Schwartzberg, P. L., *Oncogene*, 17, 1463–1468, (1998)]. The prototypical member of this tyrosine kinase family is $p60^{src}$ (Src). Src is involved in proliferation and migration responses in many cell types. In limited studies, Src activity has been shown to be elevated in breast, colon (~90%), pancreatic (>90%) and liver (>90%) tumors. Greatly increased Src activity is also associated with metastasis (>90%) and poor prognosis. Antisense Src message impedes growth of colon tumor cells in nude mice [Staley et al., *Cell Growth & Differentiation*., 8, 269–74, (1997)], suggesting that Src inhibitors should slow tumor growth. In addition to its role in cell proliferation, Src also acts in stress response pathways, including the hypoxia response, and nude mice studies with colon tumor cells expressing antisense Src message have reduced vascularization [Ellis, et al.,*J. Biol. Chem.*, 273, 1052–7 (1998)], which suggests that Src inhibitors would be anti-angiogenic as well as anti-proliferative.

Growth of most solid tumors is dependent on the angiogenesis involving activation, proliferation and migration of vascular endothelial cells and their subsequent differentiation into capillary tubes. Angiogenization of tumors allows them access to blood-derived oxygen and nutrients, and also provides them adequate perfusion. Hence inhibiting angiogenesis is an important therapeutic strategy in not only cancer but also in a number of chronic diseases such as rheumatoid arthritis, psoriasis, diabetic retinopathy, age-related macular degeneration, and so on. Tumor cells produce a number of angiogenic molecules. Vascular Endothelial Growth Factor (VEGF) is one such angiogenic factor. VEGF, a homodimeric disulfide-linked member of the PDGF family, is an endothelial cell-specific mitogen and is known to cause profound increase in the vascular endothelial permeability in the affected tissues. VEGF is also a senescence-preventing survival factor for endothelial cells. Almost all nucleated tissues in the body possess the capability to express VEGF in response to various stimuli including hypoxia, glucose deprivation, advanced glycation products, inflammatory cytokines, etc. Growth-promoting angiogenic effects of VEGF are mediated predominantly via its signaling receptor Kinase insert Domain containing Receptor (KDR). The expression of KDR is low on most endothelial cells; however, activation with angiogenic agents results in a significant upregulation of KDR on endothelial cells. Most angiogenized blood vessels express high levels of KDR. Binding to VEGF causes dimerization of KDR resulting in its autophosphorylation and initiation of a signaling cascade. Tyrosine kinase activity of KDR is essential for mediation of its functional effects as a receptor for VEGF. Inhibition of KDR-mediated functional effects by inhibiting KDR's catalytic activity is considered to be an important therapeutic strategy in the treatment of angiogenized disease states including cancer. Normal angiogenesis is required in many physiological conditions such as wound healing, female reproduction and fetal development. Abnormal or pathological angiogenesis has been implicated in neoplastic diseases including solid tumor growth, metastasis, and Kaposi's sarcoma; various eye diseases including diabetic retinopathy, and macular degeneration; inflammatory conditions including rheumatoid arthritis, and osteoarthritis; skin diseases including psoriasis, eczema and scleroderma; as well as ulcerative colitis and childhood haemangiomas [Toi, M. et al., *Breast Cancer Res. And Treat.*, 36, 192–204 (1995); Folkman, J., *Nature Medicine*, 1, 27–31 (1995); Jackson, J. R. et al., *FASEB J*., 11, 457–465 (1997)]. Inhibition of VEGF function has been shown to inhibit disease progression in tumors [Borgstrom, P. et al., *Cancer Res.*, 56, 4032–4039 (1996); Kim, J. K. et al., *Nature*, 362, 841–844 (1993)] and retinal neovascularization [Aiello, L. P. et al., *Proc. Nat. Acad. Sci.*, 92, 10457–10461 (1995)] as well as vascular dysfunction mediated by glucose in models of diabetes [Tilton, R. G. et al.,*J. Clin. Invest.*, 99, 2192–2202 (1997)].

Some 3-cyano-quinoline derivatives are inhibitors of tyrosine kinases and are described in: WO-98/43960 (U.S. Pat. No. 6,002,008). The patent U.S. Pat. No. 5,780,482 and application WO-95/00511 describe some condensed 4-aminopyridine compounds that have antirheumatic activity and can contain a cyano group at the 3-position. A 3-cyano-quinoline with a 4-(2-methylanilino) substituent having gastric (H+/K+)-ATPase inhibitor activity at high concentrations has been described [Ife, R. J., et al., *J. Med. Chem.*, 35 (18), 3413 (1992)].

Quinolines that do not have the 3-cyano substituent have been reported, and, unlike the compounds of this invention, are unsubstituted at the 4-position but are reported to be inhibitors of protein tyrosine kinases [Gazit A., et al., *J. Med. Chem.*, 39(11), 2170 (1996)]. A series of quinolines that have a 3-pyridyl substituent and no substituent at the 4-position have been described as inhibitors of platelet derived growth factor receptor kinase [Dolle, R. E., et al., *J. Med. Chem.*, 372, 2627 (1994) and Maguire, M. P., et al., *J. Med. Chem.*, 372, 129 (1994)]. The patent application WO 96/09294 describes inhibitors of protein tyrosine kinases that include 4-anilino quinolines with a large variety of substituents on positions 5–8 but which must also have a hydrogen atom at position 3. An international patent WO-98/13350 describes 3-fluoroquinoline and quinoline tyrosine kinase inhibitors. The U.S. Pat. No. 5,480,883 describes quinoline derivatives that are inhibitors of protein tyrosine kinases but these derivatives do not have the the 3-cyano group.

Certain tricyclic compounds are reported in the applications WO-92/02508, EP-412848 and EP-456442 where positions 6 and 7 of the 3-cyano-quinoline are substituted with alkylene-dioxy groups forming a third ring of size 5–8, however, the only hetero atoms present in the third ring are two oxygen atoms; furthermore, only tricycles substituted with alkoxy groups at the 4-position are claimed as angiotensin II antagonists. The U.S. Pat. No. 6,002,008 describes that contiguous carbon atoms of 5–8 of 3-cyano-quinolines are substituted with, ethylen-dioxy, a divalent radical to form tricyclic compounds as inhibitors of protein tyrosine kinases, however, the only hetero atoms present in the third ring are two oxygen atoms.

The compounds of this invention are certain 2,3-dihydro-1H-[1,4]oxazino[3,2-g]quinolines, 3,4-dihydro-2H-[1,4]oxazino[2,3-g]quinolines, 2,3-dihydro-1H-[1,4]thiazino[3,2-g]quinolines, and 3,4-dihydro-2H-[1,4]thiazino[2,3-g]quinolines which are inhibitors of protein tyrosine kinase and are useful as antineoplastic agents.

SUMMARY OF THE INVENTION

In accordance with the present invention, there is provided compounds represented by Formula (1):

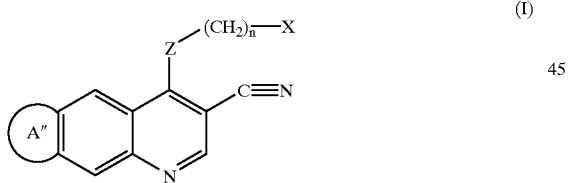

wherein:
Z is —NH—, —O—, —S(O)$_a$—, or —NR—;
R is alkyl of 1 to 6 carbon atoms, or carboalkyl of 2 to 7 carbon atoms;
X is cycloalkyl of 3 to 7 carbon atoms, which may be optionally substituted with one or more alkyl of 1 to 6 carbon atom groups; or
X is pyridinyl, pyrimidinyl, or an aryl ring; wherein the pyridinyl, pyrimidinyl or aryl ring may be optionally mono-, di-, or tri-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, methylmercapto, and benzoylamino; or X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of I to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamiino of 3 to 8 carbon atoms, carboxyalkyl of 2 to 7 carbon atoms, caiboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, methylmercapto, and benzoylamino; or X is the radical

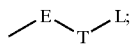

E is pyridinyl, pyrimidinyl, or an aryl ring; wherein the pyridinyl, pyrimidinyl or aryl ring may be optionally mono-, di-, or tri-substituted with a substituent selected from the group consisiting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, methylmercapto, and benzoylamino;

T is substituted on E at a carbon and is
—NH(CH$_2$)$_m$—, —O(CH$_2$)$_m$—, —S(O)$_a$—(CH$_2$)$_m$—, —NR(CH$_2$)$_m$—, —(CH$_2$)$_m$—
—(CH$_2$)$_m$NH—, —(CH$_2$)$_m$O—, —(CH$_2$)$_m$S(O)$_a$—, or —(CH$_2$)$_m$NR —;

L is an aryl ring; that is optionally mono-, di, or trisubstituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, methylmercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, methylmercapto, and benzoylamino;

A″ is a moiety selected from the group

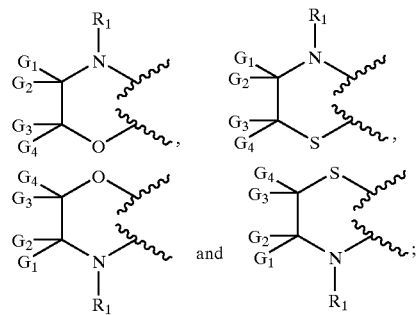

$G_1$, $G_2$, $G_3$ and $G_4$ are independently selected from the group consisting of hydrogen, and alkyl of 1 to 6 carbon atoms;

$R_1$ is —H, $R_{11}$—CH$_2$—, —$R_{12}$,

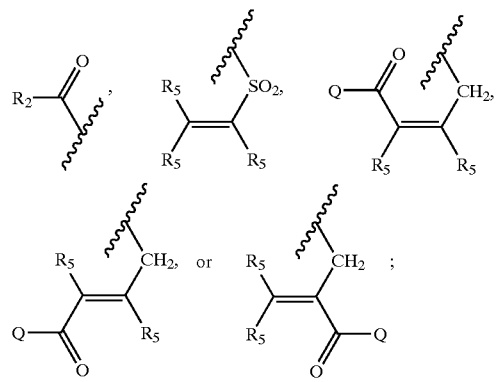

$R_{11}$ is —H, alkyl of 1 to 5 carbon atoms, aryl, or $R_{13}$—(C(R$_6$)$_2$)$_k$—;

$R_{13}$ is

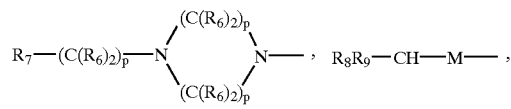

$R_7$—, $R_7$—(C(R$_6$)$_2$)$_p$—M—, or Het-(C(R$_6$)$_2$)$_q$—W—;

$R_7$ is —H, —NR$_6$R$_6$, —OR$_6$, —J, —N(R$_6$)$_3^+$, or —NR$_6$(OR$_6$);

M is

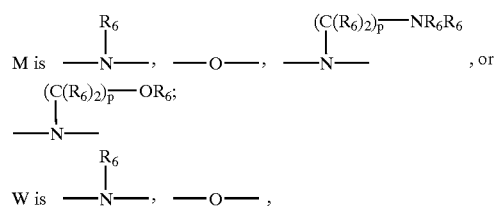

W is —N(R$_6$)—, —O—, or a bond;

Het is a heterocyclic radical selected from the group consisting of morpholine, thiomoipholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

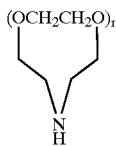

optionally mono- or di-substituted on carbon by —$R_6$, hydroxy, —$N(R_6)_2$, —$OR_6$, —$(C(R_6)_2)_s OR_6$, or —$(C(R_6)_2)_s N(R_6)_2$; or optionally mono—substituted on nitrogen with —$R_6$; and optionally mono or di—substituted on a saturated carbon with divalent radicals —O—, or —$O(C(R_6)_2)_s O$—;

$R_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms,

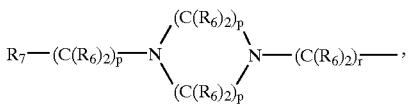

$R_7$—$(C(R_6)_2)_s$—, $R_7$—$(C(R_6)_2)_p$—M—$(C(R_6)_2)_r$—, $R_8 R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_r NR_6 R_6$, or —$(C(R_6)_2)_r OR_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;

Q' is alkyl of 1 to 6 carbon atoms;

$R_2$ is selected from the group consisting of

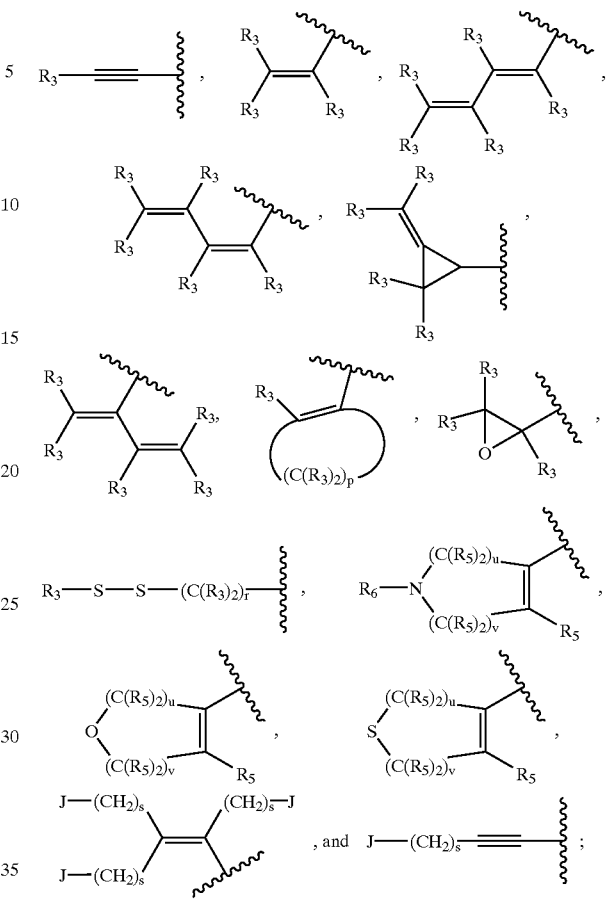

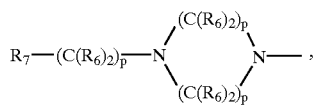

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;

$R_{3a}$ is $R_7$—$(C(R_6)_2)_p$—N$\underset{(C(R_6)_2)_p}{\overset{(C(R_6)_2)_p}{\diagup\!\!\diagdown}}$N—, $R_7$—, $R_7$—$(C(R_6)_2)_p$—M—, $R_8 R_9$—CH—M—, or Het-$(C(R_6)_2)_q$—W—;

a is 0 to 2;
k is 1, 3 to 5;
n is 0 to 1;
m is 0 to 3;
p is 2 to 4;
q is 0 to 4;
r is 1 to 4;
s is 1 to 6;
u is 0 to 4 and v is 0 to 4, wherein the sum of u+v is 2 to 4;

provided that:
  a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
b. when $R_3$ is bound to sulfur, $R_3$ is not —H, carboxy, carboalkoxy, or carboalkyl;
c. when M is —O—, and $R_7$ is —$OR_6$, then p is 1 to 4;
d. when M is —O—, then k is 1 to 5;
e. when W is —O—, then k is 1 to 5;
f. when $R_7$ is —$OR_6$, then k is 1 to 5;
g. when W is not a bond with Het bonded through a nitrogen atom, q is 2 to 4, and when W is a bond, q is 0;

or a pharmaceutically acceptable salt thereof.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Throughout this patent application, the quinoline and tricyclic ring systems will be numbered as indicated in the formulas below.

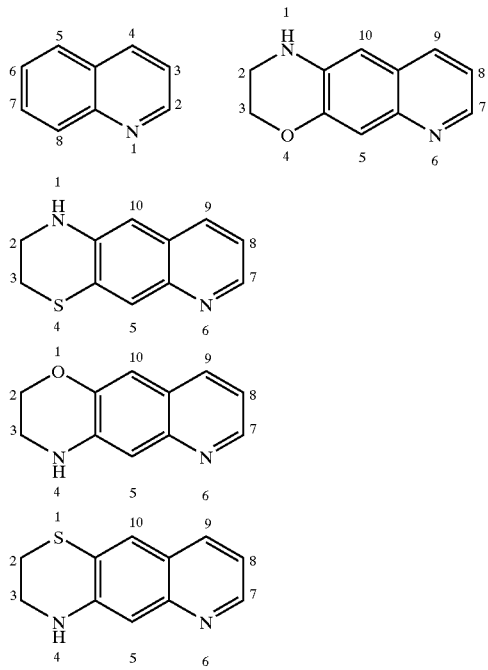

Preferred bicyclic aryl or bicyclic heteroaryl ring systems include naphthalene, 1,2,3,4-tetrahydronaphthalene, indan, 1-oxo-indane, 1,2,3,4-tetrahydroquinoline, naphthyridine, benzofuran, 3-oxo-1,3-dihydro-isobenzofuran, benzothiaphene, 1,1-dioxo-benzothiaphene, indole, 2,3-dihydroindole, 1,3-dioxo-2,3-dihydro-1H-isoindole, benzotriazole, 1H-indazole, indoline, benzopyrazole, 1,3-benzodioxole, benzooxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-benzodioxane, pteridine, 2(1H)-quinolone, 1(2H)-isoquinolone, 2-oxo-2,3-dihydro-benzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, 1,4-dioxo-1,2,3,4-tetrahydro-phthalazine, 2-oxo-1,2-dihydro-quinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring, preferred heteroaryl rings include pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms is substituted with a carbonyl group. A thio substituent on the bicyclic aryl or bicyclic heteroaryl moiety means that one of the carbon atoms is substituted with a thiocarbonyl group. When a compound of this invention contains a moiety which contains a heteroaryl ring, such heteroaryl ring does not contain O—O, S—S, or S—O bonds in the ring.

When L is a 5 or 6-membered heteroaryl ring, it may be fully unsaturated, partially saturated, or fully saturated. The heteroaryl ring may be bound to T via carbon or nitrogen. An oxo substituent on the heteroaryl ring means that one of the carbon atoms is substituted with a carbonyl group. A thio substituent on the heteroaryl ring means that one of the carbon atoms is substituted with a thiocarbonyl group.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, N,N-dialkylcarbamoyl, N-alkylaminoalkoxy, and N,N-dialkylaminoalkoxy include both straight chain as well as branched carbon chains of 1 to 7 carbon atoms. The alkenyl portion of the alkenyl, alkenoyloxymethyl, alkenyloxy, alkenylsulfonamido, substituents include both straight chain as well as branched carbon chains of 1 to 7 carbon atoms and one or more sites of unsaturation and all possible configurational isomers. The alkynyl portion of the alkynyl, alkynoyloxymethyl, alkynylsulfonamido, alkynyloxy, substituents include both straight chain as well as branched carbon chains of 2 to 7 carbon atoms and one or more sites of unsaturation. Carboxy is defined as a —$CO_2H$ radical. Carboalkoxy of 2 to 7 carbon atoms is defined as a —$CO_2R''$ radical, where R'' is an alkyl radical of 1 to 6 carbon atoms. Carboxyalkyl is defined as a $HO_2C$—R'''— radical where R''' is a divalent alkyl radical of 1 to 6 carbon atoms. Carboalkoxyalkyl is defined as a R''$O_2C$—R'''— radical where R''' is a divalent alkyl radical and where R'' and R''' together have 2 to 7 carbon atoms. Carboalkyl is defined as a —COR'' radical, where R'' is an alkyl radical of 1 to 6 carbon atoms. Alkanoyloxy is defined as a —OCOR'' radical, where R'' is an alkyl radical of 1 to 6 carbon atoms. Alkanoyloxymethyl is defined as R''$CO_2CH_2$— radical, where R'' is an alkyl radical of 1 to 6 carbon atoms. Alkoxymethyl is defined as R''$OCH_2$— radical, where R'' is an alkyl radical of 1 to 6 carbon atoms. Alkylsulphinyl is defined as R''SO— radical, where R'' is an alkyl radical of 1 to 6 carbon atoms. Alkylsulphonyl is defined as R''$SO_2$— radical, where R'' is an alkyl radical of 1 to 6 carbon atoms. Alkylsulfonamido, alkenylsulfonamido, alkynylsulfonamido are defined as R''$SO_2NH$— radical, where R'' is an alkyl radical of 1 to 6 carbon atoms, an alkenyl radical of 2 to 6 carbon atoms, or an alkynyl radical of 2 to 6 carbon atoms, respectively. N-alkylcarbamoyl is defined as R''NHCO— radical, where R'' is an alkyl radical of 1 to 6 carbon atoms. N,N-dialkylcarbamoyl is defined as R'' R'NCO— radical, where R'' is an alkyl radical of 1 to 6 carbon atoms, R' is an alkyl radical of 1 to 6 carbon atoms and R', and R'' may be the same or different. When X is substituted, it is preferred that it is mono-, di-, or tri-substituted, with mono- and di-substituted being most preferred. A preferred embodiment of this invention is that $G_1$, $G_2$, $G_3$, and $G_4$, are hydrogen. It is also preferred that X is a phenyl ring, Z is —NH—, and n=0.

Het is a heterocyclic radical selected from the group consisting of morpholine, thiomorpholine, thiomorpholine S-oxide, thiomorpholine S,S-dioxide, piperidine, pyrrolidine, azinidine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

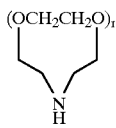

which may be optionally mono- or disubstituted on carbon with $R_6$, optionally mono-substituted on nitrogen with $R_6$, optionally mono- or di-substituted on carbon with hydroxy, —N$(R_6)_2$, or —O$R_6$, optionally mono or di-substituted on carbon with —$(C(R_6)_2)_s$O$R_6$ or —$(C(R_6)_2)_s$N$(R_6)_2$, and optionally mono or di-substituted on a saturated carbon with divalent —O— or —O$(C(R_6)_2)_s$O— (carbonyl and ketal groups, respectively); in some cases when Het is substituted with —O— (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with $R_6$, such substitution may be on a ring carbon, or in the case of a nitrogen containing heterocycle, which also contains a saturated carbon-nitrogen, such nitrogen may be substituted with $R_6$ or in the case of a nitrogen containing heterocycle, which also contains an unsaturated carbon-nitrogen, such nitrogen may be substituted with $R_6$ in with case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-subsitituted 1,4-piperazine, N-substituted piperadine, and N-substituted pyrrolidine.

Aryl is a phenyl ring which may be optionally mono-, di-, or tri-substituted with a substituent independently selected from the group consisiting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, methylmercapto, and benzoylamino.

Phenyl as used herein refers to a 6-membered aromatic ring optionally mono, di or tri-substituted.

The compounds of this invention may contain one or more asymmetric carbon atoms; in such cases, the compounds of this invention include the individual diastteromers, the racemates, and the individual R and S entantiomers thereof. Some of the compounds of this invention may contain one or more double bonds; in such cases, the compounds of this invention include each of the possible configurational isomers as well as mixtures of these isomers. When a compound of this invention contains a moiety containing the same substituent more than once (for example, when $R_7$ is —N$R_6R_6$), each substituent ($R_6$, in this example) may be the same or different.

Preferred compounds of this invention are described below. Except as otherwise indicated below, the substituents are as defined above.

A. Compounds according to Formula (1), wherein Z is —NH—, n is 0, X is aryl and A" is the moiety

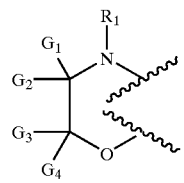

or a pharmaceutically acceptable salt thereof.

B. Compounds according to Formula (I), wherein Z is —NH—, n is 0, X is aryl and A" is the moiety

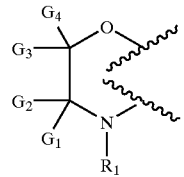

or a pharmaceutically acceptable salt thereof.

C. Compounds according to Formula (I) wherein Z is —NH—, n is 0, X is aryl and A" is the moiety

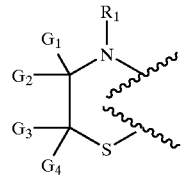

or a pharmaceutically acceptable salt thereof.

D. Compounds according to Formula (I), wherein Z is —NH—, n is 0, X is aryl and A" is the moiety

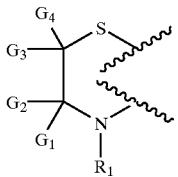

or a pharmaceutically acceptable salt thereof.

E. Compounds according to Formula (I), wherein Z is —NH—, n is 0, X is aryl and A" is the moiety

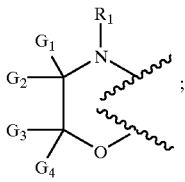

$G_1$, $G_2$, $G_3$, and $G_4$ are H;
or a pharmaceutically acceptable salt thereof.

F. Compounds according to Formula (I) wherein Z is —NH—, n is 0, X is aryl and A" is the moiety

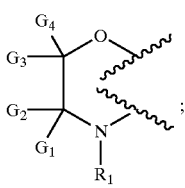

$G_1$, $G_2$, $G_3$, and $G_4$ are H;
or a pharmaceutically acceptable salt thereof.

G. Compounds according to Formula (I) wherein Z is —NH—, n is 0, X is aryl and A" is the moiety

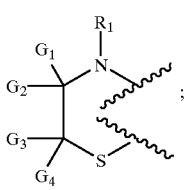

$G_1$, $G_2$, $G_3$, and $G_4$ are H;
or a pharmaceutically acceptable salt thereof.

H. Compounds according to Formula (I), wherein Z is —NH—, n is 0, X is aryl and A" is the moiety

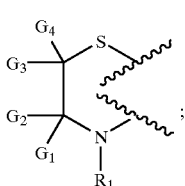

$G_1$, $G_2$, $G_3$, and $G_4$ are H;
or a pharmaceutically acceptable salt thereof.

I. Compounds according to Formula (1), wherein Z is —NH—, n is 0, X is aryl and A" is the moiety

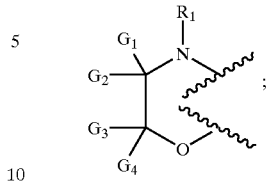

$R_1$ is selected from H, $R_2C(O)$— and $R_{11}$—$CH_2$—;
or a pharmaceutically acceptable salt thereof.

J. Compounds according to Formula (I) wherein Z is —NH—, n is 0, X is aryl and A" is the moiety

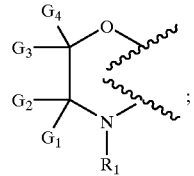

$R_1$ is selected from H, $R_2C(O)$— and $R_{11}$—$CH_2$—;
or a pharmaceutically acceptable salt thereof.

K. Compounds according to Formula (I) wherein Z is —NI—, n is 0, X is aryl and A" is the moiety

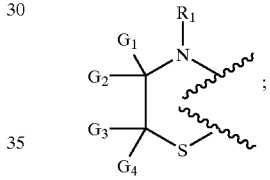

$R_1$ is selected from H, $R_2C(O)$— and $R_{11}$—$CH_2$—;
or a pharmaceutically acceptable salt thereof.

L. Compounds according to Formula (I), wherein Z is —NH—, n is 0, X is aryl and A" is the moiety

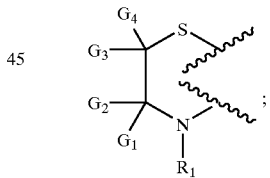

$R_1$ is selected from H, $R_2C(O)$— and $R_{11}$—$CH_2$—;
or a pharmaceutically acceptable salt thereof.

M. Compounds according to Formula (I), wherein Z is —NH—, n is 0, X is aryl and A" is the moiety

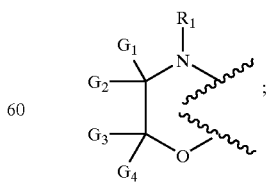

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

N. Compounds according to the Formula (I) wherein Z is
—NH—, n is 0, X is aryl and A" is the moiety

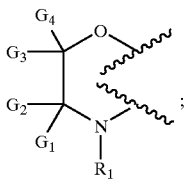

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

O. Compounds according to Formula (I) wherein Z is —NH—, n is 0, X is aryl and A" is the moiety

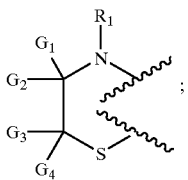

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

P. Compounds according to Formula (I), wherein Z is —NH—, n is 0, X is aryl and A" is the moiety

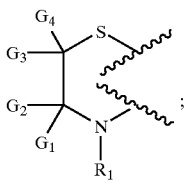

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

Specifically preferred compounds of this invention include:

9-(3-Chloro-4-fluoroanilino)-2,3-dihydro-1H-[1,4]oxazino[3,2-g]quinoline-8-carbonitrile, 1-[(2E)-4-Chloro-2-butenoyl]-9-(3-chloro-4-fluoroanilino)-2,3-dihydro-1H-[1,4]oxazino[3,2-g]quinoline-8-carbonitrile, 1-[(2E)-4-Bromo-2-butenoyl ]-9-(3-chloro-4-fluoroanilino)-2,3-dihydro-1H-[1,4]oxazino[3,2-g]quinoline-8-carbonitrile, 9-(3-Chloro-4-fluoroanilino)-1-[(2E)-4-(dimethylamino)-2-butenoyl]-2,3-dihydro-1-H-[1-[1,4]oxazino(3,2-g]quinoline-8-carbonitnile, 9-(3-Chloro-4-fluoroanilino)-1-[4-(dimethylamino)butanoyl]-2,3-dihydro-1H-[1,4]oxazino[3,2-g]quinoline-8-carbonitrile, 1-(4-Chlorobutyl)-9-(3-chloro-4-fluoroanilino)-2,3-dihydro-1H-[1,4]oxazino[3,2-g]quinoline-8-carbonitrile, 9-(3-Chloro-4-fluoroanilino)-1-[4-(dimethylamino) butyl]-2,3-dihydro-1H-[1,4]oxazino[3,2-g]quinoline-8-carbonitrile, 9-(2,4-Dichloroanilino)-3,4-di hydro-2H-[1,4]oxazino[2,3-g]quinoline-8-carbonitrile, 4-(4-Chlorobutyl)-9-(2,4-dichloroanilino)-3,4-dihydro-2H-[1,4]oxazino[2,3-g]quinoline-8-carbonitrile, and 9-(2,4-Dichloroanilino)-4-[4-(4-ethyl-1-piperazinyl)butyl]-3,4-dihydro-2H-[1,4]oxazino[2,3-g]quinoline-8-carbonitrile, or a pharmaceutically acceptable salt thereof.

DESCRIPTION OF PREFERRED EMBODIMENTS

The compounds of this invention may be prepared from commercially available starting materials or starting materials which may be prepared using literature procedures. More specifically, the preparation of compounds and intermediates of this invention, 4-substituted-quinoline-3-carbonitriles 9 is described below in Flowsheet 1 where X, n, and Z are as hereinbefore described. The condensation of substituted-anilines 2 and 2-cyano-3-ethoxy-acrylic acid ethyl ester 3 by heating in the absence of solvent gives esters 4, wherein $R_4$ is a methyl or an ethyl group. Thermal cyclization of esters 4 in refluxing 3:1 diphenyl ether/biphenyl or diphenyl ether gives 4-oxo-1,4-dihydro-quinoline-3-carbonitriles 5, which may also exist in the 4-hydroxy-quinoline tautomeric form. Nitration of 4-oxo-1, 4-dihydro-qLlinoline-3-carbonitriles 5 in trifluoroacetic acid (TFA) with ammonium nitrate at room temperature gives the nitro compounds 6. Nitro compounds 6 are refluxed with chlorinating reagent selected from the group consisting of phosphorous oxychloride, oxalyl chloride, phosphorous oxychloride and phosphorus pentachloride to furnish 4-chloro compounds 7. Condensation of 4-chloro compounds 7 with various amines, anilines, alcohols, phenols, mercaptans, and thiophenols of the Formula HZ—$(CH_2)_n$—X 7a where Z, X and n are hereinbefore defined gives 4-substituted-6-nitro-quinoline-3-carbonitriles 8. This condensation may be accelerated by heating the reaction mixture together with one equivalent of pyridine hydrochloride in alcohol solvents which include isopropanol and 2-ethoxyethanol or by using bases such as trialkylamines, sodium hydride in an inert solvent which includes tetrahydrofuran (THF), sodium or potassium alkoxides in alcohol solvents which includes ethanol, and the like. Reduction of 4-substituted-6-nitro-quinoline-3-carbonitriiles 8 with iron and ammonium chloride in refluxing methanol and water furnishes 4-substituted-7-alkoxy-6-amino-quinoline-3-carbonitriles 9. Alternatively, reagents such as tin chloride and the like may be used.

Flowsheet 1

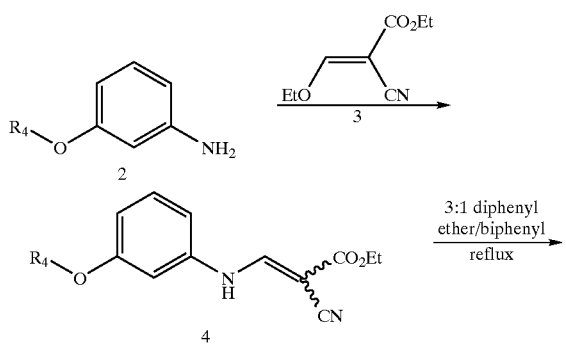

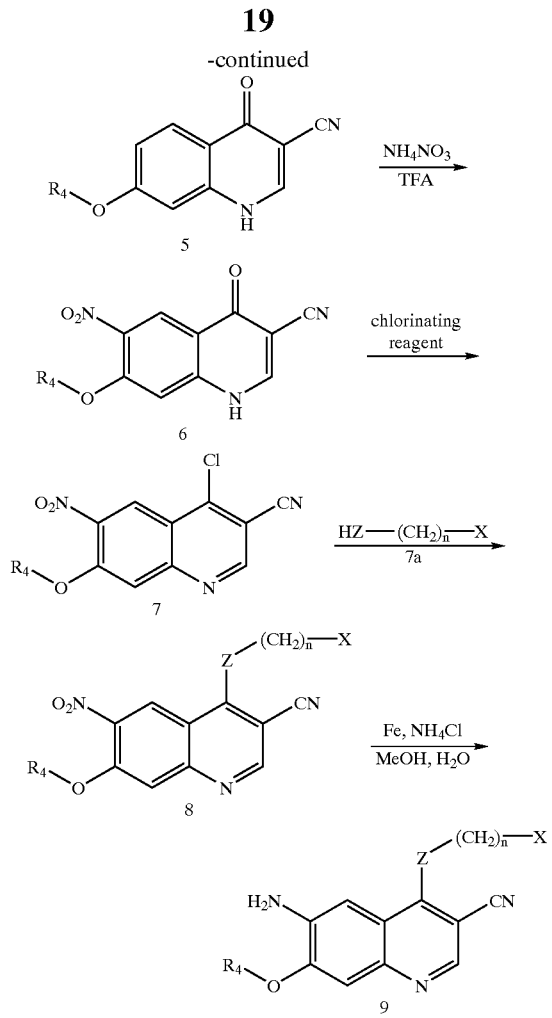

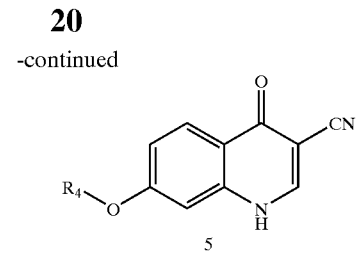

The 4-oxo-1,4-dihydro-quinoline-3-carbonitriles 5 may be prepared by an alternate route as described below in Flowsheet 2. Reaction of anthranilic acids 10 where $R_4$ is hereinbefore defined with dimethylformamide dimethylacetal (DMF-dimethyl acetal), with or without an inert solvent, gives intermediate esters 11. The reaction of intermediate esters 11 with the lithium anion of acetonitrile prepared by using a base which includes n-butyl lithium (n-BuLi) or the like in an inert solvent which includes tetrahydrofuran (THF) gives 4-oxo-1,4-dihydro-quinoline-3-carbonitriles 5.

Flowsheet 2

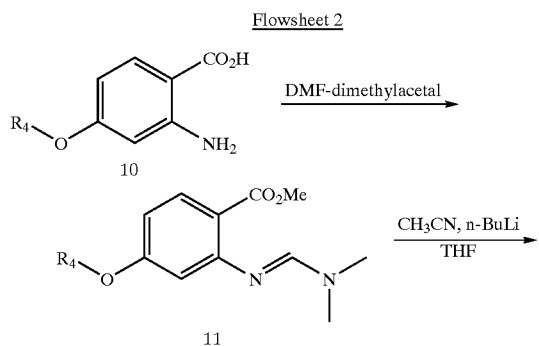

Compounds of Formula 9, which are important intermediates for the preparation of compounds of this invention, are prepared by an alternate route as described below in Flowsheet 3 where $R_4$, Z, n and X are hereinbefore defined. Acetylation of nitroanilines 12 with acetic anhydride ($Ac_2O$) and water at room temperature gives nitro compounds 13. Reduction of nitro compounds 13 with iron and ammonium chloride in refluxing methanol and water furnishes anilines 14. The condensation of anilines 14 and 2-cyano-3-ethoxy-acrylic acid ethyl ester 3 by heating in the absence of solvent gives esters 15. Thermal cyclization of esters 15 in refluxing 3:1 diphenyl ether/biphenyl or diphenyl ether gives 4-oxo-1,4-dihydro-quinoline-3-carbonitriles 16. Chlorination of 4-oxo-1,4-dihydro-quinoline-3-carbonitriles 16 in refluxing chlorinating reagent selected from phosphorous oxychloride and oxalyl chloride furnishes 4-chloro-quinolines 17. Condensation of 4-chloro-quinolines 17 with various amines, anilines, alcohols, phenols, mercaptans, and thiophenols of the Formnula HZ—$(CH_2)_n$—X 7a where Z, X and n are hereinbefore defined gives 4-substituted-6-acetamido-quinoline-3-carbonitriles 18. The condensation may be accelerated by heating the reaction mixture together with one equivalent of pyridine hydrochloride in alcohol solvents which include isopropanol and 2-ethoxyethanol or by using bases such as trialkylamines, sodium hydride in an ineil solvent which includes tetrahydrofuran (THF), sodium or potassium alkoxides in alcohol solvents which includes ethanol, and the like. Hydrolysis of 4-substituted-6-acetamido-quinoline-3-carbonitniles 18 in aqueous hydrochloric acid gives 4-substituted-6-amino-quinoline-3-carbonitiiles 9 where $R_4$, Z, n and X are hereinbefore defined.

Flowsheet 3

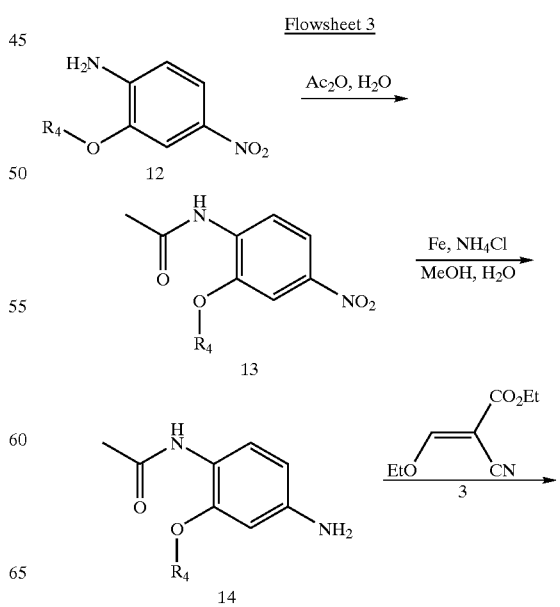

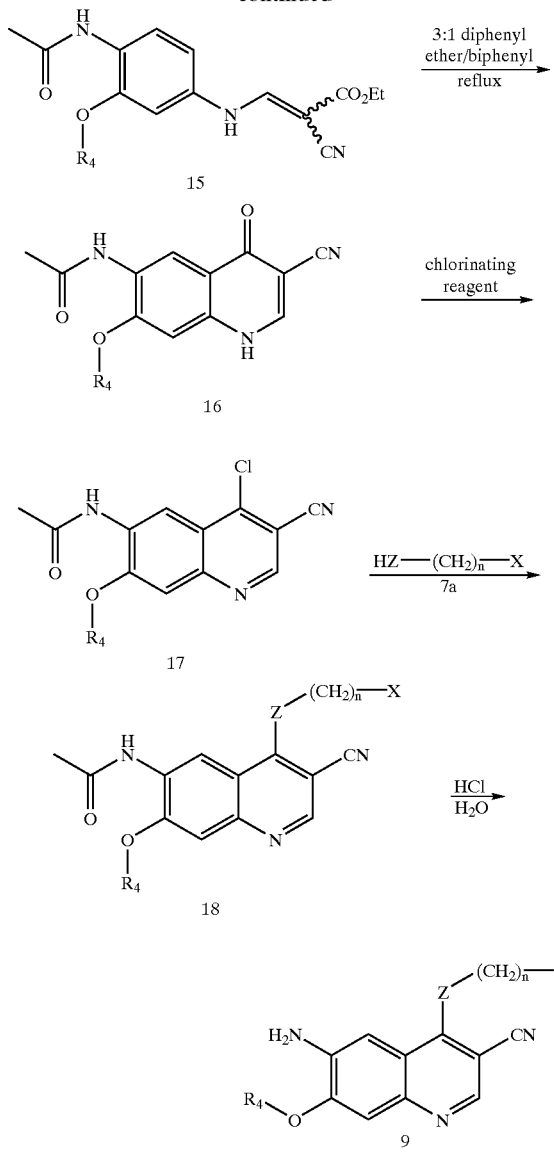
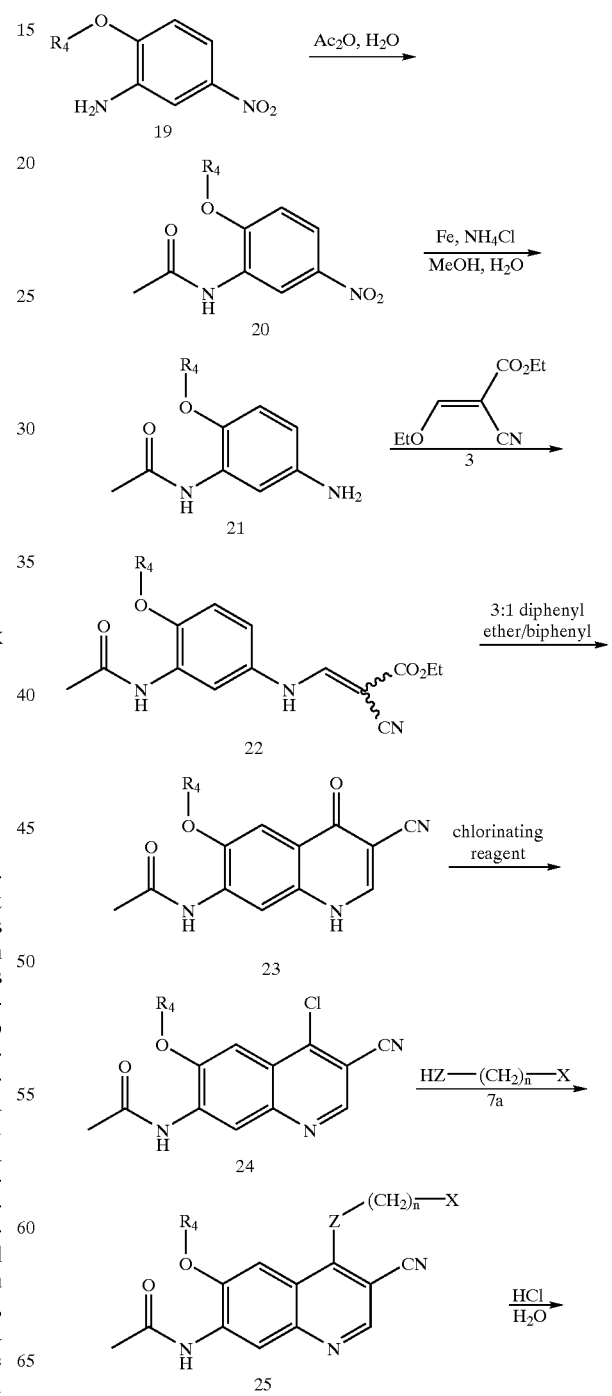

tion mixture together with one equivalent of pyridine hydrochloride in alcohol solvents which include isopropanol and 2-ethoxyethanol or by using bases which includes trialkylamines, sodium hydride in an inert solvent which includes tetrahydrofuran (THF), and the like, sodium or potassium alkoxides in alcohol solvents which includes ethanol, and the like. Hydrolysis of 4-substituted-7-acetamido-quinoline-3-carbonitriles 25 in aqueous hydrochloric acid gives 4-substituted-7-amino-quinoline-3-caibonitriles 26.

Flowsheet 4

The prepartion of the compounds of this invention encompassed by compounds of Formula 26, which are important intermediates for the preparation of compounds of this invention, is described below in Flowsheet 4 where $R_4$, Z, n and X are hereinbefore defined. Acetylation of nitroanilines 19 with acetic anhydride ($Ac_2O$) and water at room temperature gives nitro compounds 20. Reduction of nitro compounds 20 with iron and ammonium chloride in refluxing methanol and water furnishes anilines 21. The condensation of anilines 21 and 2-cyano-3-ethoxy-acrylic acid ethyl ester 3 by heating in the absence of solvent gives esters 22. Thermal cyclization of esters 22 in refluxing 3:1 diphenyl ether/biphenyl or diphenyl ether gives 4-oxo-1,4-dihydro-quinoline-3-carbonitriles 23. Chlorination of 4-oxo-1,4-dihydro-quinoline-3-carbonitriles 23 in refluxing chlorinating reagent selected from phosphorous oxychloride and oxalyl chloride gives 4-chloro-quinolines 24. Condensation of 4-chloro-quinolines 24 with various amines, anilines, alcohols, phenols, mercaptans, and thiophenols of Formula HZ—$(CH_2)_n$—X 7a where Z, X and n are hereinbefore defined gives 4-substituted-quinoline-3-carbonitriles 25. This condensation may be accelerated by heating the reac-

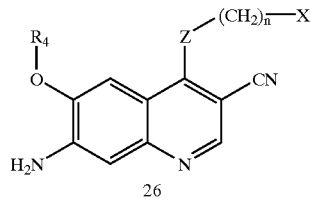

The preparation of the compounds and interrnediates of this invention encompassed by Formula 29 is described below in Flowsheet 5 where R$_4$, Z, n, X, G$_1$, G$_2$, G$_3$, and G$_4$ are hereinbefore defined. Dealkylation of 4-substituted-7-alkoxy-6-amino-quinoline-3-carbonitriles 9 is accomplished by heating with excess amount of pyridinium hydrochloride to give 4-substituted-6-amino-7-to hydroxy-quinoline-3-carbonitriles 27. In those cases where X of 4-substituted-7-alkoxy-6-amino-quinoline-3-carbonitriles 9 is an aryl, heteroaryl, bicyclic aryl or bicyclic heteroaryl which is substituted with a methoxy or an ethoxy group, the product 4-substituted-6-amino-7-hydroxy-quinoline-3-carbonitriles 27 may be a mixture containing mono-dealkylated and di-dealkylated compounds. The mixture may be separated by column chromatography to give the desired product 4-substituted-6-amino-7-hydroxy-quinoline-3-carbonitriles 27 where only the 7-alkoxy of 4-substituted-7-alkoxy-6-amino-quinoline-3-carbonitriles 9 is dealkylated. Condensation of 4-substituted-6-amino-7-hydmoxy-quinoline-3-carbonitiiles 27 with dibromides 28 where R$_4$, Z, n, X, G$_1$, G$_2$, G$_3$, and G$_4$ are hereinbefore defined in alcohol solvents including 2-ethoxyethanol, in the presence of potassium carbonate gives the tricyclic compounds 2,3-dihydro-1H-[1,4]oxazino[3,2-g]quinoline-8-carbonitriles 29 of this invention.

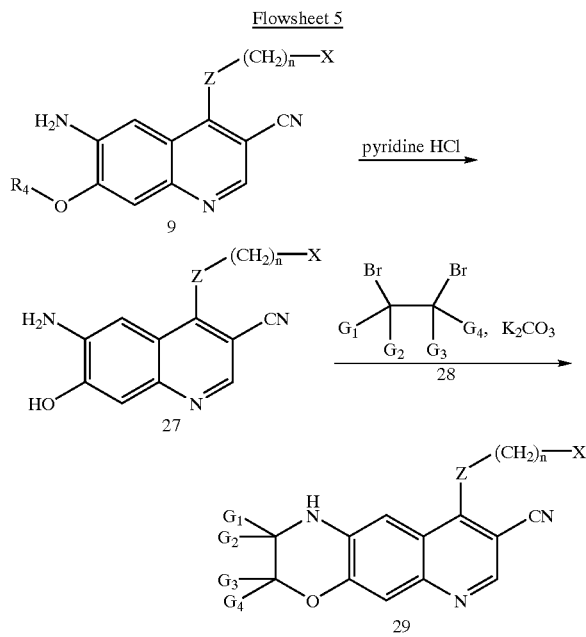

Flowsheet 5

By using similar methods, as shown in Flowsheet 5a, the intermediates 4-substituted-6-alkoxy-7-amino-quinoline-3-carbonitriles 26 may be converted to 3,4-dihydro-2H-[1,4]oxazino[2,3-g]qulinoline-8-carbonitniles of this invention 31.

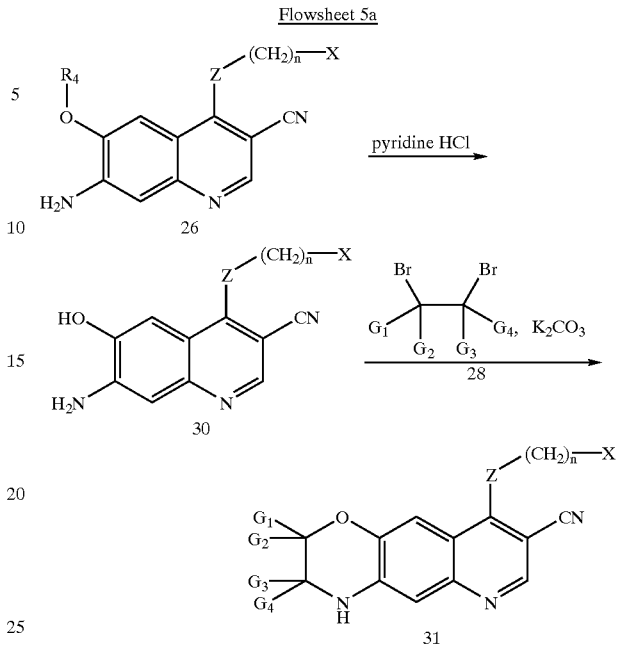

Flowsheet 5a

The preparation of the tricyclic compounds of this invention encompassed by 1-substituted-2,3-dihydro-1H-[1,4]oxazino[3,2-g]quinoline-8-carbonitriles of Formula 34 is described below in Flowsheet 6 wherein Z, n, X, G$_1$, G$_2$, G$_3$, and G$_4$ are hereinbefore defined. R$_{10}$ is alkyl of 1 to 6 carbon atoms (preferably isobutyl) and R$_2$— is a radical selected from the group consisting of:

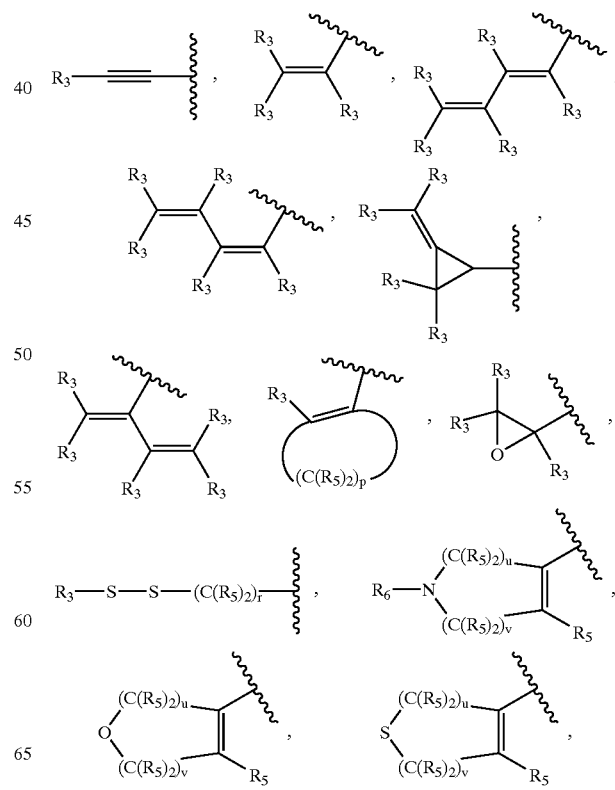

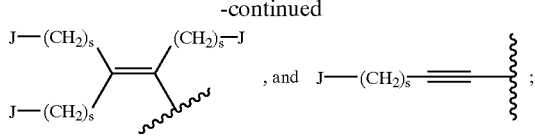

wherein $R_6$, $R_3$, $R_5$, J, s, r, u, and v are hereinbefore defined.

According to the reactions outlined in Flowsheet 6, acylation of 2,3-dihydro-1H-[1,4]oxazino[3,2-g]quinoline-8-carbonitriles 29 with either acid chlorides of Formula 32 or mixed anhydrides of Formula 33 (which are prepared from the corresponding carboxylic acids) in an ineil solvent such as tetrahydrofuran (THF) in the presence of an organic base selected from pyridine, triethylamine [$(C_2H_5)_3N$], N,N-diisopr-opylethylamine, and N-methylmorpholine and the like gives 1-substituted-2,3-dihydro-1H-[1,4]oxazinof3,2-g]quinoline-8-carbonitriles 34. In those cases where the acid chlorides 32 or the mixed anhydrides 33 have an asymmetric carbon atom, they may be used as the racemate or as the individual R or S entantiomers wherein the compounds of this invention will be in the racemic or R and S optically active forms, respectively. In those cases, where $R_2$ contains primary or secondary amino groups, the amino groups will first have to be protected priolr to anhydride or acid chloride formation. Suitable protecting groups include, but are not limited to, teii-butoxycarbonyl (BOC) and benzyloxycarbonyl (CBZ) protecting groups and the like. The BOC protecting group may be removed from the final products by treatment with an acid such as trifluoroactic acid (TFA) while the CBZ protecting group may be removed by catalytic hydrogenation. In those cases where $R_2$ contains hydroxyl groups, the hydroxyl groups may optionally need protection puior to treatment with an anhydride or acid chloride. Suitable protecting groups include, but are not limited to, t-butyldimethylsilyl, tetrahydropyranyl, or benzyl protecting groups. t-Butyldimethylsilyl and tetrahiydropyranyl protecting groups may be removed from the final products by treatment with an acid such as acetic acid or hydrochloric acid while the benzyl protecting group may be removed by catalytic hydrogenation. In those cases, in intermediates 2,3-dihydro-1H-[1,4]oxazino[3,2-g]quinoline-8-carbonitriles 29 where X contains primary or secondary amino groups or-hydroxyl groups, it may be necessary to protect these groups prior to the reaction with acid chlorides 32 or mixed anhydrides 33. The same amine or alcohol protecting groups describe above may be used and they may be removed from the products as previously described.

Flowsheet 6

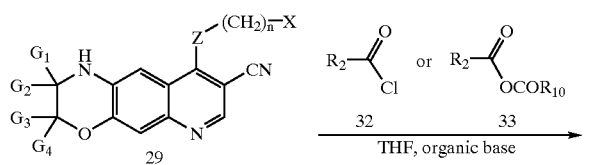

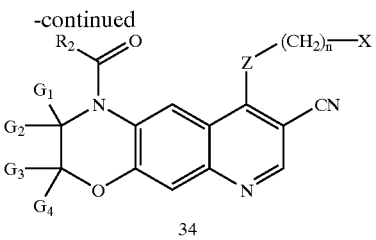

In a similar manner, 3,4-dihydro-2H-[1,4]oxazino[2,3-g]quinoline-8-carbonitriles of Formula 31 may be converted to 4-substituted-3,4-dihydro-2H-[1,4]oxazino[2,3-g]quinoline-8-carbonitriles of Formula 35 as shown in Flowsheet 6a. In those cases, in intermediates 3,4-dihydro-2H-[1,4]oxazino[2,3-g]quinoline-8-carbonitriles 31 where X contains primary or secondary amino groups or hydroxyl groups, it may be necessary to protect these groups prior to the reaction with acid chlorides 32 or mixed anhydrides 33. The same amine or alcohol protecting groups described above may be used and they may be removed from the products as previously described.

Flowsheet 6a

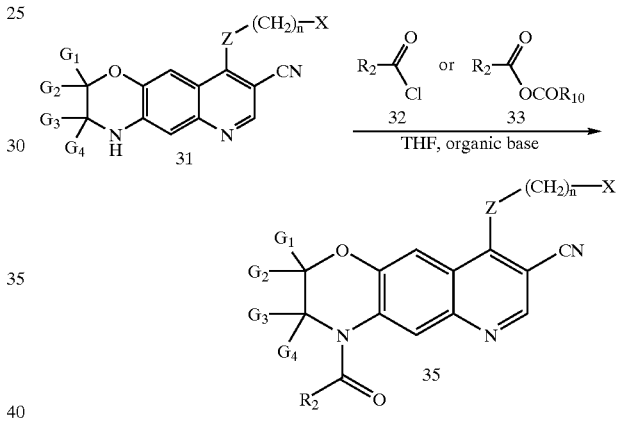

In order to prepare some of the compounds of this invention certain amines and mixed anhydrides are required; these are prepared as outlined below in the following Flowsheet 7 wherein $R_{3a}$, $R_6$, $R_{10}$, J', and s are as hereinbefore defined with the proviso that $R_{3a}H$ is an amine. Reaction of amines 170, $R_{3a}H$ with substitued-alkynes 36 is accomplished by heating in an inert solvent such as tetrahydrofuran (THF) or N,N-dimethylfoimamide (DMF), or using potassium or cesium carbonate in acetone to yield aminoalkynes 37. The temperature and duration of the heating will depend on the reactivity of alkynes 36; longer reaction times and higher temperatures may be required when s is greater than 1. Some representative $R_{3a}$— moieties of amines 170, $R_{3a}H$ are shown below in List A wherein $R_6$, p, and r are as defined above. The amines 170, $R_{3a}H$ are available commercially, are known in the chemical literature, or may be prepared by simple procedures that are well known in the art. In some cases, amines 170, $R_{3a}H$ may have one or more asymmetric carbon atoms; and they may be used as the racemate or they may be resolved and used as the individual R or S entantiomers in which case the compounds of this invention will be in the racemic or optically active forms, respectively. Treatment of aminoalkynes 37 with an alkyl lithium reagent such as n-butyl lithium (n-BuLi) followed by quenching with an atmosphere of dry carbon dioxide ($CO_2$) furnishes alkynoic acids of formula 38. These may be converted to mixed anhydrides of Formula 40 using a reagent such as isobutylchloroformate in an inert solvent such as tetrahydrofuran in the presence of a base such as N-methylmoipholine. These anhydrides may then be used to prepare the compounds of this invention as described in the above flowsheets.

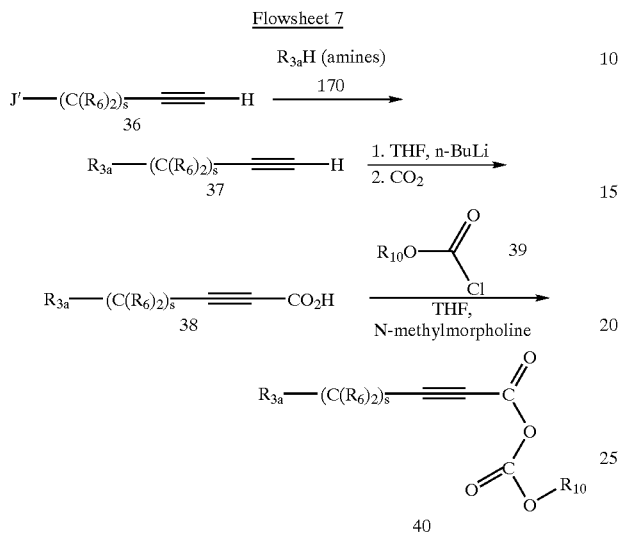

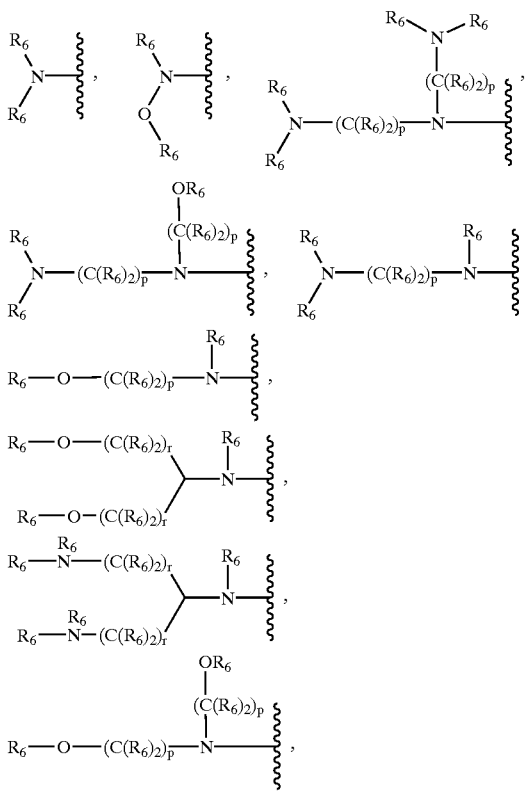

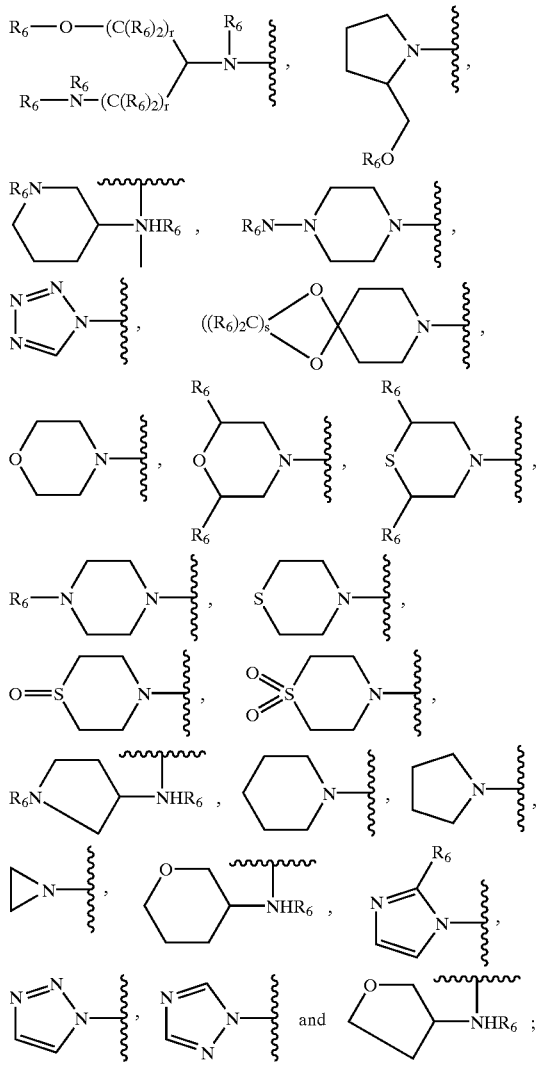

In order to prepare some of the compounds of this invention certain alcohols, and mixed anhydrides are required; these are prepared as outlined below in Flowsheet 7a wherein $R_3a$, $R_6$, $R_{10}$, J', and s are as defined above with alcohols 171, $R_{3a}H$. Reaction of alcohols 171, $R_{3a}H$ with alkynes 36 is accomplished using sodium hydride in an inert solvent such as tetrahydrofuran (THF), or other non-nucleophic base such as potassium or cesium carbonate in an inert solvent such as tetrahydrofuran, acetone, or N,N-dimethylformamide to yield alkoxyalkynes 41. In some cases, the alcohol $R_{3a}H$ may also be the solvent of the reaction. Some representative $R_{3a}$— moieties of alcohols 171, $R_{3a}H$ are shown below in List B wherein $R_6$, p, and r are as defined above. The alcohols 171, $R_{3a}H$ are available commercially, are known in the chemical literature, or may be prepared by simple procedures that are well known in the art. In some cases, these alcohols may have one or more asymmetric carbon atoms; they may be used as the Eracemate or they may be resolved and used as the individual R or S entantiomers in which case the compounds of this invention will be in the racemic or optically active forms, respectively. Treatment of alkoxyalkynes 41 with an alkyl lithium reagent such as n-butyl lithium (n-BuLi) followed by quenching with an atmosphere of dry carbon dioxide furnishes the carboxylic acids of formula 42. These may be converted to mixed anhydrides of formula 43 using a reagent such as isobutylchloroformate in an inert solvent such as tetrahydroftiran in the presence of a base such as N-methylmoipholine. These anhydrides may then be used to prepare the compounds of this invention as described in the above flowsheets.

Flowsheet 7a

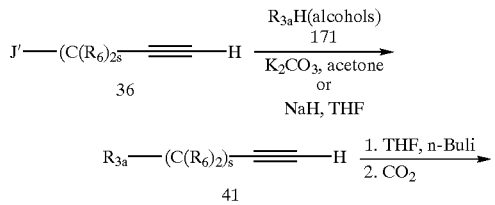

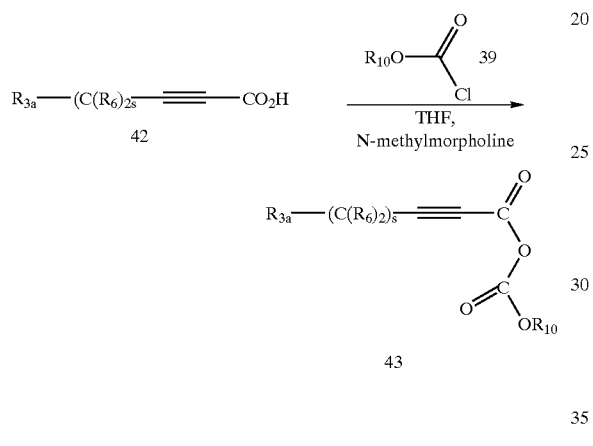

$R_{3a}$— (Representative Moieties) of Alcohols 171, $R_{3a}H$

List B

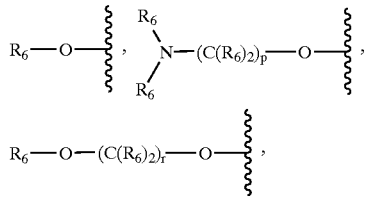

As outlined in Flowsheet 8 below wherein $G_1$, $G_2$, $G_3$, $G_4$, $R_6$, $R_{10}$, X, Z, n, and s are as defined above, alcohols 44 may be protected with, for example, a t-butyl dimethysilyl protecting group by reaction with the respective silyl chloride in methylene chloride ($CH_2Cl_2$) in the presence of triethylamine and 4-N,N-dimethylamino pyridine (DMAP). The resulting protected alcohols, 45, may be converted to the acetylenic Grignard reagents which, in turn, are maintained under an atmosphere of dry carbon dioxide to give the carboxylic acids 46. As described above the carboxylic acids 46 may be converted to the mixed anhydrides 48 which on reaction with the 2,3-dihydro-1H-[1,4]oxazino[3,2-g] quinoline-8-carbonitiiles 29 gives the corresponding amides 50. In the final step of the sequence, the silyl protecting group is removed by treating with acid in a protic solvent mixture to give 1-substituted-2,3-dihydro-1H-[1,4]oxazino [3,2-g]quinoline-8-carbonitriles represented by Formula 51.

Flowsheet 8

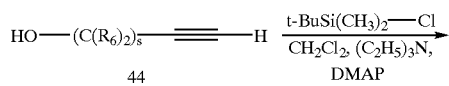

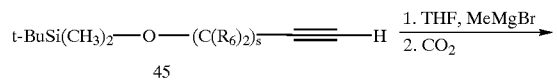

-continued
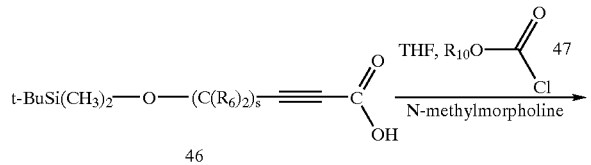
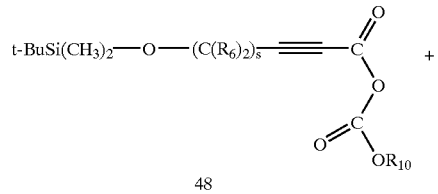
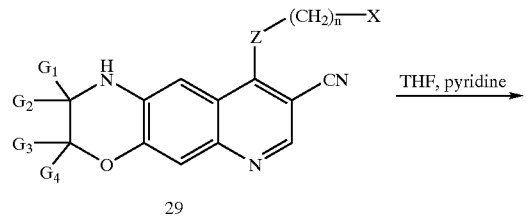
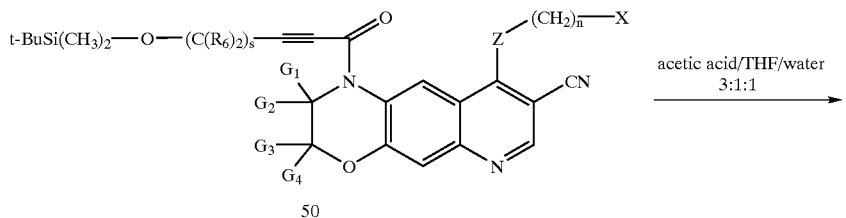
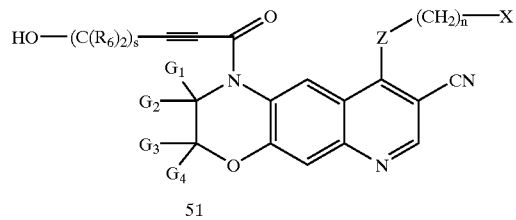
In the same manner as flowvsheet 8 the corresponding 4-substituted-3,4-dihydro-2H-[1,4]oxazino[2,3-g] quinoline-8-carbonities 52 may be prepared as shown in Flowsheet 8a.
Flowsheet 8a
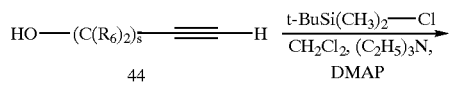
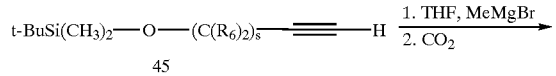
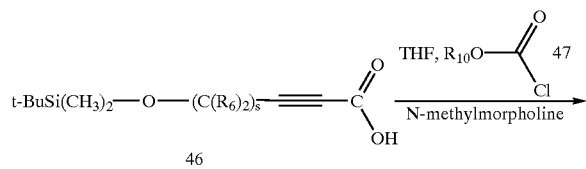

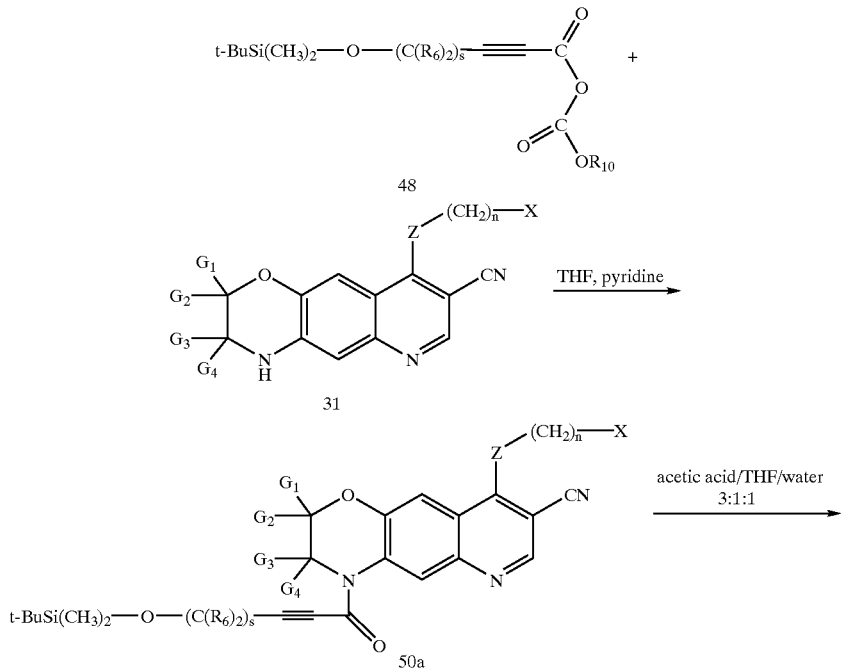

Compounds of this invention are also prepared as shown below in Flowsheet 9 wherein $R_{3a}$, $G_1$, $G_2$, $G_3$, $G_4$, $R_6$, $R_{10}$, J', X, Z, n, and s are as defined above with the proviso that $R_{3a}H$ is an amine 170 or an alcohol 171. Treatment of substituted alkynes 53 with an alkyl lithium reagent at low temperature followed by quenching with an atmosphere of dry carbon dioxide furnishes the carboxylic acids of formula 54. These may be converted to mixed anhydrides of Formula 55 using a reagent such as isobutylchloroformate in an inert solvent such as tetrahydrofuran (THF) in the presence of a base such as N-methylmorpholine. These anhydrides may then be used to prepare the compounds of this invention by the reaction with 2,3-dihydro-1H-[1,4]oxazino[3,2-g]quinoline-8-carbonitriles of Formula 29 described in the Flowsheets above. The reaction of the alcohols 171, $R_{3a}H$ and amides 57 is accomplished using sodium hydride or other non-nucleophic base in an inert solvent such as tetrahydrofuran or N,N-dimethylformamide to give 1-substituted-2,3-dihydro-1H-[1,4]oxazino[3,2-g]quinoline-8-carbonittiles of this invention represented by ethers 58. In some cases, the alcohol 171, $R_{3a}H$ may also be the solvent of the reaction. Representative $R_{3a}$— moieties of alcohols are shown in List B. The reaction of amides 57 with an amine 170, $R_{3a}H$ gives 1-substituted-2,3-dihydro-1H-[1,4]oxazino[3,2-g]quinoline-8-carbonitriles of this invention represented by amines 59 is accomplished by heating in an inert solvent such as tetrahydrofuran or N,N-dimethylfoiamide, or using potassium or cesium carbonate in acetone. The temperature and duration of the heating will depend on the reactivity of amides 57; longer reaction times and higher temperatures may be required when s is greater than 1.

Flowsheet 9

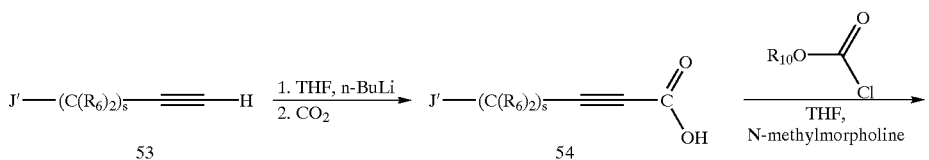

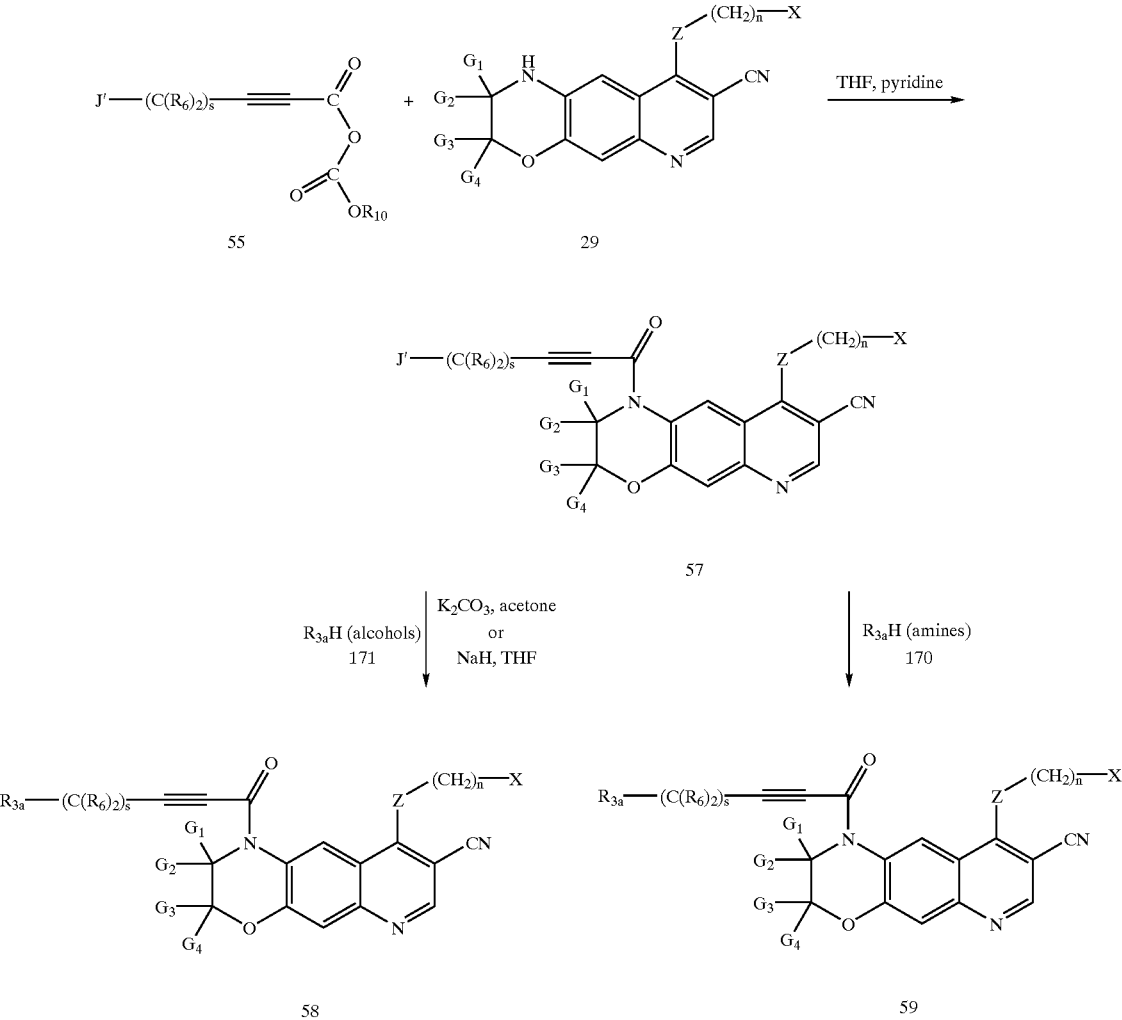
Using methods similar to that summarized above in Flowsheet 9 the corresponding 4-substituted-3,4-dihydro-2H1-[1,4]oxazino[2,3-g]quinoline-8-carbonitriles represented by ethers 60 and amines 61 may be prepared as shown in Flowsheet 9a.
Flowsheet 9a
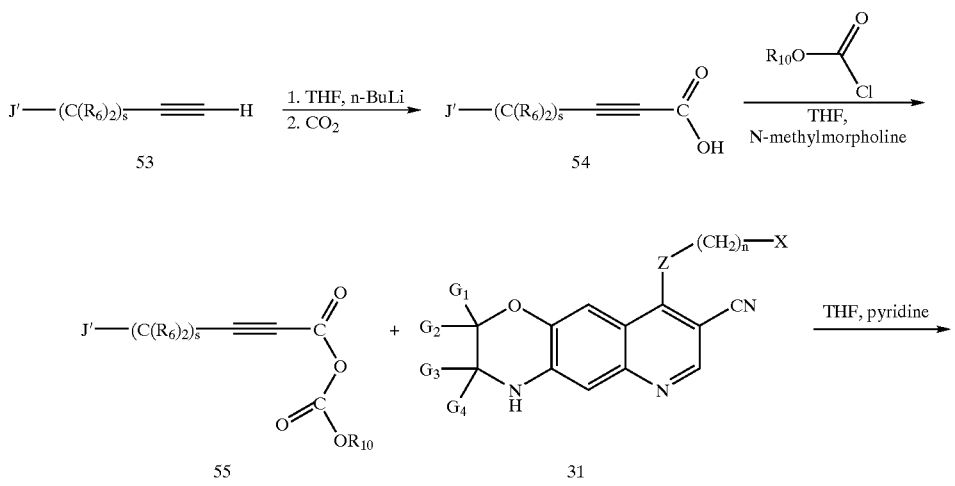

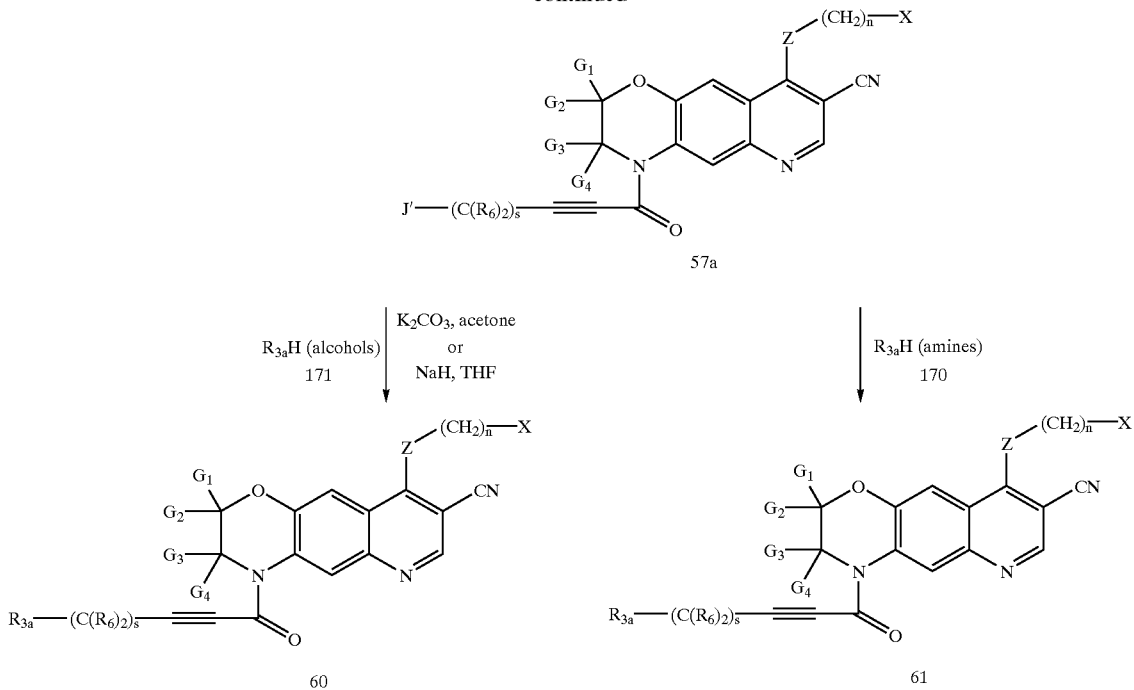

Other carboxylic acid chlorides and anhydrides needed to prepare some of the compounds of this invention may be prepared as shown below in Flowsheet 10, 10a, and 10b wherein $R_3a$, $R_6$, $R_3$, $R_{10}$, Z, Q', J', and s are as defined above. The esters 62, 66, or 71 may be hydrolyzed with a base such as barium hydroxide [$Ba(OH)_2$] to give the respective carboxylic acid 63, 67, or 72. These acids may be converted to the respective carboxylic acid chlorides 64 or 69 by using oxalyl chloride and catalytic N,N-dimethylformamide in an inert solvent or respective mixed anhydrides 68 or 73 by using isobutyl chloroformate and an organic base such as N-methylmorpholine. The leaving group J' in esters represented by Formula 65 and 70 may be displaced by the amines 170, $R_{3a}H$ or the alcohols 171, $R_{3a}H$ by using procedures previously described to give intermediate ethers 66 and amines 71, respectively. Representative $R_{3a}$— moieties of amines 170 and alcohols 171 are shown in List A and List B above wherein $R_6$, p, and r are as defined above. The carboxylic acid chlorides 64 and 69 and the anhydrides 68 and 73 may be used to prepare some of the compounds of this invention by using the methods outlined herein above in the Flowsheets.

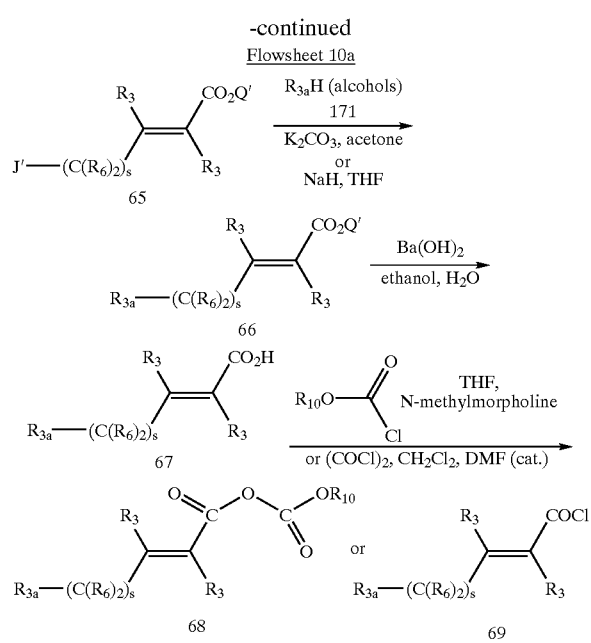

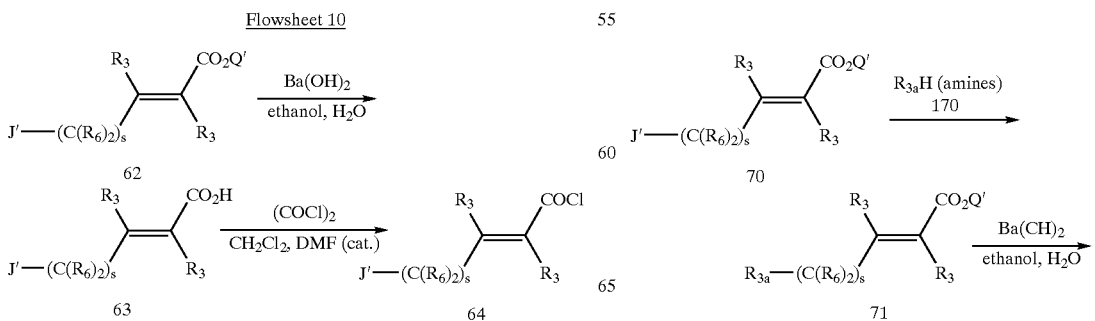

-continued

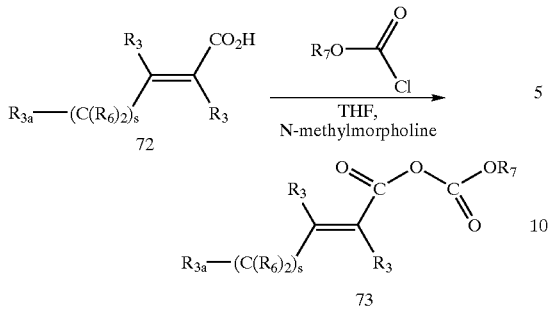

By using the methods identical to those outlined above in Flowsheet 10, 10a and 10b, it is possible to prepare the analogous carboxylic acid chlorides and anhydrides given below in List C wherein $R_3a$, $R_6$, $R_3$, p, and s are as previously defined with the proviso that $R_{3a}$ is J', an amine 170 or an alcohol 171 where $R_{10}$ is hereinbefore defined and G is the radical:

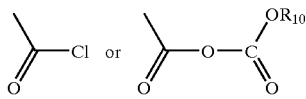

By making use of these carboxylic acid chlorides and anhydrides, by following the methods summarized in the above Flowsheets, compounds of this invention may be prepared.

LIST C

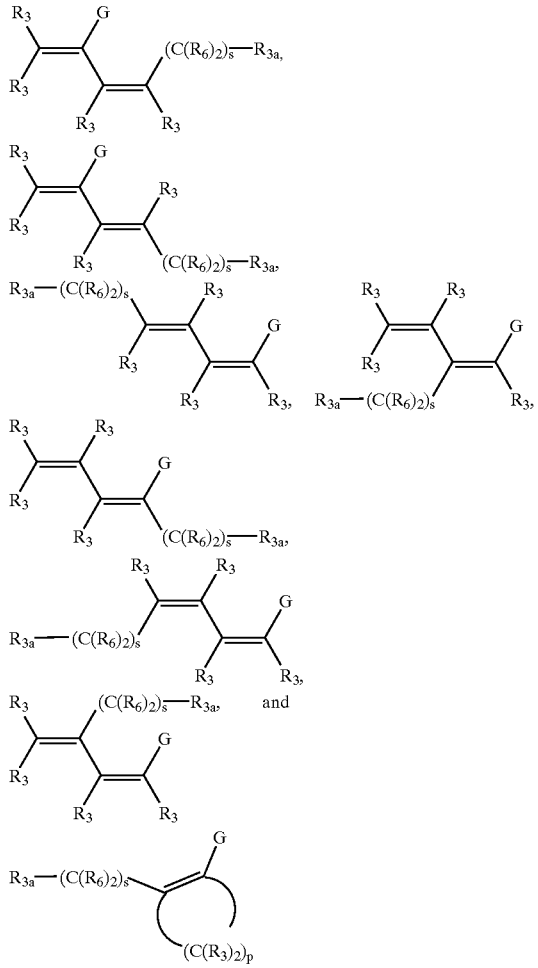

Tricyclic compounds of this invention represented by Formulas 77–78 may be prepared as shown in Flowsheet 11 wherein $R_{3a}$, $G_1$, $G_2$, $G_3$, $G_4$, $R_6$, X, Z, J', n, and s are as defined above. The reaction of the carboxylic acid chlorides 74 and 2,3-dihydro-1H-[1,4]oxazino[3,2-g]quinoline-8-carbonitriles 29 using an organic base in an inert solvent gives 1-substituted-2,3-dihydro-1H-[1,4]oxazino[3,2-g] quinoline-8-carbonitriles of this invention represented by Formula 76. The reaction of the tricyclic compounds 76 with an alcohol 171, $R_{3a}H$ is accomplished using sodium hydride or other non-nucleophic base such as potassium or cesium carbonate in an inert solvent such as tetrahydrofuran, acetone, or N,N-dimethylformamide to give 1-substituted-2,3-dihydro-1H-[1,4]oxazino[3,2-g]quinoline-8-carbonitrile of this invention represented by ethers 77. In some cases, the alcohol 171 $R_{3a}H$ may also be the solvent of the reaction. The reaction of tricyclic compounds 76 with an amine 170, $R_{3a}H$ to give 1-substituted-2,3-dihydro-1H-[1,4]oxazino[3, 2-g]quinoline-8-carbonitrile of this invention represented by amines 78 is accomplished by heating in an inert solvent such as tetrahydrofuran or N,N-dimethylformamide. Some representative $R_{3a}$— moieties of amines are shown in List A above and some representative $R_{3a}$— moieties of alcohols are shown in List B. The temperature and duration of the heating will depend on the reactivity of the tricyclic compounds 76; longer reaction times and higher temperatures may be required when s is greater than 1. In addition, by using this method, the carboxylic acid chlorides and mixed anhydrides listed in List C may be used to prepare the analogous compounds of this invention.

Flowsheet 11
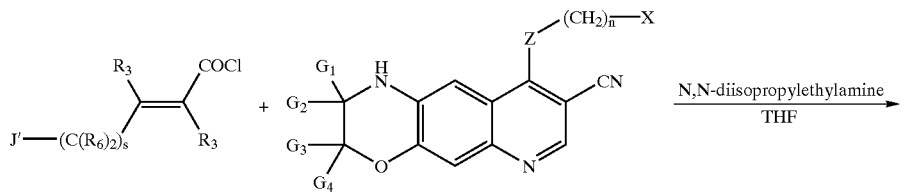
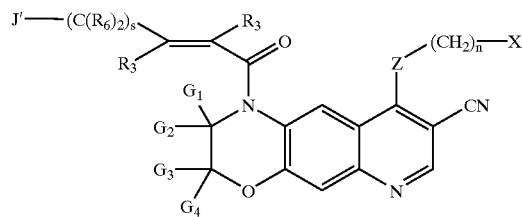
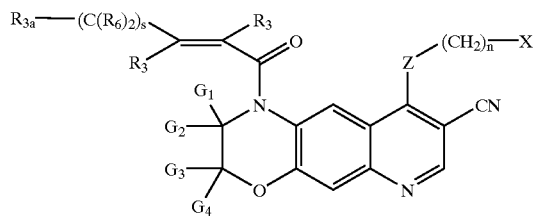 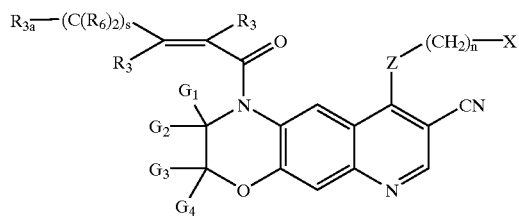
By applying the methods summarized above, the corresponding 4-substituted-3,4-dihydro-2H-[1,4]oxazino[2,3-g]quinoline-8-carbonitriles represented by ethers 79 and amines 80 may be prepared as shown in Flowsheet 11a.
Flowsheet 11a
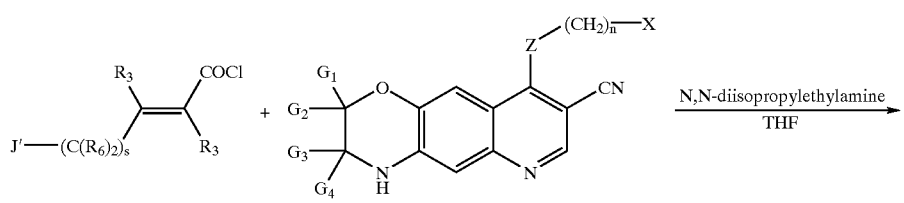

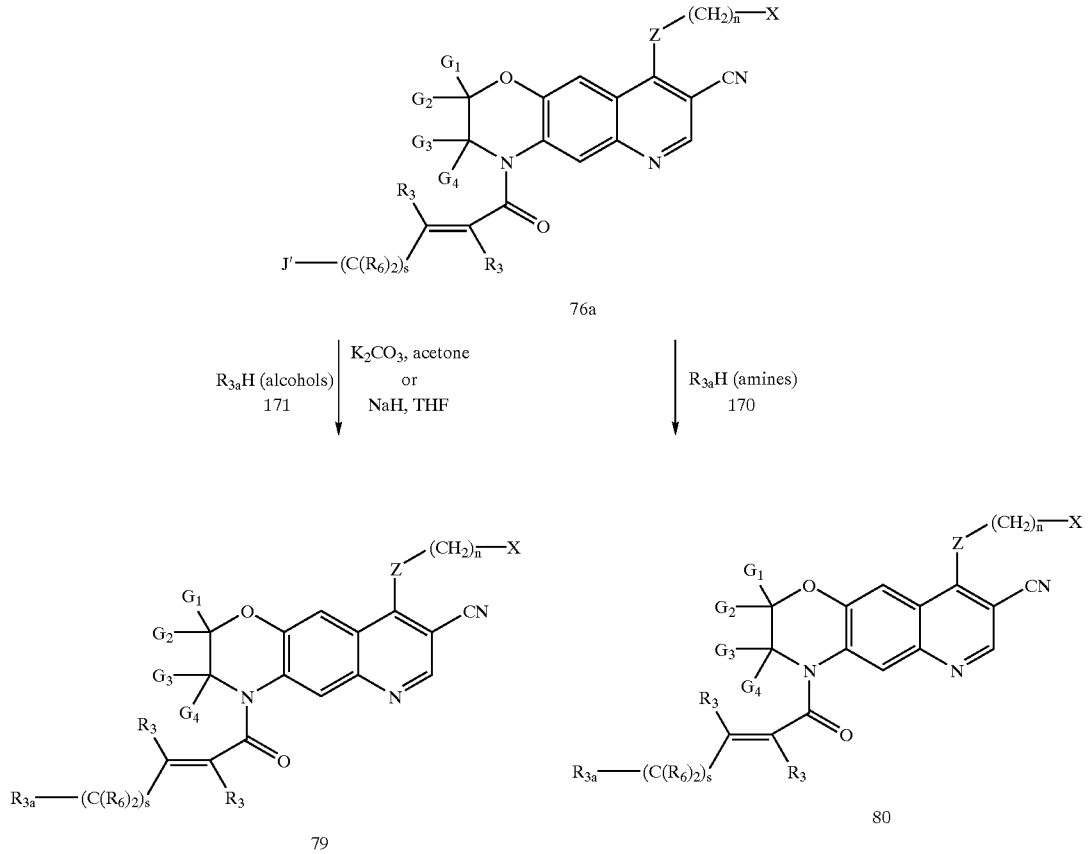

The reaction of 1-substituted-2,3-dihydro-1H-[1,4]oxazino[3,2-g]quinoline-8-carbonitriles 76 with nitrogen containing heterocycles represented by Formula 81 which also contains an unsaturated carbon-nitrogen bond is accomplished by refluxing in an inert solvent and gives the 1-substituted-2,3-dihydro-1H-[1,4]oxazino[3,2-g]quinoline-8-carbonitriles 82 of this invention where the compounds bear a positive charge as shown in Flowsheet 11b. The counter anion J' may be replaced with any other pharmaceutically acceptable anion using the appropriate ion exchange resin. The corresponding 4-substituted-3,4-dihydro-2H-[1,4]oxazino[2,3-g]quinoline-8-carbonitriles 82a may be prepared in an analogous manner.

Flowsheet 11b

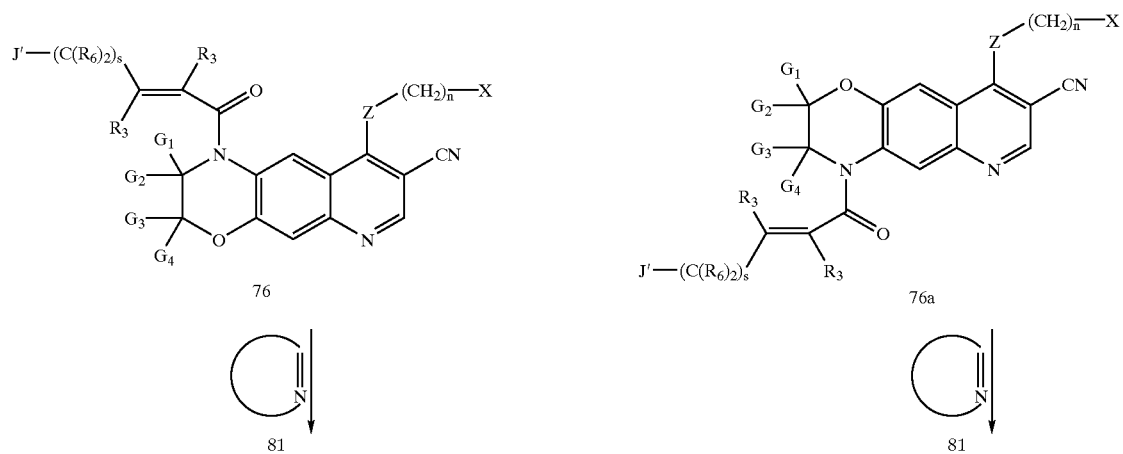

-continued

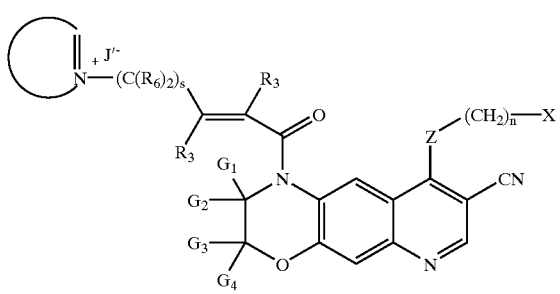

82

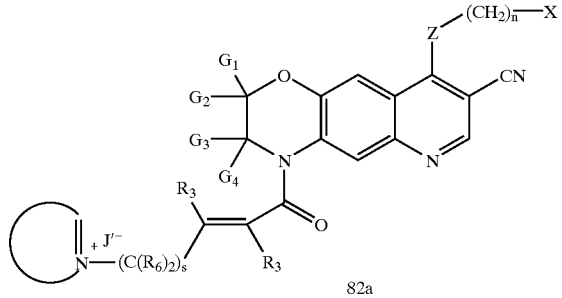

82a

Some of the compounds of this invention may be prepared as outline below in Flowsheet 12 wherein $G_1$, $G_2$, $G_3$, $G_4$, $R_6$, $R_{10}$, X, Z, J', p, n, and s are as defined above. The substituted acetylenic alcohols 83 may be coupled to the halides, mesylates, or tosylates 84 using a base such as sodium hydride in an inert solvent such as tetrahydrofuran. The resulting acetylene, 85, may then be treated with an alkyl lithium reagent at low temperature. Maintaining the reaction under an atmosphere of carbon dioxide then gives the carboxylic acids 86. These, in turn, are reacted with the 2,3-dihydro-1H-[1,4]oxazino[3,2-g]quinoline-8-carbonitriles 29, via the mixed anhydrides to give the tricyclic amide of this invention represented by Formula 88. Alternatively, the acetylene intermediates 85 may be prepared starting with an alcohol 89 by first treating with a base such as sodium hydride in an inert solvent such as tetrahydrofuran and then adding an acetylene 90 having an appropriate leaving group J' wherein J', p and s are hereinbefore defined.

Flowsheet 12

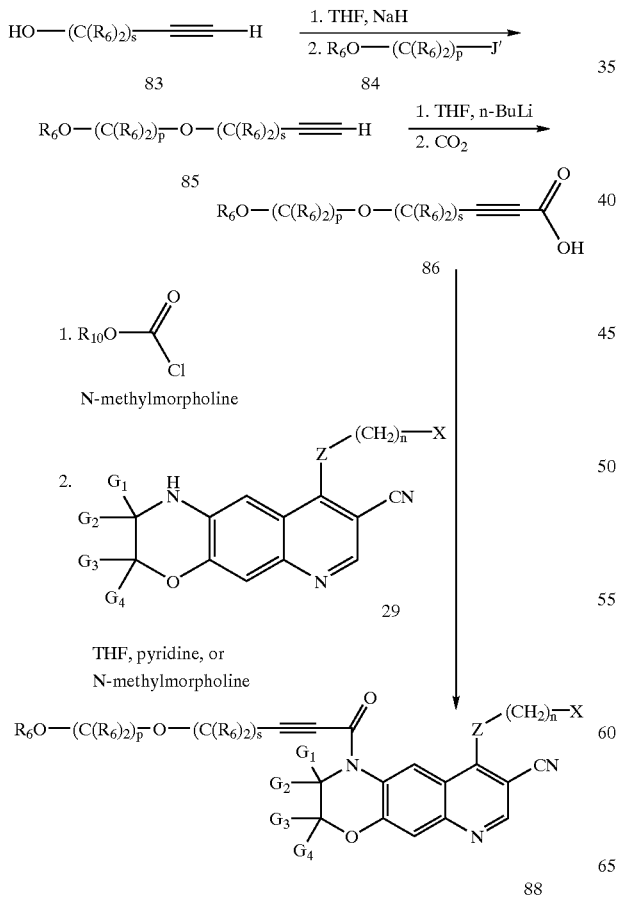

In a similar manner, as shown in Flowsheet 12, the amino alcohols represented by the formula 89a: $(R_6)_2N\text{---}(C(R_6)_2)_p\text{---}OH$ may be reacted with acetylenes 90 and subsequently converted to the 1-substituted-2,3-dihydro-1H-[1,4]oxazino[3,2-g]quinoline-8-carbonitriles of this invention represented by the formula 88a as shown in Flowsheet 12a.

Flowsheet 12a

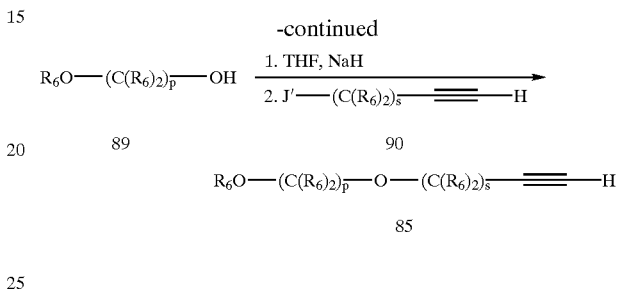

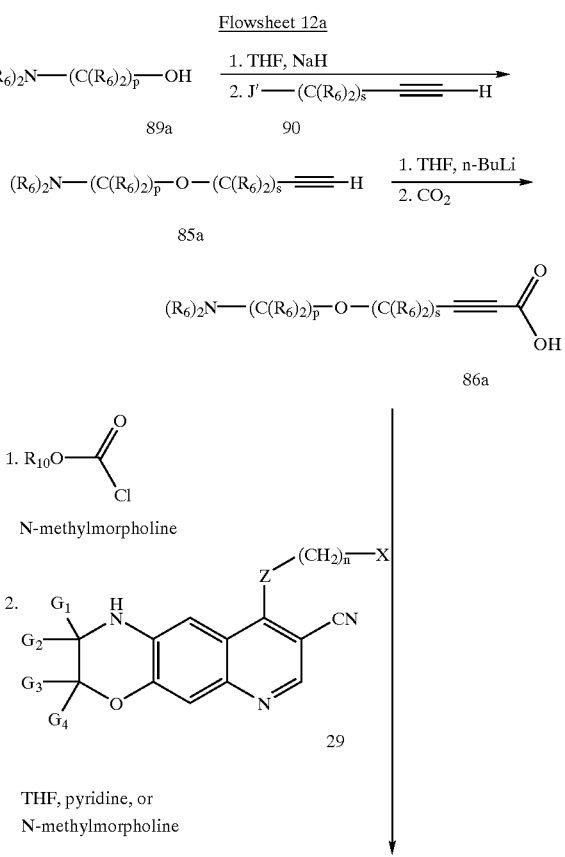

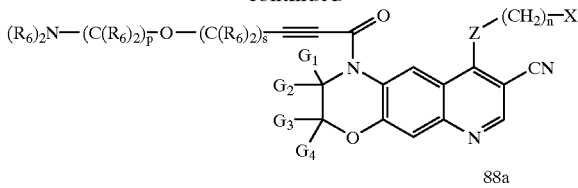

In an entirely analogous manner to Flowsheet 12, the corresponding 4-substituted-3,4-dihydro-2H-[1,4]oxazino[2,3-g]quinoline-8-carbonitriles 92 are prepared as shown in Flowsheet 12b.

3-g]quinoline-8-carbonitriles of this invention represented by the formula 92a as shown in Flowsheet 12c.

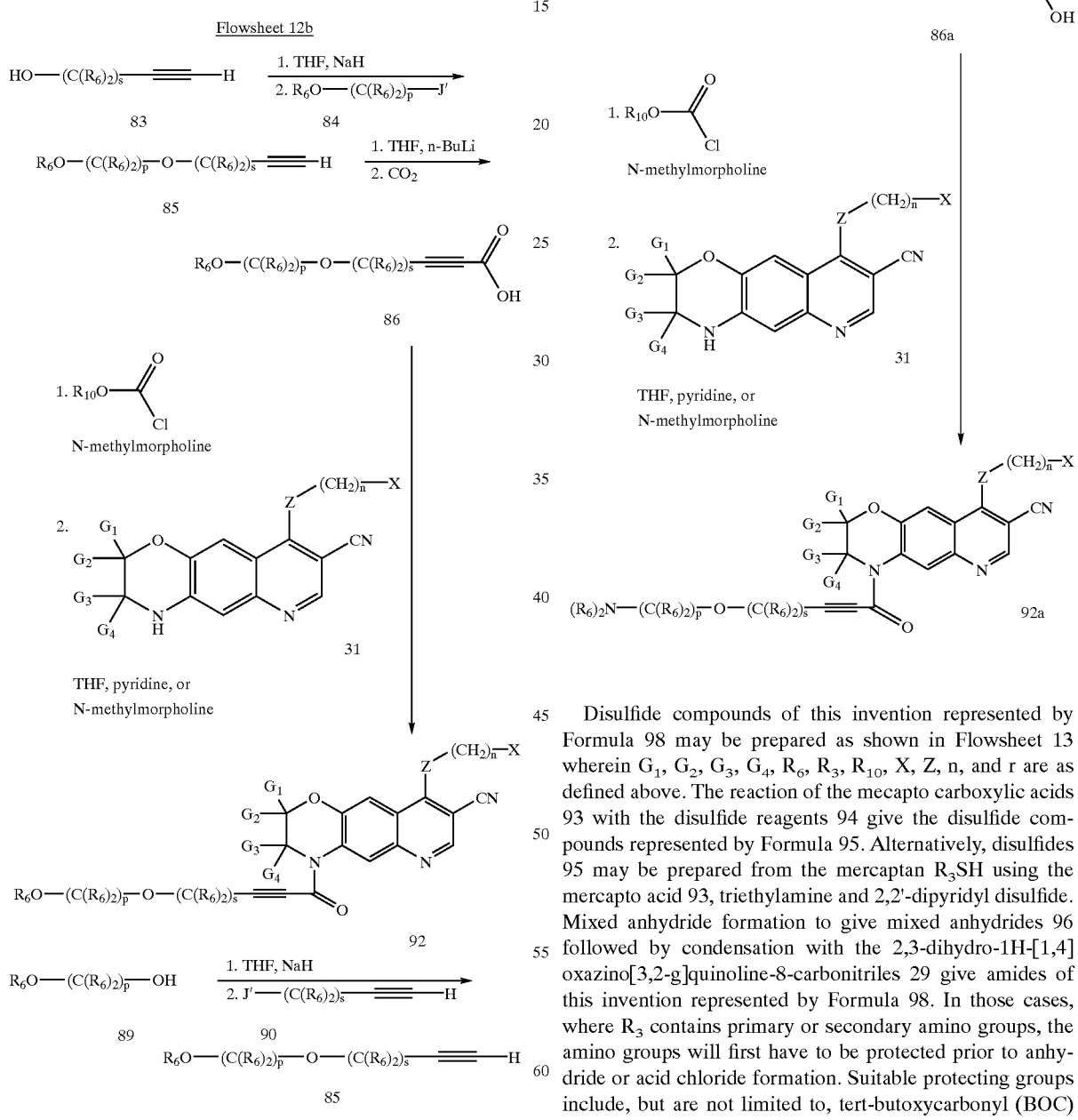

Disulfide compounds of this invention represented by Formula 98 may be prepared as shown in Flowsheet 13 wherein $G_1$, $G_2$, $G_3$, $G_4$, $R_6$, $R_3$, $R_{10}$, X, Z, n, and r are as defined above. The reaction of the mecapto carboxylic acids 93 with the disulfide reagents 94 give the disulfide compounds represented by Formula 95. Alternatively, disulfides 95 may be prepared from the mercaptan $R_3SH$ using the mercapto acid 93, triethylamine and 2,2'-dipyridyl disulfide. Mixed anhydride formation to give mixed anhydrides 96 followed by condensation with the 2,3-dihydro-1H-[1,4]oxazino[3,2-g]quinoline-8-carbonitriles 29 give amides of this invention represented by Formula 98. In those cases, where $R_3$ contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The BOC protecting group may be removed from the final products by treatment with an acid such as trifluoroactic acid (TFA) while the CBZ protecting group may be removed by catalytic hydrogenation.

In a similar manner, to Flowsheet 12a, the amino alcohols represented by the formula 91: $(R_6)_2N$—$(C(R_6)_2)_p$—OH may be reacted with acetylene 90 and subsequently converted to the 4-substituted-3,4-dihydro-2H-[1,4]oxazino[2,

Flowsheet 13

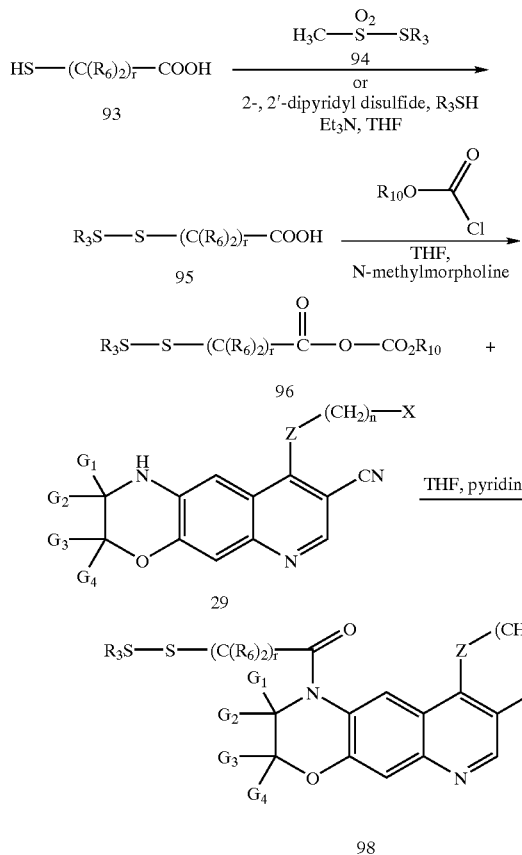

Flowsheet 13a

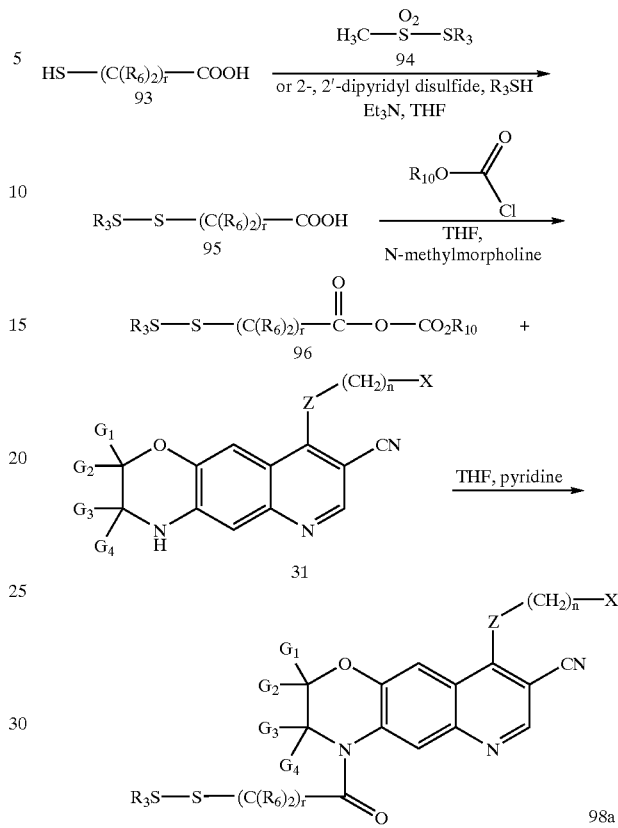

In an entirely analogous manner to Flowsheet 13, the corresponding 4-substituted-3,4-dihydro-2H-[1,4]oxazino[2,3-g]quinoline-8-carbonitriles 98a are prepared as shown in Flowsheet 13b. In those cases where $R_3$ contains hydroxyl groups, the hydroxyl groups may have to be protected prior to treatment with an anhydride or acid chloride. Suitable protecting groups include, but are not limited to, t-butyldimethylsilyl, tetrahydropyranyl, or benzyl protecting groups. t-Butyldimethylsilyl and tetrahydropyranyl protecting groups may be removed from the final products by treatment with an acid such as acetic acid or hydrochloric acid while the benzyl protecting group may be removed by catalytic hydrogenation.

Compounds of this invention represented by Formulas 101–103 may be prepared as shown in Flowsheet 14 wherein Q, $G_1$, $G_2$, $G_3$, $G_4$, $R_5$, J', X, Z, and n are as defined above. Alkylation of 2,3-dihydro-1H-[1,4]oxazino[3,2-g]quinoline-8-carbonitriles 29 with formula 99 may be accomplished by heating in an inert solvent such as N,N-dimethylformamide using a base such as potassium carbonate to give 1-substituted-2,3-dihydro-1H-[1,4]oxazino[3,2-g]quinoline-8-carbonitriles of this invention represented by the Formula 101. When Q is alkoxy, the ester group may be hydrolyzed to an acid using a base such as sodium hydroxide in methanol. In a similar manner, by using intermediates 104 and 105, 1-substituted-2,3-dihydro-1H-[1,4]oxazino[3,2-g]quinoline-8-carbonitriles of this invention represented by Formulas 102 and 103 respectively, may be prepared.

Flowsheet 14

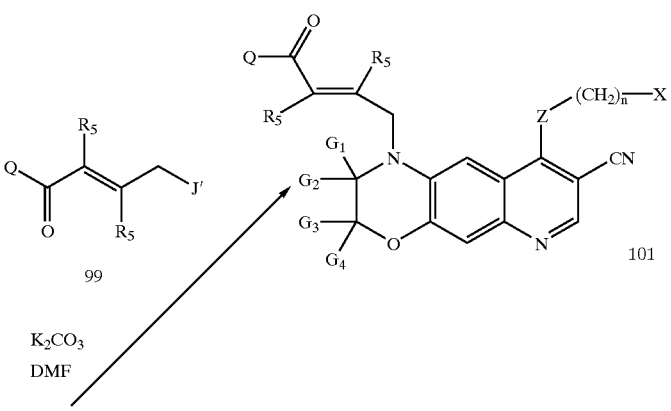

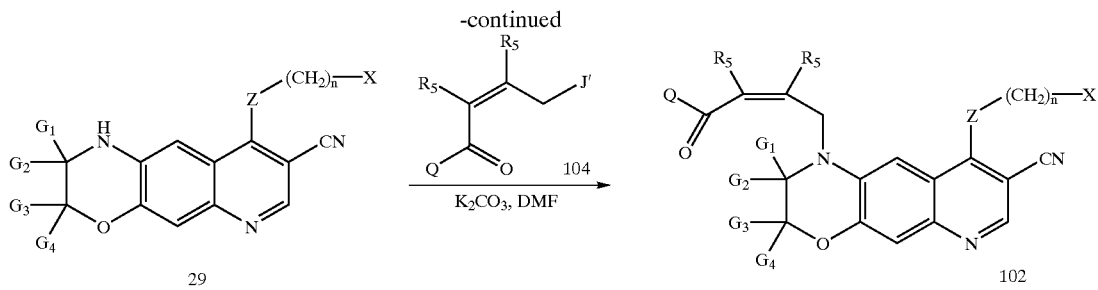
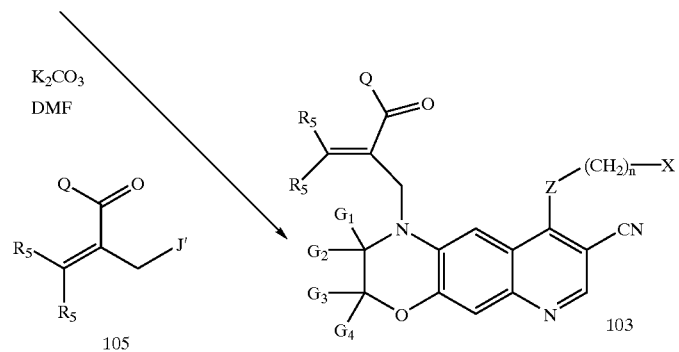
In an entirely analogous manner to Flowsheet 14, the corresponding 4-substituted-3,4-dihydro-2H-[1,4]oxazino[2,3-g]quinoline-8-carbonitriles 101a, 102a, and 103a are prepared as shown in Flowsheet 14a.
Flowsheet 14a
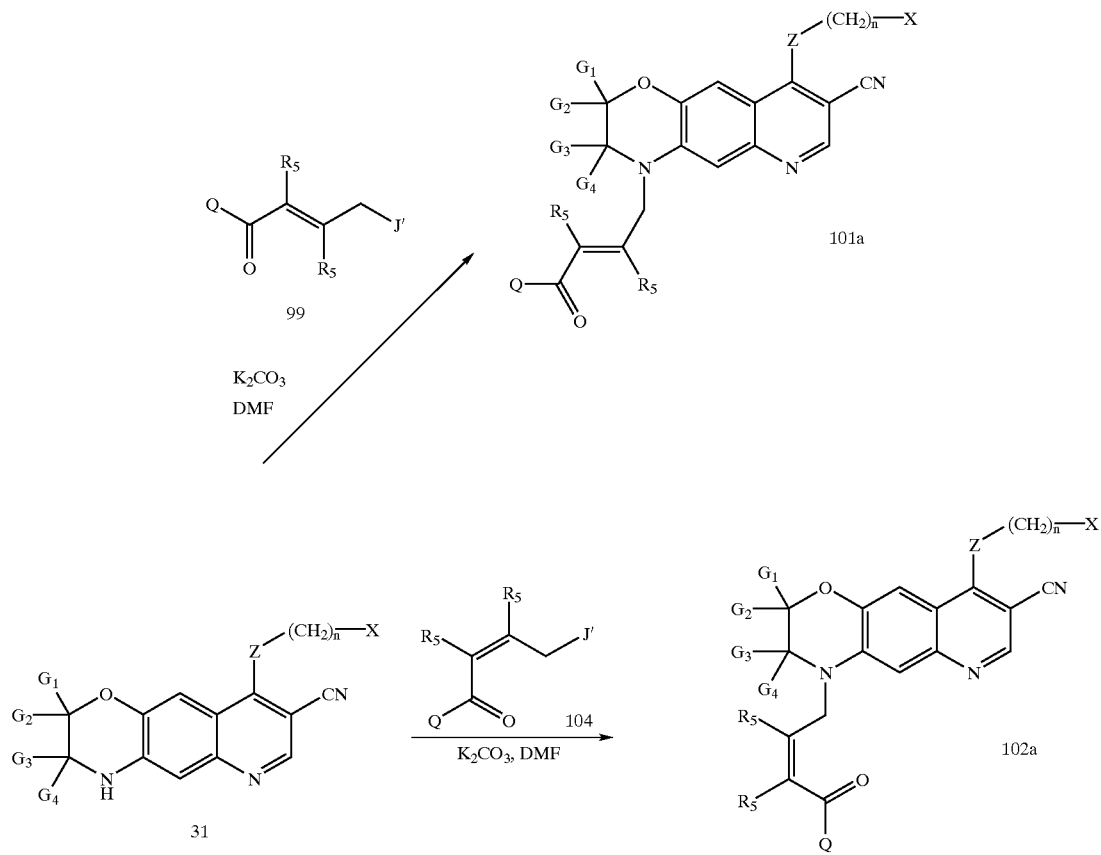

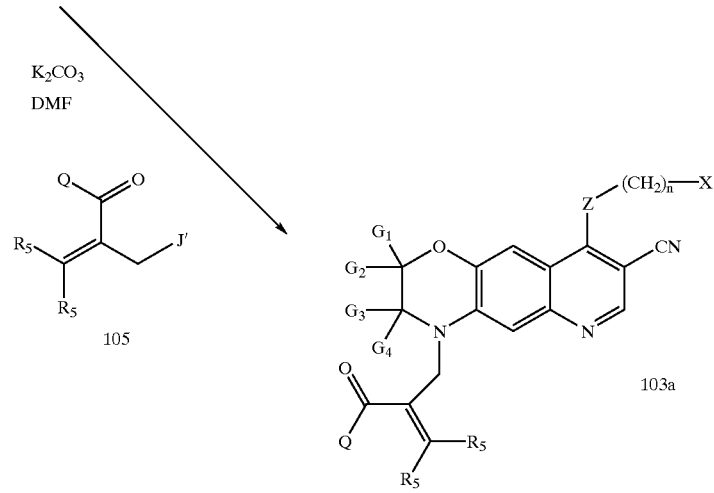

Compounds of this invention represented by Formula 108 may be prepared as shown in Flowsheet 15 wherein $G_1$, $G_2$, $G_3$, $G_4$, $R_5$, X, Z, and n are as defined above. The reaction of reagent 106 with the 2,3-dihydro-1H-[1,4]oxazino[3,2-g]quinoline-8-carbonitriles 29 is accomplished by using an excess of an organic base such as triethylamine and an inert solvent such as tetrahydrofuran to give sulfonamides of this invention represented by Formula 108.

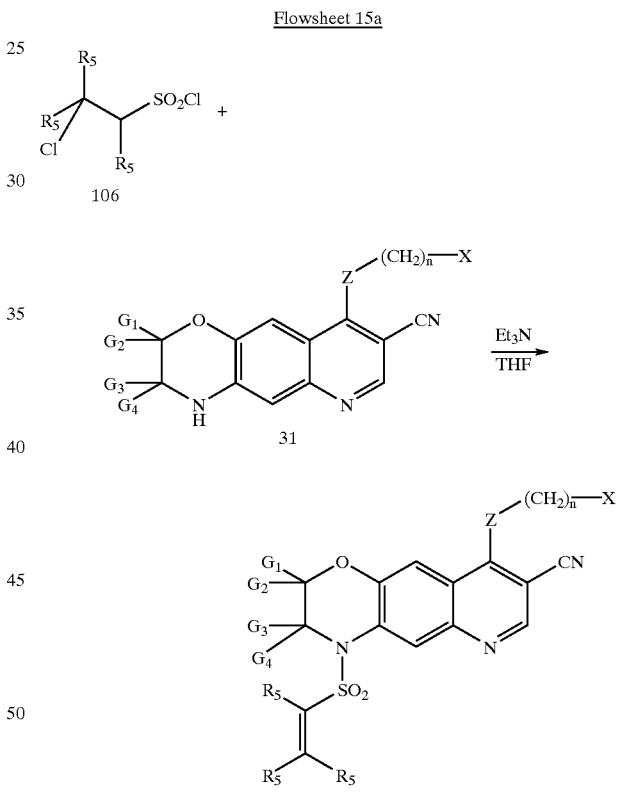

Flowsheet 15

Flowsheet 15a

In an entirely analogous manner to Flowsheet 15, the sulfonamides represented by Formula 108a are prepared as shown in Flowsheet 15a.

Compounds of this invention represented by Formula 111 may be prepared as shown in Flowsheet 16 wherein $G_1$, $G_2$, $G_3$, $G_4$, $R_{11}$, X, Z, and n are as defined above. The reaction of 2,3-dihydro-1H-[1,4]oxazino[3,2-g]quinoline-8-carbonitriles 29 and aldehydes 109 using sodium borohydride ($NaBH_4$) in N,N-dimethylformamide and trifluoroacetic acid at room temperature gives 1-substituted-2,3-dihydro-1H-[1,4]oxazino[3,2-g]quinoline-8-carbonitriles of this invention represented by 111.

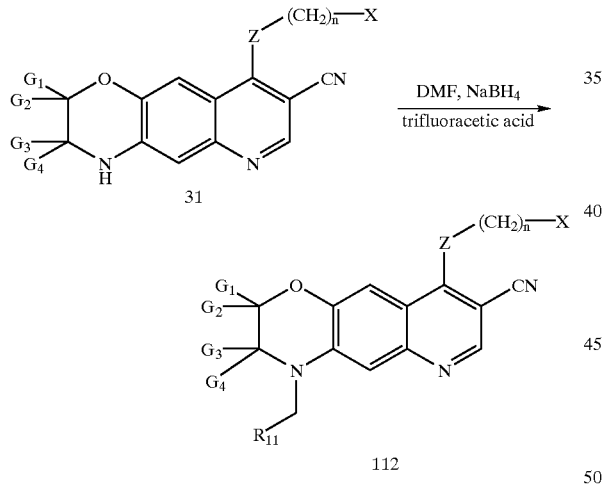

In the same manner, to Flowsheet 16, the 4-substituted-3,4-dihydro-2H-[1,4]oxazino[2,3-g]quinoline-8-carbonitriles represented by Formula 112 may be prepared as shown in Flowsheet 16a.

Compounds of this invention represented by Formula 116 and 117 may be prepared as shown in Flowsheet 17 wherein $R_{13}$, $G_1$, $G_2$, $G_3$, $G_4$, $R_6$, J', X, Z, k and n are as defined above. The reaction of 2,3-dihydro-1H-[1,4]oxazino[3,2-g]quinoline-8-carbonitriles 29 and aldehydes 113 using sodium borohydride in dimethylformamide and trifluoroacetic acid at room temperature gives the compounds of this invention represented by 115 containing a leaving group J'. Displacement of J' in 115 with an alcohol 173, $R_{13}H$ where some representative $R_{13}$— moieties of alcohols 173, $R_{13}H$ are shown in List E below, is accomplished by using sodium hydride or other non-nucleophic base in an inert solvent such as tetrahydrofuran or N,N-dimethylformamide to give ethers of this invention represented by Formula 116. In some cases, the alcohol 173, $R_{13}H$ may also be the solvent of the reaction. Displacement of the leaving group J' in 115 with an amine 172, $R_{13}H$ of List D is accomplished by heating in an inert solvent such as tetrahydrofuran or N,N-dimethylformamide, or using potassium or Cesium carbonate in acetone to give amines of this invention represented by 117.

$R_{13}$— (Representative Moieties) of Amines 172, $R_{13}H$

List D

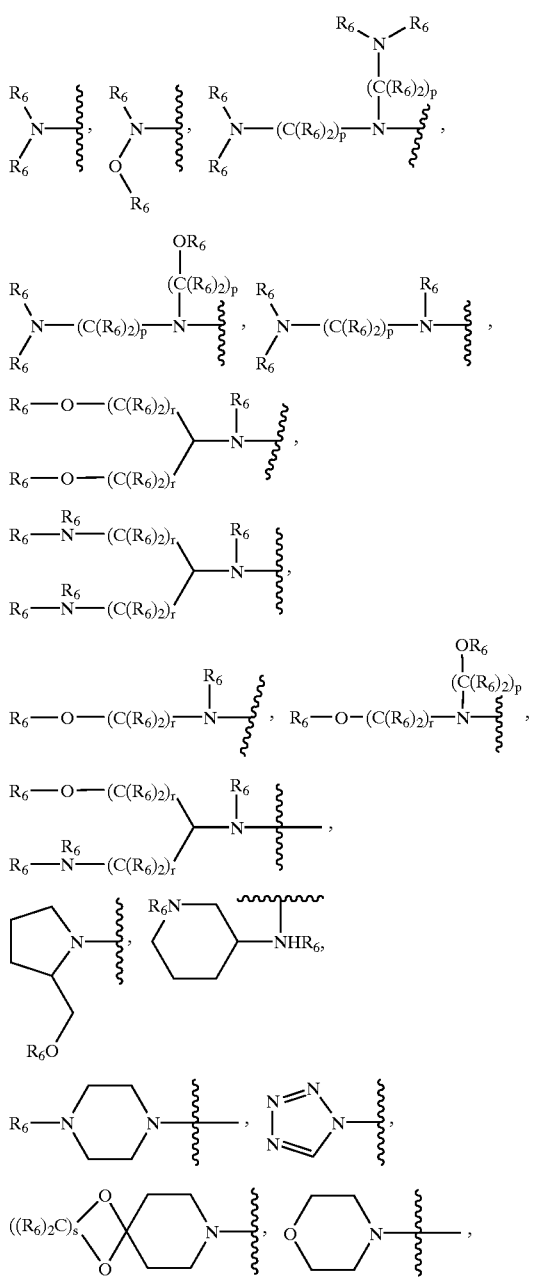

-continued
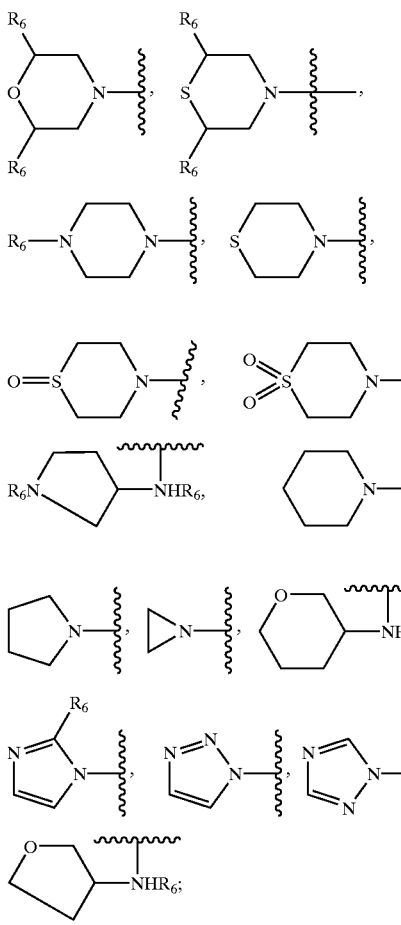
R$_{13}$a— (Representative Moieties) of Alcohols 173, R$_{13}$H
List E
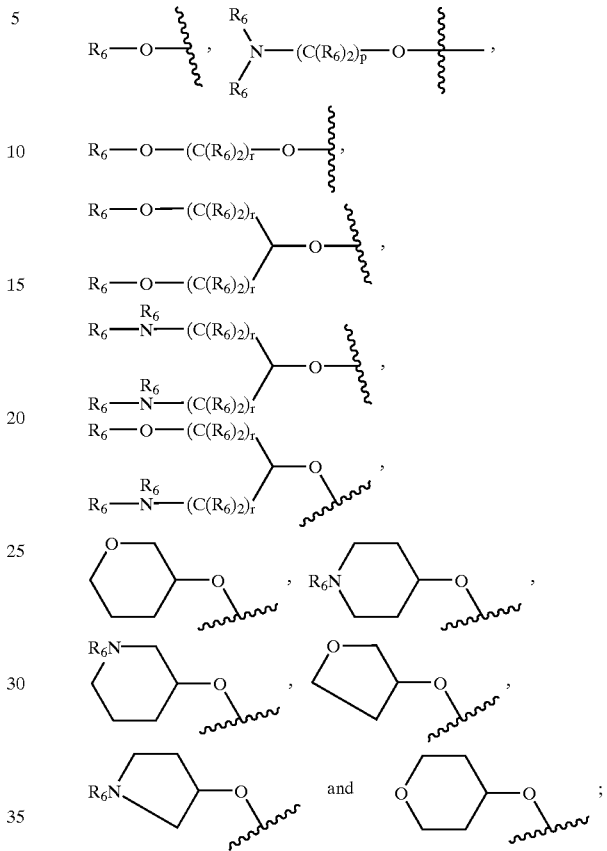
Flowsheet 17
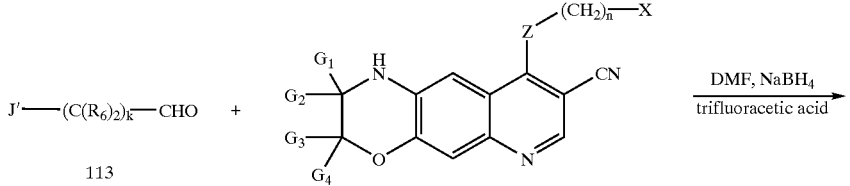
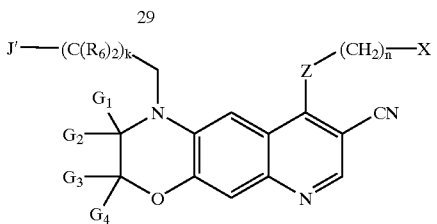

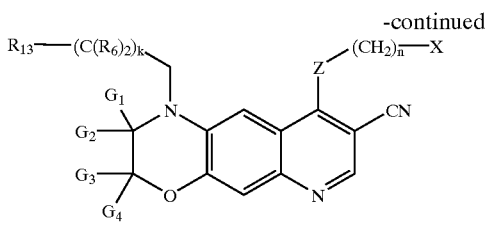 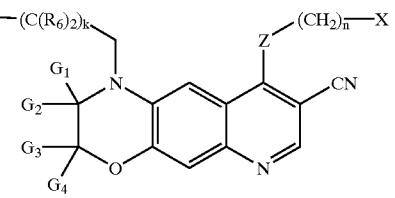
116     117
In the same manner, as shown in Flowsheet 17, the corresponding 3,4-dihydro-2H-[1,4]oxazino[2,3-g] quinoline-8-carbonitriles represented by ethers 118 and amines 119 may be prepared as shown in Flowsheet 17a.
Flowsheet 17a
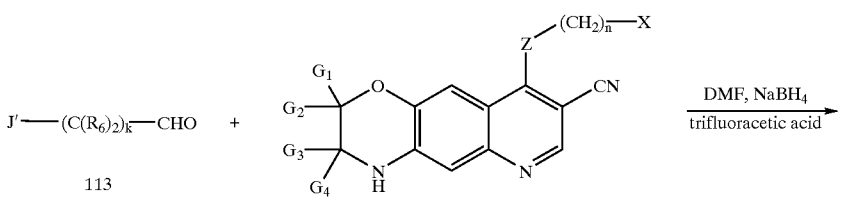
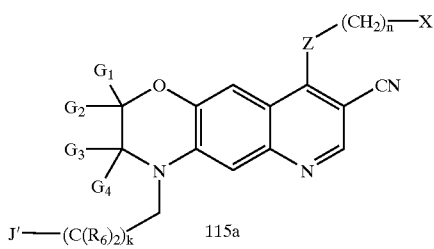
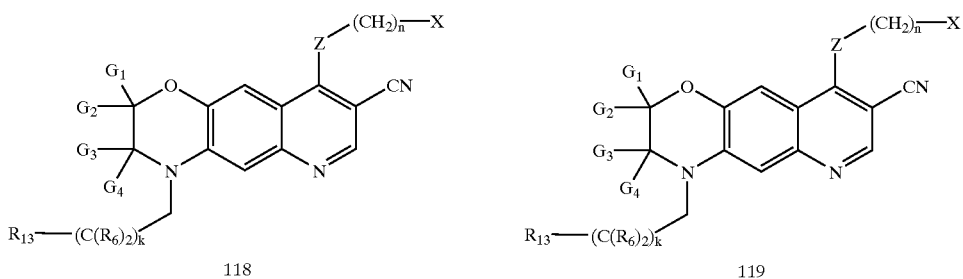

Compounds of this invention represented by Formula 122 may be prepared as shown in Flowsheet 18 wherein $R_{12}$, $G_1$, $G_2$, $G_3$, $G_4$, J', X, Z, and n are as defined above. Treatment of 2,3-dihydro-1H-[1,4]oxazino[3,2-g]quinoline-8-carbonitriles 29 with Formula 120 containing a leaving group J' in an inert solvent such as tetrahydrofuran gives 1-substituted-2,3-dihydro-1H-[1,4]oxazino[3,2-g]quinoline-8-carbonitriles of this invention represented by Formula 122.

Flowsheet 18

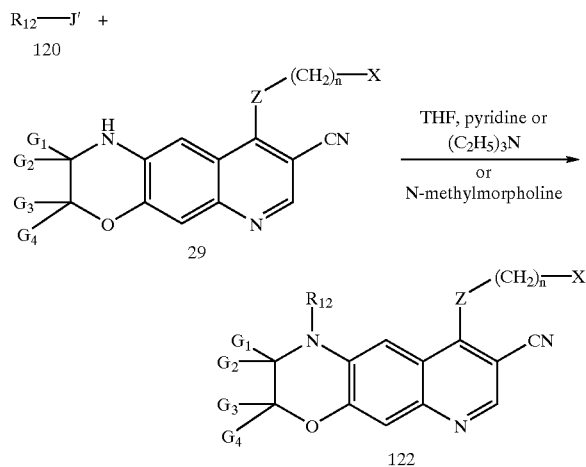

Using methods similar to that summarized above in Flowsheet 18, 4-substituted-3,4-dihydro-2H-[1,4]oxazino[2,3-g]quinoline-8-carbonitriles represented by Formula 123 may be prepared.

Flowsheet 18a

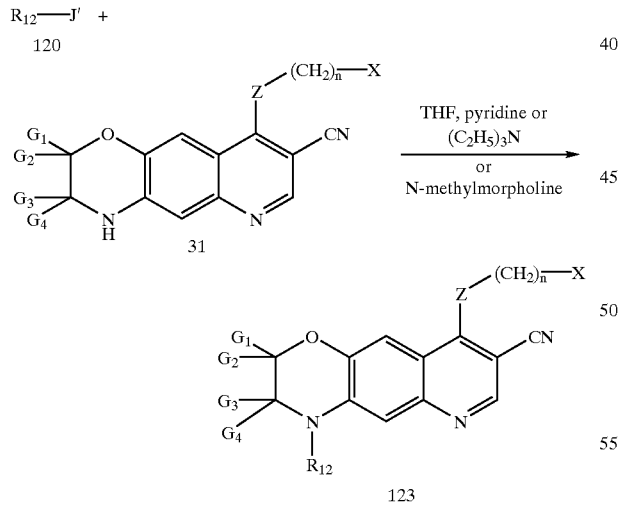

The preparation of compounds and intermediates of this invention, 4-substituted-quinoline-3-carbonitriles 130 is described below in Flowsheet 19 where X, n, and Z are as hereinbefore described. Substituted-anilines 124 which may be prepared from 3-aminothiophenol is condensed with 2-cyano-3-ethoxy-acrylic acid ethyl ester 3 by heating in the absence of solvent to give esters 125, wherein $R_{4a}$ is a thioprotecting group which is selected from benzyl, t-butyl and the like. Thermal cyclization of esters 125 in refluxing 3:1 diphenyl ether/biphenyl or diphenyl ether gives 4-oxo-1,4-dihydro-quinoline-3-carbonitriles 126, which may also exist in the 4-hydroxy-quinoline tautomeric form. Nitration of 4-oxo-1,4-dihydro-quinoline-3-carbonitriles 126 in trifluoroacetic acid (TFA) with ammonium nitrate at room temperature gives the nitro compounds 127. Nitro compounds 127 are refluxed with chlorinating reagent selected from the group consisting of phosphorous oxychloride, oxalyl chloride or phosphorous oxychloride and phosphorus pentachloride to furnish 4-chloro compounds 128. Condensation of 4-chloro compounds 7 with various amines, anilines, alcohols, phenols, mercaptans, and thiophenols of the Formula HZ—$(CH_2)_n$—X 7a where Z, X and n are hereinbefore defined gives 4-substituted-6-nitro-quinoline-3-carbonitriles 129. This condensation may be accelerated by heating the reaction mixture together with one equivalent of pyridine hydrochloride in alcohol solvents which include isopropanol and 2-ethoxyethanol or by using bases such as trialkylamines, sodium hydride in an inert solvent which includes tetrahydrofuran (THF), sodium or potassium alkoxides in alcohol solvents which includes ethanol, and the like. Reduction of 4-substituted-6-nitro-quinoline-3-carbonitriles 129 with iron and ammonium chloride in refluxing methanol and water furnishes 4-substituted-6-amino-quinoline-3-carbonitriles 130.

Flowsheet 19

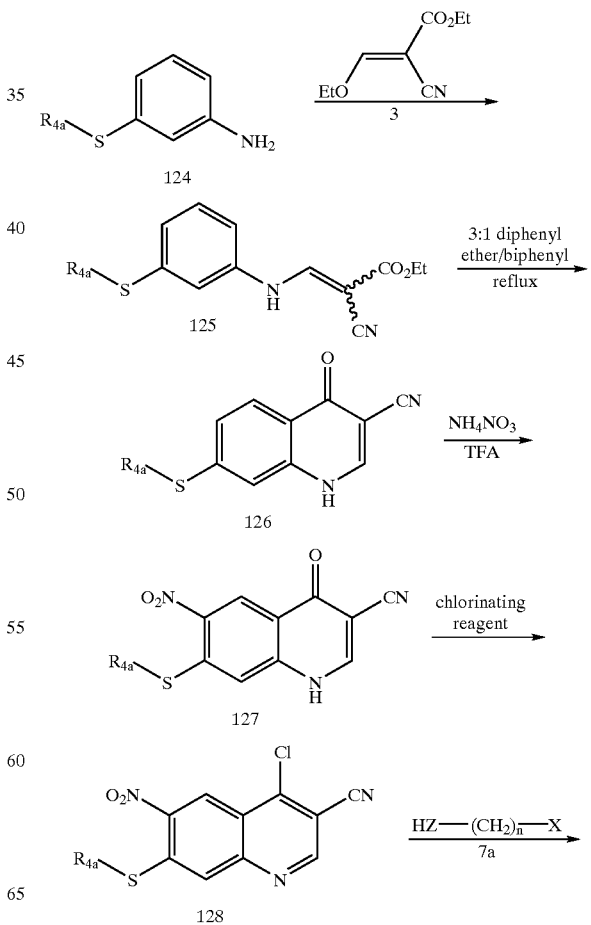

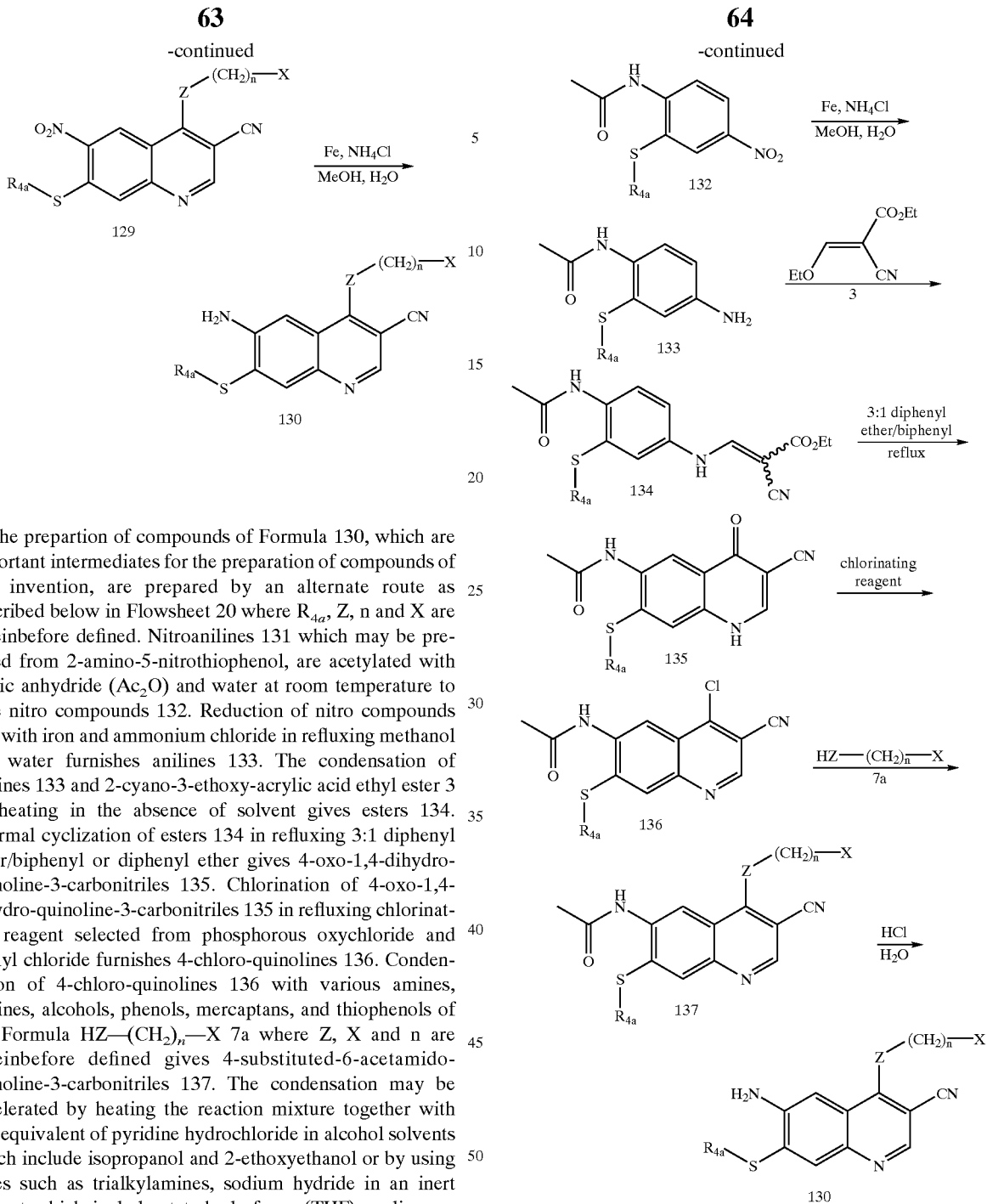

The prepartion of compounds of Formula 130, which are important intermediates for the preparation of compounds of this invention, are prepared by an alternate route as described below in Flowsheet 20 where $R_{4a}$, Z, n and X are hereinbefore defined. Nitroanilines 131 which may be prepared from 2-amino-5-nitrothiophenol, are acetylated with acetic anhydride ($Ac_2O$) and water at room temperature to give nitro compounds 132. Reduction of nitro compounds 132 with iron and ammonium chloride in refluxing methanol and water furnishes anilines 133. The condensation of anilines 133 and 2-cyano-3-ethoxy-acrylic acid ethyl ester 3 by heating in the absence of solvent gives esters 134. Thermal cyclization of esters 134 in refluxing 3:1 diphenyl ether/biphenyl or diphenyl ether gives 4-oxo-1,4-dihydro-quinoline-3-carbonitriles 135. Chlorination of 4-oxo-1,4-dihydro-quinoline-3-carbonitriles 135 in refluxing chlorinating reagent selected from phosphorous oxychloride and oxalyl chloride furnishes 4-chloro-quinolines 136. Condensation of 4-chloro-quinolines 136 with various amines, anilines, alcohols, phenols, mercaptans, and thiophenols of the Formula HZ—$(CH_2)_n$—X 7a where Z, X and n are hereinbefore defined gives 4-substituted-6-acetamido-quinoline-3-carbonitriles 137. The condensation may be accelerated by heating the reaction mixture together with one equivalent of pyridine hydrochloride in alcohol solvents which include isopropanol and 2-ethoxyethanol or by using bases such as trialkylamines, sodium hydride in an inert solvent which includes tetrahydrofuran (THF), sodium or potassium alkoxides in alcohol solvents which includes ethanol, and the like. Hydrolysis of 4-substituted-6-acetamido-quinoline-3-carbonitriles 137 in aqueous hydrochloric acid or sodium hydroxide in methanol gives 4-substituted-6-amino-quinoline-3-carbonitriles 130.

Flowsheet 20

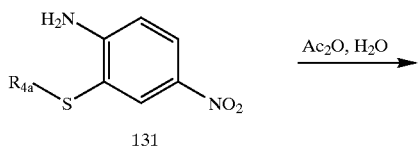

The prepartion of the compounds of this invention encompassed by compounds of Formula 145, which are important intermediates for the preparation of compounds of this invention, is described below in Flowsheet 21 where $R_{4a}$, Z, n and X are hereinbefore defined. Nitroanilines 138 which may be prepared from 2-amino-4-nitrothiophenol, are acetylated with acetic anhydride ($Ac_2O$) and water at room temperature to give nitro compounds 139. Reduction of nitro compounds 139 with iron and ammonium chloride in refluxing methanol and water furnishes anilines 140. The condensation of anilines 140 and 2-cyano-3-ethoxy-acrylic acid ethyl ester 3 by heating in the absence of solvent gives esters 141. Thermal cyclization of esters 141 in refluxing diphenyl ether/biphenyl or diphenyl ether gives 4-oxo-1,4- dihydro-quinoline-3-carbonitriles 142. Chlorination of 4-oxo-1,4-dihydro-quinoline-3-carbonitriles 142 in refluxing chlorinating reagent selected from phosphorous oxychloride and oxalyl chloride gives 4-chloro-quinolines 143. Condensation of 4-chloro-quinolines 143 with various amines, anilines, alcohols, phenols, mercaptans, and thiophenols of Formula HZ—(CH$_2$)$_n$—X 7a where Z, X and n are hereinbefore defined gives the compounds 4-substituted-quinoline-3-9 carbonitriles 144. This condensation may be accelerated by heating the reaction mixture together with one equivalent of pyridine hydrochloride in alcohol solvents which include isopropanol and 2-ethoxyethanol or by using bases which includes trialkylamines, sodium hydride in an inert solvent which includes tetrahydrofuran (THF), and the like, sodium or potassium alkoxides in alcohol solvents which includes ethanol, and the like. Hydrolysis of 4-substituted-7-acetamido-quinoline-3-carbonitriles 144 in aqueous hydrochloric acid or sodium hyroxide in methanol gives 4-substituted-7-amino-quinoline-3-carbonitriles 145.

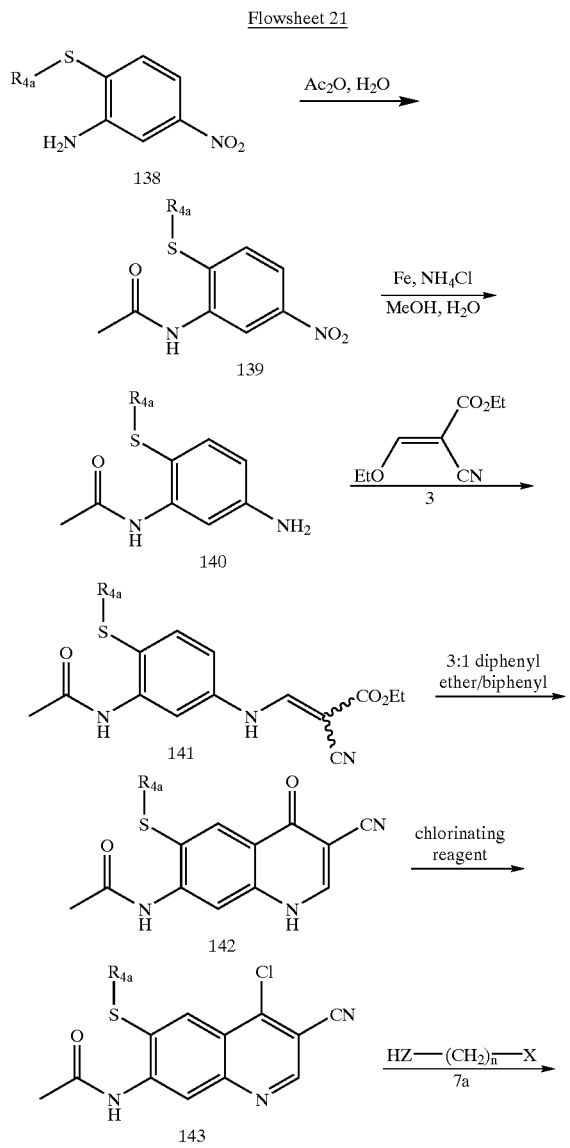

Flowsheet 21

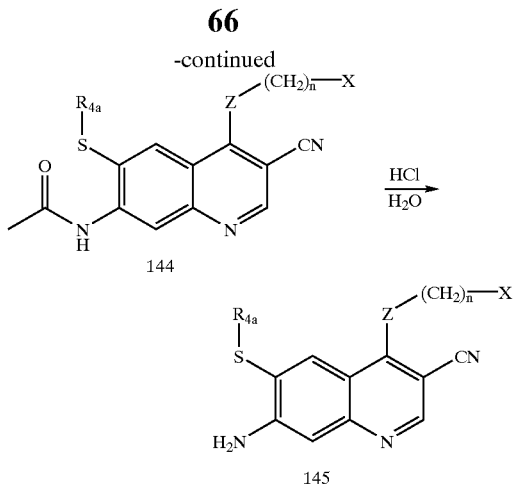

The preparation of the compounds and intermediates of this invention encompassed by Formula 147 is described below in Flowsheet 22 where $R_{4a}$, Z, n, X, $G_1$, $G_2$, $G_3$, and $G_4$ are hereinbefore defined. Deprotecting the thiol group of 4-substituted-6-amino-quinoline-3-carbonitriles 130 may be accomplished by deprotecting procedures such as, but not limited to, HF in anisole or with mercuric trifluoroacetate, trifluoroacetic acid and anisole to give aminothiophenols 146. Condensation of aminothiophenol 146 with dibromides 28 where Z, n, X, $G_1$, $G_2$, $G_3$, and $G_4$ are hereinbefore defined in alcohol solvents including 2-ethoxyethanol, in the presence of potassium carbonate gives the tricyclic compounds 2,3-dihydro-1H-[1,4]thiazino[3,2-g]quinoline-8-carbonitriles 147 of this invention.

Flowsheet 22

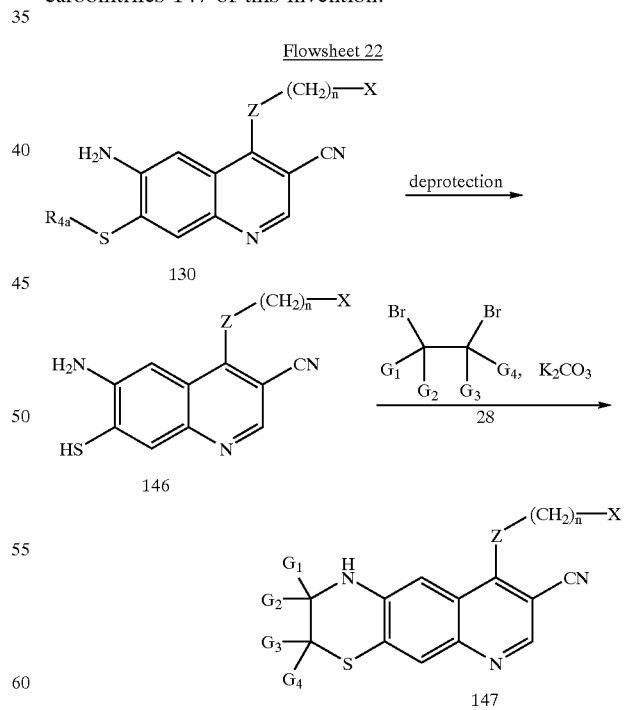

By using similar methods, the intermediates thio-protected anilines 145 may be converted to 3,4-dihydro-2H-[1,4]thiazino[2,3-g]quinoline-8-carbonitriles of this invention 149 as shown in Flowsheet 23.

Flowsheet 23

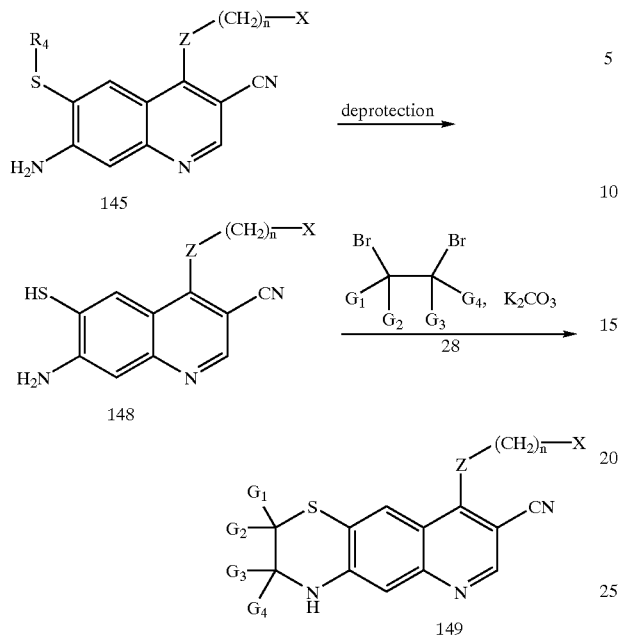

According to the reactions outlined in Flowsheet 24, acylation of 2,3-dihydro-1H-[1,4]thiazino[3,2-g]quinoline-8-carbonitriles 147 with either acid chlorides of Formula 32 or mixed anhydrides of Formula 33 (which are prepared from the corresponding carboxylic acids) in an inert solvent such as tetrahydrofuran (THF) in the presence of an organic base selected from pyridine, triethylamine [$(C_2H_5)_3N$], N,N-diisopropylethylamine, and N-methylmorpholine gives 1-substituted-2,3-dihydro-1H-[1,4]thiazino[3,2-g] quinoline-8-carbonitriles 150. In those cases where the acid chlorides 32 or the mixed anhydrides 33 have an asymmetric carbon atom, they may be used as the racemate or as the individual R or S entantiomers wherein the compounds of this invention will be in the racemic or R and S optically active forms, respectively. In those cases, where $R_2$ contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The BOC protecting group may be removed from the final products by treatment with an acid such as trifluoroactic acid (TFA) while the CBZ protecting group may be removed by catalytic hydrogenation. In those cases where $R_2$ contains hydroxyl groups, the hydroxyl groups may first have to be protected prior to treatment with an anhydride or acid chloride. Suitable protecting groups include, but are not limited to, t-butyldimethylsilyl, tetrahydropyranyl, or benzyl protecting groups. t-Butyldimethylsilyl and tetrahydropyranyl protecting groups may be removed from the final products by treatment with an acid such as acetic acid or hydrochloric acid while the benzyl protecting group may be removed by catalytic hydrogenation. In those cases, in intermediates 2,3-dihydro-1H-[1,4]thiazino[3,2-g]quinoline-8-carbonitriles 150 where X contains primary or secondary amino groups or hydroxyl groups, it may be necessary to protect these groups prior to the reaction with acid chlorides 32 or mixed anhydrides 33. The same amine or alcohol protecting groups describe above may be used and they may be removed from the products as previously described.

Flowsheet 24

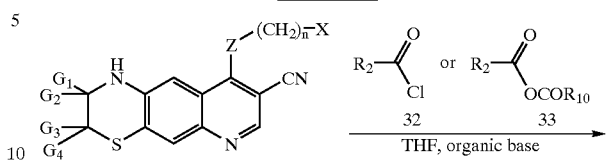

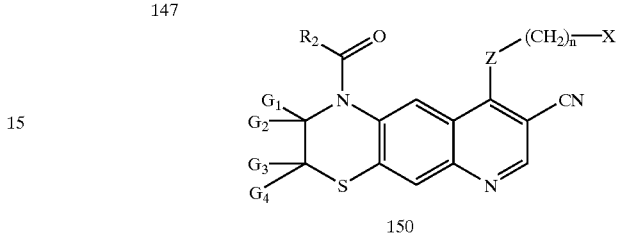

In a similar manner, 3,4-dihydro-2H-[1,4]thiazino[2,3-g] quinoline-8-carbonitriles of Formula 149 may be converted to 4-substituted-3,4-dihydro-21H-[1,4]thiazino[2,3-g] quinoline-8-carbonitriles of Formula 151 as shown in Flowsheet 25. In those cases, in intermediates 3,4-dihydro-2H-[1,4]thiazino[2,3-g]quinoline-8-carbonitriles 149 where X contains primary or secondary amino groups or hydroxyl groups, it may be necessary to protect these groups prior to the reaction with acid chlorides 32 or mixed anhydrides 33. The same amine or alcohol protecting groups described above may be used and they may be removed from the products as previously described.

Flowsheet 25

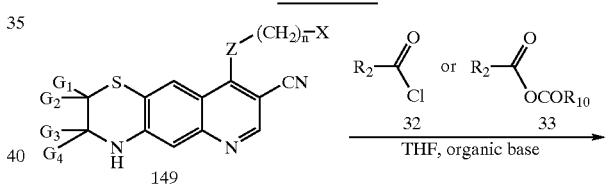

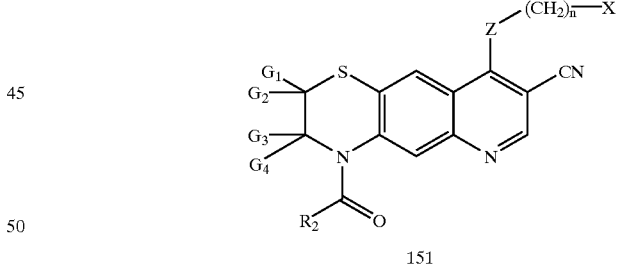

Compounds of this invention represented by Formulas 152–154 may be prepared as shown in Flowsheet 26 wherein Q, $G_1$, $G_2$, $G_3$, $G_4$, $R_5$, J', X, Z, and n are as defined above. Akylation of 2,3-dihydro-1H-[1,4]thiazino[3,2-g] quinoline-8-carbonitriles 147 with 99 may be accomplished by heating in an inert solvent such as N,N-dimethylformamide using a base such as potassium carbonate to give 1-substituted-2,3-dihydro-1H-[1,4]thiazino[3,2-g]quinoline-8-carbonitriles of this invention represented by the Formula 152. When Q is alkoxy, the ester group may be hydrolyzed to an acid using a base such as sodium hydroxide in methanol. In a similar manner, by using intermediates 104 and 105, 1-substituted-2,3-dihydro-1H-[1,4]thiazino[3,2-g] quinoline-8-carbonitriles of this invention represented by Formulas 153 and 154 respectively, may be prepared.

Flowsheet 26
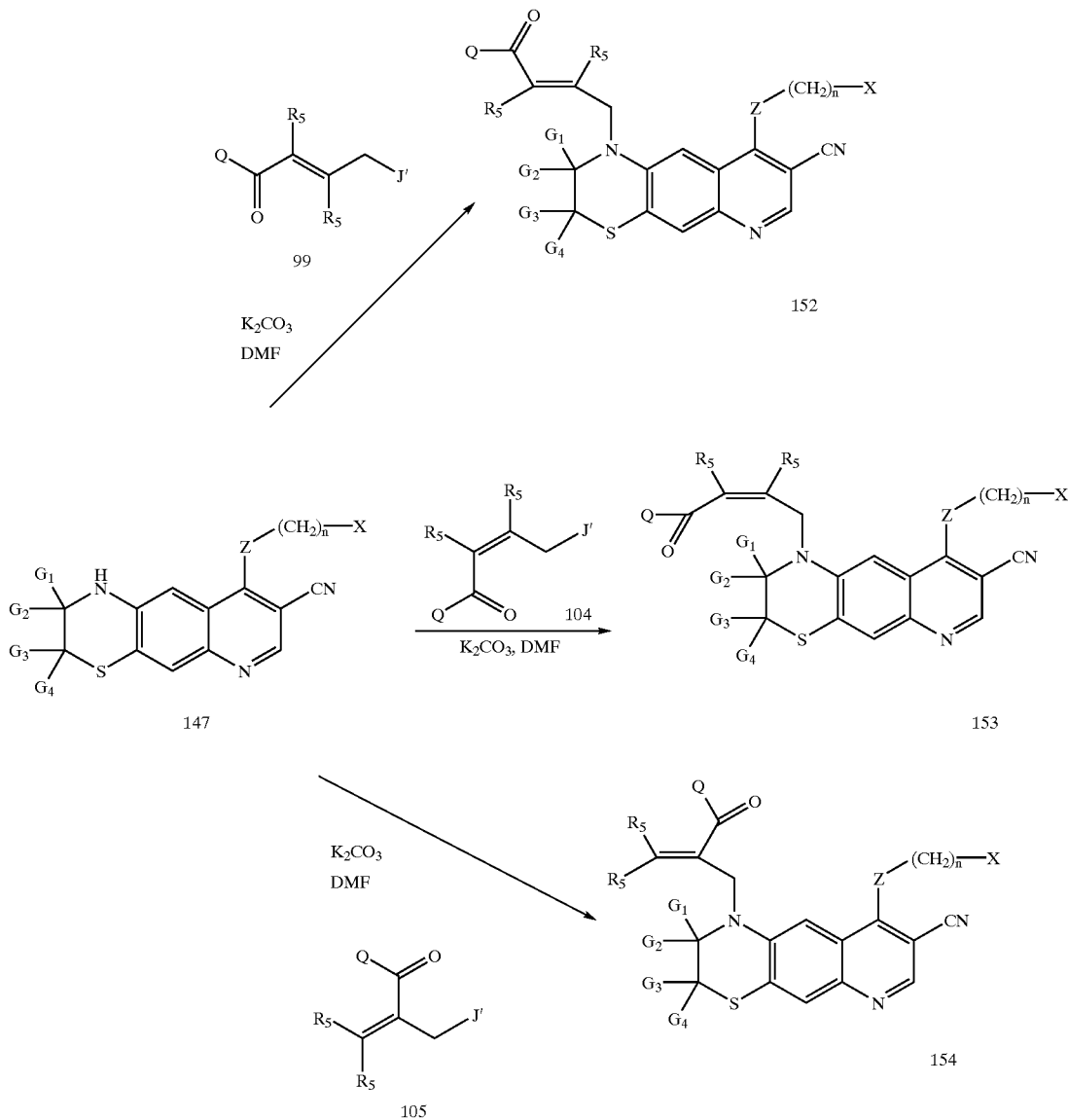
In an entirely analogous manner to Flowsheet 26, the corresponding 4-substituted-3,4-dihydro-2H-[1,4]thiazino [2,3-g]quinoline-8-carbonitriles 155, 156, and 157 are prepared as shown in Flowsheet 27.
Flowsheet 27
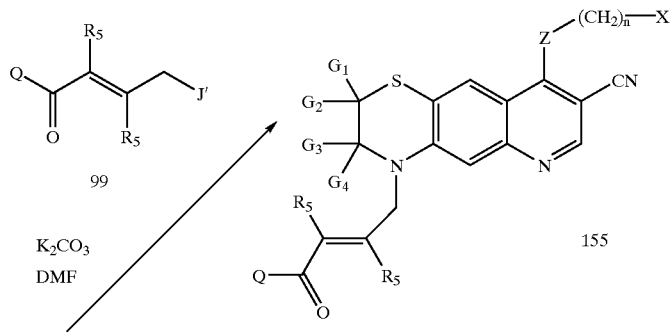

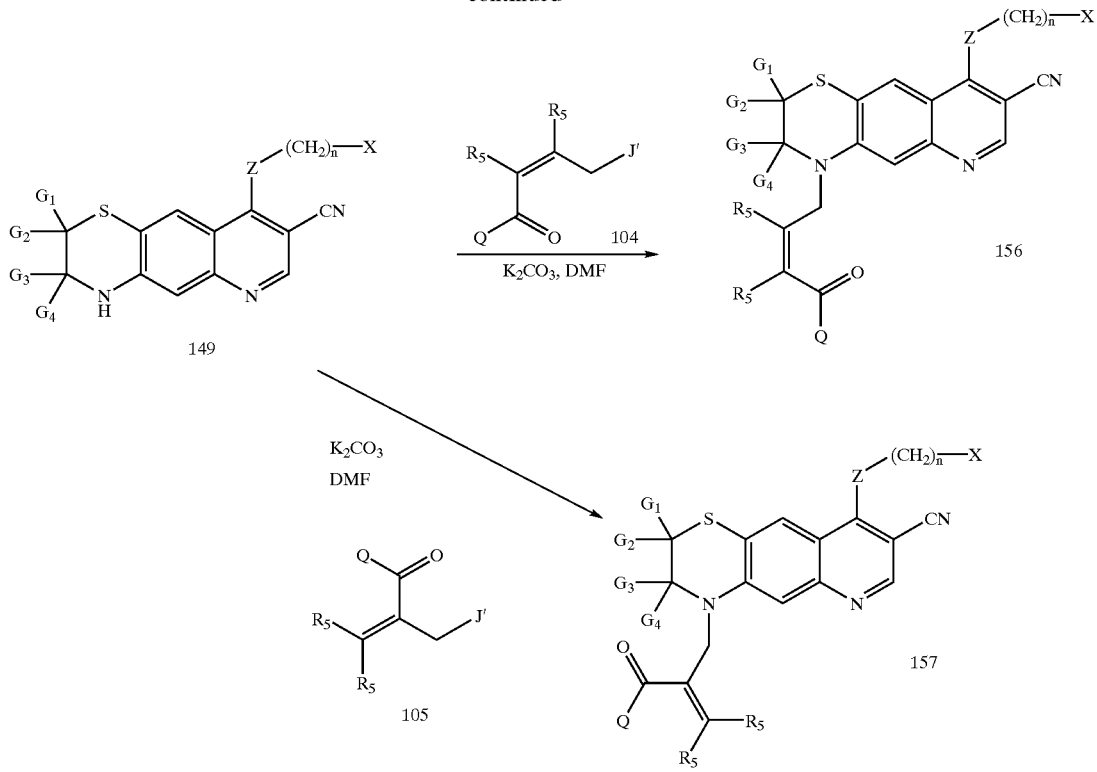

Compounds of this invention represented by Formula 158 may be prepared as shown in Flowsheet 28 wherein $G_1$, $G_2$, $G_3$, $G_4$, $R_5$, X, Z, and n are as defined above. The reaction of reagent 106 with the 2,3-dihydro-1H-[1,4]thiazino[3,2-g]quinoline-8-carbonitriles 147 is accomplished by using an excess of an organic base such as triethylamine and an inert solvent such as tetrahydrofuran to give sulfonamides of this invention represented by Formula 158.

In an entirely analogous manner as shown in Flowsheet 28, the sulfonamides represented by Formula 159 are prepared as shown in Flowsheet 29.

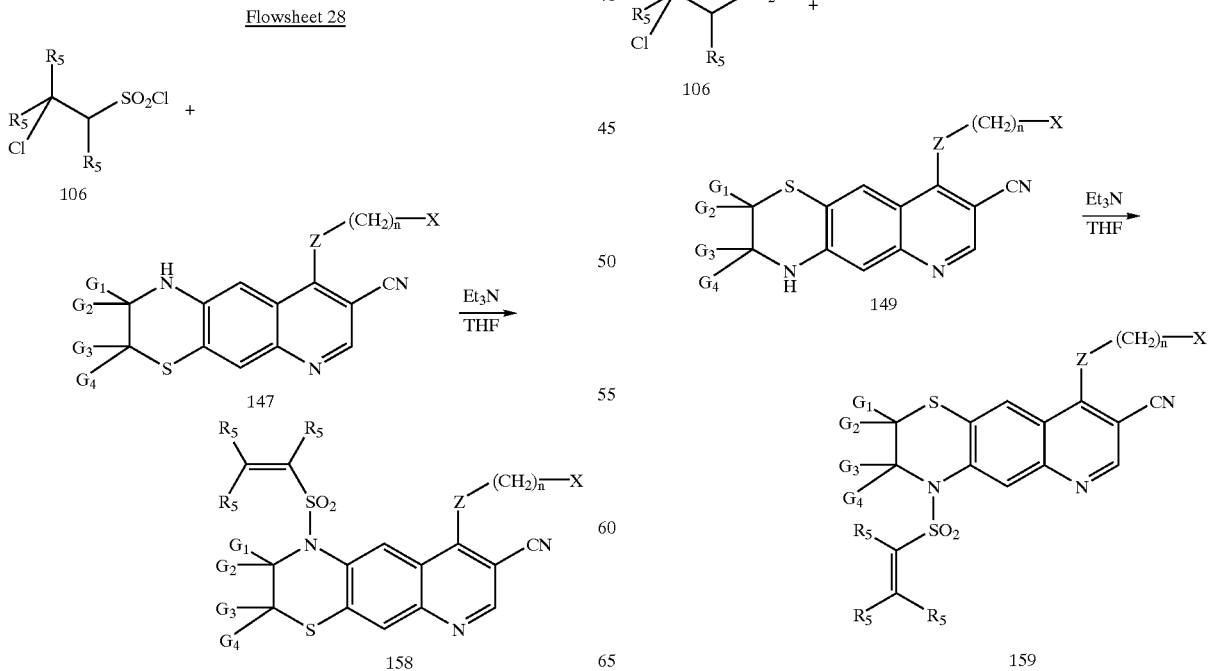

Compounds of this invention represented by Formula 160 may be prepared as shown in Flowsheet 30 wherein $G_1$, $G_2$, $G_3$, $G_4$, $R_{11}$, X, Z, and n are as defined above. The reaction of 2,3-dihydro-1H-[1,4]thiazino[3,2-g]quinoline-8-carbonitriles 147 and aldehydes 109 using sodium borohydride ($NaBH_4$) in N,N-dimethylformamide and trifluoroacetic acid at room temperature gives 1-substituted-2,3-dihydro-1H-[1,4]thiazino[3,2-g]quinoline-8-carbonitriles of this invention represented by 160.

Flowsheet 30

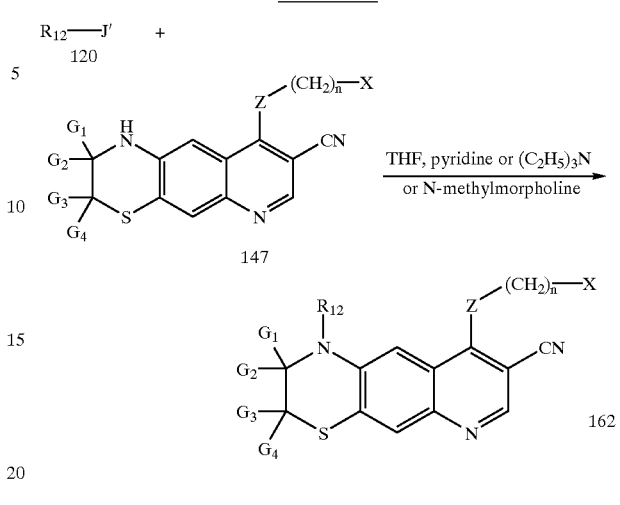

In the same manner, as shown in Flowsheet 30, the 4-substituted-3,4-dihydro-2H-[1,4]thiazino[2,3-g]quinoline-8-carbonitriles represented by Formula 161 may be prepared as shown in Flowsheet 31.

Flowsheet 31

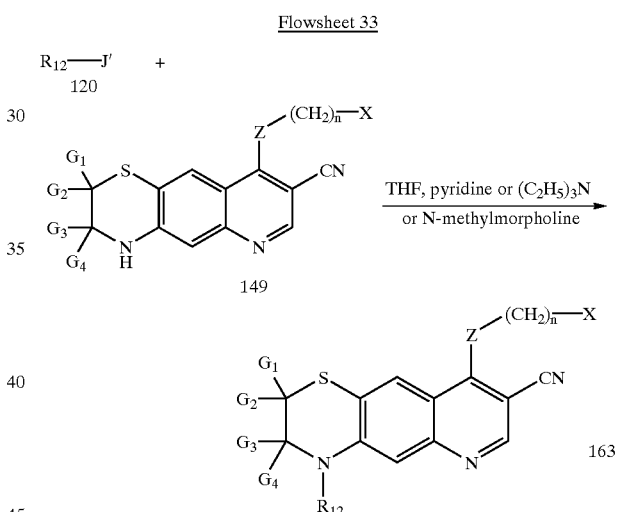

Compounds of this invention represented by Formula 162 may be prepared as shown in Flowsheet 32 wherein $R_{12}$, $G_1$, $G_2$, $G_3$, $G_4$, J', X, Z, and n are as defined above. Treatment of 2,3-dihydro-1H-[1,4]thiazino[3,2-g]quinoline-8-carbonitriles 147 with Formula 120 containing a leaving group J' in an inert solvent such as tetrahydrofuran gives 1-substituted-2,3-dihydro-1H-[1,4]thiazino[3,2-g]quinoline-8-carbonitriles of this invention represented by Formula 162.

Flowsheet 32

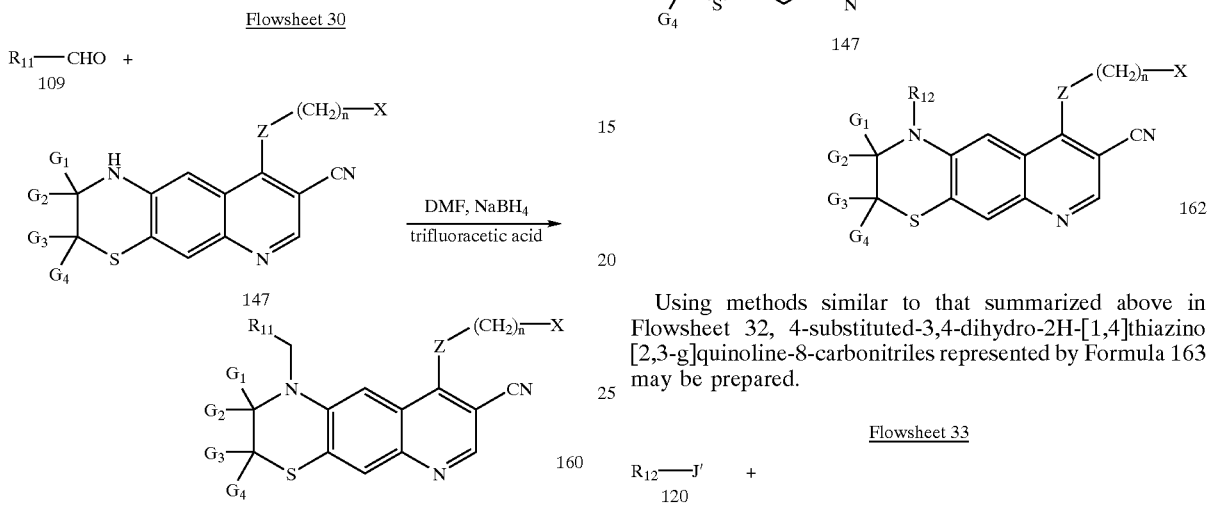

Using methods similar to that summarized above in Flowsheet 32, 4-substituted-3,4-dihydro-2H-[1,4]thiazino[2,3-g]quinoline-8-carbonitriles represented by Formula 163 may be prepared.

Flowsheet 33

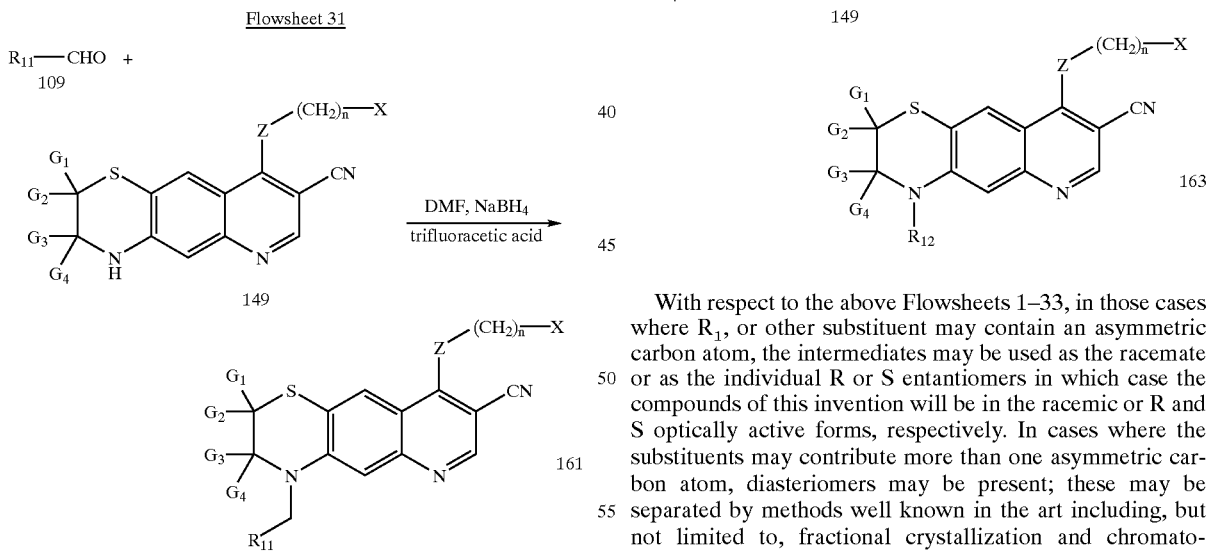

With respect to the above Flowsheets 1–33, in those cases where $R_1$, or other substituent may contain an asymmetric carbon atom, the intermediates may be used as the racemate or as the individual R or S entantiomers in which case the compounds of this invention will be in the racemic or R and S optically active forms, respectively. In cases where the substituents may contribute more than one asymmetric carbon atom, diasteriomers may be present; these may be separated by methods well known in the art including, but not limited to, fractional crystallization and chromatographic methods. In those cases where $R_1$ or other substituents contain primary or secondary amino groups, the amino groups may first have to be used in protected form prior to applying the chemistry described in the above Flowsheets. Suitable protecting groups include, but are not limited to, tert-butoxycarbonyl (BOC) and benzyloxycarbonyl (CBZ) protecting groups. The former protecting group may be removed from the final products by treatment with an acid such as trifluoroactic acid while the latter protecting group may be removed by catalytic hydrogenation. In those cases where $R_1$ or other substituents contain hydroxyl groups, the hydroxyl groups may first have to be used in protected form prior to applying the chemistry described in the above Flowsheets. Suitable protecting groups include, but are not limited to, t-butyldimethylsilyl, tetrahydropyranyl, or benzyl protecting groups. The first two protecting groups may be removed from the final products by treatment with an acid such as acetic acid, hydrofluoric acid, or hydrochloric acid while the latter protecting group may be removed by catalytic hydrogenation.

Representative compounds of this invention were evaluated in several standard pharmacological test procedures that showed that the compounds of this invention possess significant activity as inhibitors of protein kinases and are antiproliferative agents. Disease states which can be treated or inhibited by protein kinase inhibitors include those in which the etiology is at least in part caused by a defect upstream in a signaling pathway from a protein kinase (i.e., colon cancer); those in which the etiology is at least in pail caused by an overexpressed protein kinase (i.e., lung cancer and colonic polyps); and those in which the etiology is at least in part caused by a dysregulated protein kinase (gene turned on at all times; glioblastoma).

Based on the activity shown in the standard pharmacological test procedures, the compounds of this invention are therefore useful as antineoplastic agents. In particular, these compounds are useful in treating, inhibiting the growth of, or eradicating neoplasms such as those of the breast, kidney, bladder, mouth, larynx, esophagus, stomach, colon, ovary, lung, pancreas, liver, prostate and skin.

In addition to having antineoplastic properties, the compounds of the present invention are useful in treating or inhibiting a variety of protein tyrosine kinase-associated disorders including: polycystic kidney disease, colonic polyps, restenosis; atherosclerosis; angiofibromas; hemangiomas; diabetes; acute and chronic nephropathies; Kaposi's sarcoma; neovascularization associated with macular degeneration; rheumatoid arthritis; osteoarthritis; transplant rejection; psoriasis; lupus; graft versus host disease; glomerulonephritis; respiratory and skin allergies; autoimmune alopecia; Autoimmune Hyperthyroidism; multiple sclerosis; atopic dermatitis; and systemic sclerosis; and are useful as antibacterial and antiviral agents.

As used in accordance with this invention, the term providing an effective amount of a compound means either directly administering such compound, or administering a prodrug, derivative, or analog which will form an effective amount of the compound within the body.

In addition to the above utilities some of the compounds of this invention are useful for the preparation of other compounds of this invention.

The test procedures used and results obtained are shown below.

STANDARD PHARMACOLOGICAL TEST PROCEDURES

Representative compounds of this invention were evaluated in several standard pharmacological test procedures that showed that the compounds of this invention possess significant activity as inhibitors of protein tyrosine kinase and are antiproliferative agents. Based on the activity shown in the standard pharmacological test procedures, the compounds of this invention are therefore useful as antineoplastic agents. The test procedures used and results obtained are shown below.

Inhibition of Epidermal Growth Factor Receptor Kinase (EGF-R) Using Recombinant Enzyme Representative test compounds were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme used in this assay is the His-tagged cytoplasmic domain of EGFR. A recombinant baculovirus (vHcEGFR52) was constructed containing the EGFR cDNA encoding amino acids 645–1186 preceded by Met-Ala-(Ris)$_6$. Sf9 cells in 100 mm plates were infected at an moi of 10 pfu/cell and cells were harvested 48 hours post infection. A cytoplasmic extract was prepared using 1% Triton X-100 and applied to Ni-NTA column. After washing the column with 20 mM imidazole, HcEGFR was eluted with 250 mM imidazole (in 50 mM Na$_2$RPO$_4$, pH 8.0, 300 mM NaCl). Fractions collected were dialyzed against 10 mM HEPES, pH 7.0, 50 mM NaCl, 10% glycerol, 1 μg/mL antipain and leupeptin and 0.1 mM Pefabloc SC. The protein was frozen in dry ice/methanol and stored −70° C.

Test compounds were made into 10 mg/mL stock solutions in 100% dimethylsulfoxide (DMSO). Prior to experiment, stock solutions were diluted to 500 μM with 100% DMSO and then serially diluted to the desired concentration with HEPES buffer (30 mM HEPES pH 7.4).

For the enzyme reaction, 10 μL of each inhibitor (at various concentrations) were added to each well of a 96-well plate. To this was added 3 μL of enzyme (1:10 dilution in 10 mM HEPES, pH 7.4 for final conc. of 1:120). This was allowed to sit for 10 minutes on ice and was followed by the addition of 5 μl peptide (80 uM final conc.), 10 μl of 4×Buffer (Table A), 0.25 μL $^{33}$P-ATP and 12 μL H$_2$O. The reaction was allowed to run for 90 minutes at room temperature and was followed by spotting the entire volume on to precut P81 filter papers. The filter discs were washed 2× with 0.5% phosphoric acid and radioactivity was measured using a liquid scintillation counter.

TABLE A

| Reagent | Final | 100 Rxns |
| --- | --- | --- |
| 1 M HEPES (pH 7.4) | 12.5 mM | 50 μL |
| 10 mM Na$_3$VO$_4$ | 50 μM | 20 μL |
| 1 M MnCl$_2$ | 10 mM | 40 μL |
| 1 mM ATP | 20 μM | 80 μL |
| $^{33}$P-ATP | 2.5 μCi | 25 μL |

The inhibition data for representative compounds of the invention are shown below in TABLE 1. The IC$_{50}$ is the concentration of test compound needed to reduce the total amount of phosphorylated substrate by 50%. The % inhibition of the test compound was determined for at least three different concentrations and the IC$_{50}$ value was evaluated from the dose response curve. The % inhibition was evaluated with the following formula:

% inhibition=100−[CPM(drug)/CPM(control)]×100 where CPM(drug) is in units of counts per minute and is a number expressing the amount of radiolabeled ATP (γ-$^{33}$P) incorporated onto the RR-SRC peptide substrate by the enzyme after 90 minutes at room temperature in the presence of test compound as measured by liquid scintillation counting. CPM(control) is in units of counts per minute and was a number expressing the amount of radiolabeled ATP (γ-$^{33}$P) incorporated into the RR-SRC peptide substrate by the enzyme after 90 minutes at room temperature in the absence of test compound as measured by liquid scintillation counting. The CPM values were corrected for the background counts produced by ATP in the absence of the enzymatic reaction. Where it was possible to determine an $IC_{50}$ value, this is reported in TABLE 1 otherwise the % inhibition at 0.5 μM concentration of test compound is shown in TABLE 1.

TABLE 1

Inhibition of EGF-R Kinase (recombinant enzyme)

| Example | IC50 (μM) | % Inhibition @ 0.5 (μM) |
|---------|-----------|--------------------------|
| 7 | 1[a] | 35.5[a] |
| 8 | 1[a] | 29.95[a] |
| 9 | 0.17[b] | 56.5[b] |
| 10 | 0.2 | 57.8 |
| 11 | 0.001 | 73.0 |
| 12 | 0.005 | 53.5 |

[a]average of two tests
[b]average of three tests

DELFIA Assay for Identification of c-Met Receptor Kinase Inhibitors

The c-Met kinase assay was performed as a DELFIA (dissociation enchanced lanthanide fluorometric immunoassay), an ELISA-like protocol based upon time-resolved fluorometry as described previously [Braunwalder, A. F., Yarwood, D. R., Sills, M. A., and Lipson, K. E., Anal. Biochem. 238, 159–164 (1996)]. The protocol was adopted for the screening of inhibitors of the kinase activity of recombinant c-Met. [Loganzo, F., and. Hardy, C., American Biotechnology Laboratory 16(13), 26–28 (1998)]. The cytoplasmic domain of c-Met was generated by reverse transcriptase-polymerase chain reaction using RNA isolated from human mammary epithelial cells as template, cloned into the pFastBac-HTc vector (Life Technologies) and protein expressed in Sf9 insect cells by baculovirus infection. Protein was purified by imidazole elution from Ni-NTA resin (Invitrogen, Carlsbad, Calif.) or Talon resin (Clontech, Palo Alto, Calif.). Various conditions were evaluated for the kinase screening protocol and screening was accomplished with the following method. Polystyrene Maxisorp plates (Nunc) were pre-coated for 1 hour to overnight at room temperature with 5 μg/ml poly($Glu_4$-Tyr) diluted in Tris-buffered saline (TBS). Plates were washed 3× with TBS. c-Met protein preparation was diluted 1:80 into 0.1% BSA/4 mM HEPES. A master mix was prepared consisting of: 1 volume of diluted c-Met, 1 volume of 5×buffer (20 mM HEPES, pH 7.4; 2 mM MnCl2; 100 μM $Na_3VO_4$; 1 mM DTT), 0.9 volume of water. Master mix (29 μl) was added to the wells of peptide-coated microtiter plates. For assays where c-Met autophosphorylation was evaluated, plates were uncoated and c-Met was diluted into 4 mM HEPES at 1:40 without BSA. Compounds (1 μl) at various dilutions (1 mM to 0.1 μM) prepared in DMSO were added and mixed well with an automatic piptettor. After incubation 20 minutes at room temperature, the reaction was initiated with 20 μl of 62.5 μM ATP/50 mM MgCl2 (final 25 μM ATP/20 mM $MgCl_2$ in assay). Reactions were incubated 45 minutes at room temperature. Plates were then washed 3× with 100 μl each of DELFIA wash buffer (Wallac). Antibody binding was performed by adding 75 μl of Europium-conjugated anti-phosphotyrosine diluted 1:2000 in Assay Buffer (Wallac) for 1 hour at room temperature. Plates were washed 3× with DELFIA wash buffer. Detection was done by addition of 100 μl of Enhancement Solution (Wallac). After 30 minutes, plates were read in a Wallac VICTOR-2 time-resolved fluorometer. Inhibition data was reported as europium counts for compound treated wells normalized to control counts. $IC_{50}$ values were obtained by using log doses of compound and calculated using Data Analysis Toolbox software, version 1.0.2 (MDL Information Systems, Inc.).

TABLE 2

Inhibition of c-Met Kinase

| Example | % Inhibition (μM) | Dose (μg/mL) |
|---------|-------------------|--------------|
| 7 | 80 | 10 |
| 8 | 91 | 10 |
| 10 | 50 | 10 |
| 11 | 42 | 10 |
| 12 | 66 | 10 |

Src Kinase Assay

Inhibitors of $p60^{c-src}$ (partially purified preparation purchased from Upstate Biotechnologies) tyrosine kinase activity are analyzed in an ELISA format. The Boehringer Mannheim Tyrosine Kinase Assay Kit (Catalog number 1-534505) with a cdc2 substrate peptide containing Tyr15 is used for the assay. HRP-conjugated anti-phosphotyrosine is used to detect phosphorylated peptide via a color reaction. Conditions recommended by the manufacturer are employed.

Reaction conditions: Five microliter aliquots of each compound prepared fresh at the time of the assay are added as a solution in 10 mM HEPES pH 7.5, 10% DMSO to the reaction well. Thirty-five microliters of reaction mix containing Src, buffer and peptide/bovine serum albumin mix are added to the compound wells and incubated at 30° C. for 10 minutes (reaction buffer: 50 mM TrisHCl pH 7.5, 10 mM $MgCl_2$, 0.1 mM EGTA, 0.5mM $Na_3VO_4$). The reaction is started by addition of 10 microliters of ATP, incubated at 30° C. for 1 hour, and stopped by addition of 20 microliters of 0.5M EDTA. The reaction mixture with the phosphorylated peptide was then transferred to a streptavidin-coated microtiter plate (provided in the kit) and allowed to bind for 20 minutes. Unbound peptide and reaction mixture was decanted and the plate was washed with PBS six times. Horseradish peroxidase-conjugated phosphotyiosine antibody supplied in the kit was incubated with the plate for one hour, then decanted. The plate was again washed with PBS six times. Substrate (provided in the kit) was added and absorbance at 405 nm was measured.

Activity was determined as % inhibition as calculated by the formula:

(1−$Abs$/$Abs$(max))×100=% inhibition.

Where multiple concentrations of the test agent were used, an $IC_{50}$ (concentration which gives 50% inhibition) could be determined.

The result obtained for representative compound of this invention is listed in Table 3.

TABLE 3

Inhibition of Src kinase

| Example | $IC_{50}$ (μM) |
|---------|----------------|
| 24 | 1.01 |

Raf-1 Kinase Cascade Assay Procedure

Raf-1 (c-Raf) is used to phosphorylate and activate inactive GST-MEK1 which then can phosphorylate and activate inactive p42 GST-MAPK, which subsequently is measured for phosphorylation of the TEY sequence (aa's 202–204) by a phospho-specific antibody from Sigma (cat. #77439219041) Reagents: Sf9 insect cell lysate containing full length 6his-tagged recombinant human c-Raf. (Specific Activity: ~200 U/ml). Human Non-active Mek-1-GST and human GST-MAP kinase (recombinant proteins produced in *E. coli*).

Stock Solutions c-Raf Assay:

1. Assay Dilution Buffer (ADB): 20 mM MOPS, pH 7.2, 25 mM β-glycerol phosphate, 5 mM EGTA, 1 mM sodium orthovanadate, 1 mM dithiothreitol.
2. Magnesium/ATP Cocktail: 500 μM cold ATP and 75 mM magnesium chloride in ADB.
4. Active Kinase: Human Active c-Raf: Use at 0.4 U per assay point.
5. Non-active GST-MEK1: Use at 0.1 μg per assay point.
6. Non-active GST-p42 MAP Kinase: Use at 1.0 μg per assay point.

Stock Solutions ELISA:

1. TBST-Tis (50 mM, pH 7.5), NaCl (150 mM), Tween-20 (0.05%)
2. Superblock (Pierce)
3. Anti-GST Ab (Pharmacia)
4. Anti-Phospho MAPK (Sigma)
5. Anti-Mouse Ab/Europium conjugate (Wallac) Assay Procedure:

First Stage: c-Raf Dependent Activation of GST-MEK and GST-MAPK

1. Add 20 ml of ADB per assay (i.e. per well of a 96 well plate)
2. Add 10 ml of 0.5 mM cold ATP and 75 mM magnesium chloride in ADB.
3. Add 2 ml of c-Raf (0.4U/assay), in conjunction with 1.6 ml non-active MEK1 (0.4 mg/assay).
4. Add 4 ml of non-active GST-p42 MAP Kinase (1.0 mg/assay).
5. Incubate for 60 minutes at 30° C. in a shaking incubator.
6. Transfer this mixture to an anti-GST Ab coated 96 well plate (Nunc Immunosorb plates coated o/n with a-GST, then blocked with Pierce Superblock).
7. Incubate for 60 minutes at 30° C. in a shaking incubator.
8. Wash 3× with TBST, add Anti-Phospho MAPK (Sigma) (1:3000).
9. Incubate for 60 minutes at 30° C. in a shaking incubator.
10. Wash 3× with TBST, add Anti-Mouse Ab/Europium conjugate (Wallac) (1:500).
11. Incubate for 60 minutes at 30° C. in a shaking incubator.
12. Wash 3× with TBST, Read plates in Wallac Victor model Plate Reader.
13. Collect data analyze in Excel for single point and IC50 determinations.

Single point assay—% inhibition at 10 mg/ml (% Inhibition=1−cpd.treated sample/untreated control). Typically Raf-1 assay is run at compound concentrations from 10 μM to 30 nM in half log dilutions. (% inhibition is determined for each compound concentration). The results obtained for representative compound of this invention are listed in Table 4.

TABLE 4

Inhibition of c-raf Kinase

| | raf | |
|---|---|---|
| Example | % inhibition | dose (μg/mL) |
| 7 | −5.00 | 0.03 |
| | 2.00 | 0.1 |
| | 8.00 | 0.3 |
| | 16.00 | 1.0 |
| | 68.00 | 3.0 |
| | 90.00 | 10.0 |

Inhibition of Cancer Cell Growth as Measured by Cell Number

Human tumor cell lines were plated in 96-well plates (250 μ/well, 1–6×10 $10^4$ cells/ml) in RPMI 1640 medium, containing 5% FBS (Fetal Bovine Serum). Twenty four hours after plating, test compounds were added at five log concentrations (0.01–100 mg/ml) or at lower concentrations for the more potent compounds. After 48 hours exposure to test compounds, cells were fixed with trichloroacetic acid, and stained with Sulforhodamine B. After washing with trichloroacetic acid, bound dye was solubilized in 10 mM Tris base and optical density was determined using a plate reader. Under conditions of the assay the optical density is proportional to the number of cells in the well. $IC_{50}$s (concentrations causing 50% inhibition of cell growth) were determined from the growth inhibition plots. The test procedure is described in details by Philip Skehan et. al, *J. Natl. Canc. Just.*, 82, 1107–1112 (1990). These data are shown below in TABLE 5. Information about some of the cell lines used in these test procedures is available from the American Type Tissue Collection: Cell Lines and Hybridomas, 1994 Reference Guide, 8th Edition. The Her2Neu cell line is a 3T3 line that has been transfected with Her2 receptor kinase.

TABLE 5

Inhibition of Cancer Cell Growth as Measured by Cell Number ($IC_{50}$ μg/mL)

| Ex. | MDA435 | A431 | SKBR3 | SW620 | 3T3 | Her2Neu |
|---|---|---|---|---|---|---|
| 7 | 1.43[a] | 0.5273[a] | 0.968 | 2.90[a] | 3.02[a] | 3.90[a] |
| 8 | 0.1021[a] | 0.3157[a] | 0.665 | 0.2452[a] | 0.023 | 0.104 |
| 9 | 0.240[b] | 0.1079[b] | — | 0.165[b] | 0.1694[b] | 0.1504[b] |
| 10 | 2.72[a] | 1.007[a] | 1.0665[a] | 1.89[a] | 1.99[a] | >5[a] |
| 11 | >5[a] | 1.90[a] | 2.53[a] | >5[a] | 3.89[a] | >5[a] |
| 12 | 2.36[a] | 0.4705[a] | 0.649[a] | 1.50[a] | 1.49[a] | >5[a] |

[a]average of two tests
[b]average of three tests

In Vivo Inhibition of the Growth of Human Epidermoid Tumors (A431)

BALB/c nu/nu female mice (Charles River, Wilmington, Mass.) were used in the in vivo standard pharmacological test procedures. Human epidermoid carcinoma cells A-431 (American Type Culture Collection, Rockville, Md. #CRL-155) were grown in vitro as described above. A unit of 5×10⁶ cells were injected subcutaneously into mice. When tumors attained a mass of between 100 and 150 mg, the mice were randomized into treatment groups (day zero). Mice were treated orally (PO) once a day on days 1 through 10 post staging with doses of either 40, 20, 10, 3 or 1 mg/kg/dose of the compound to be evaluated in 0.2% Klucel. Control animals received no drug. Tumor mass was determined every 7 days [(length×width$^2$)/2] for 28 days post staging. Relative tumor growth (Mean tumor mass on day 7, 14, and 21 divided by the mean tumor mass on day zero) is determined for each treatment group. The % T/C (Tumor/ Control) is determined by dividing the relative tumor growth of the treated group by the relative tumor growth of the placebo group and multiplying by 100. A compound is considered to be active if the % T/C is found to be=42%.

The ability of the compound of Example 9 to inhibit the growth of human epideimoid tumors (A431) in vivo is demonstrated below in TABLE 6.

TABLE 6

In Vivo Inhibition of the Growth of Human Epidermoid Tumors (A431) in Mice by the Compound of Example 9

| Dose (mg/kg/dose)$^a$ PO | RTG$^b$ Day 7 | % T/C$^c$ | RTG$^b$ Day 14 | % T/C$^c$ | RTG$^b$ Day 21 | % T/C$^c$ | (p)d | S/T$^e$ |
|---|---|---|---|---|---|---|---|---|
| Control (0.5% Methocel 0.4% Tween 80) | 4.54 | | 10.99 | | 17.27 | | | 10/10 |
| 40 | 3.40 | 75 | 5.93 | 53 | 7.15 | 41 | <0.01 | 5/5 |
| 20 | 5.40 | 118 | 10.56 | 96 | 14.56 | 84 | 0.29 | 5/5 |
| 10 | 4.81 | 105 | 9.66 | 87 | 11.09 | 64 | 0.10 | 5/5 |
| 3 | 4.76 | 104 | 11.79 | 107 | 23.77 | 137 | 0.76 | 5/5 |
| 1 | 4.66 | 103 | 8.11 | 73 | 13.23 | 76 | <0.01 | 5/5 |

$^a$Compound administered on days 1 through 10.

$^b$Relative Tumor Growth (RTG) = $\dfrac{\text{Mean Tumor Mass on Day 7, 14, 21}}{\text{Mean Tumor Mass on Day 0}}$ $^c$% T/C = $\dfrac{\text{Relative Tumor Growth of Treated Group}}{\text{Relative Tumor Growth of Placebo Group}} \times 100$ $^d$Statistical Analysis (Student's T-test) of Log Relative Tumor Growth.
A p-value (p ≦ 0.05) indicates a statistically significant reduction in Relative Tumor Growth of Treated Group compared to the Placebo Control.
$^e$S/T = # of Survivors/# of Treated on Day +21 post tumor staging.

As indicated by the results presented in TABLE 5, the compound of Example 9 is an effective inhibitor of tumor growth in vivo and is therfore useful for the treatment of cancer.

Based on the results obtained for representative compounds of this invention, the compounds of this invention are antineoplastic agents which are useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung. The compounds of this invention are also useful in treating, inhibiting the growth of, or eradicating neoplasms of the breast that express the receptor protein produced by the erbB2 (Her2) oncogene. Additionally, the compounds of this invention are useful in treating or inhibiting polycystic kidney disease and colonic polyps.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable callier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid catiers include starch, lactose, dicalcium phosphate, microcrystalline cellulose, sucrose and kaolin, while liquid catTiers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

The compounds of this invention and their preparation are illustrated by the following non-limiting examples.

EXAMPLE 1

7-Methoxy-4-oxo-1,4-dihydro-quinoline-3-carbonitrile

An amount of 3-methoxy-phenylamine (45.3 g, 0.37 mol) and 2-cyano-3-ethoxy-acrylic acid ethyl ester (62.2 g, 0.37 mol), were heated at 120° C. for 0.5 hours, during which 14.4 mL of ethanol was collected by a Dean-Stark trap. To this was added a solution of biphenyl (333 mL) and phenyl ether (666 mL), and the mixture was heated at 256° C. for 6 hours, during which 22 mL of ethanol was collected by a Dean-Stark trap. The mixture was cooled to room temperature and filtered. The solid was washed with hexane and dried to give a brown solid (46.2 g, 63% yield), m.p 324–325° C.; $^1$H NMR (DMSO-$d_6$) δ 12.63 (bs, 1H), 8.67 (s, 1H), 8.03 (d, J =9 Hz, 1H), 7.08 (dd, J=9 Hz, J=3 Hz, 1H), 7.01 (dd, J=3 Hz, 1H), 3.88 (s, 3H); HRMS (EI) m/z 223.04793 (M+Na); MS (ES) m/z 201.0 (M+1). Analysis for $C_{11}H_8N_2O_2.0.1H_2O$: Found: C, 65.53; H, 4.09; N, 13.93. Calcd: C, 65.35; H, 4.06; N, 13.86.

EXAMPLE 2

7-Methoxy-6-nitro-4-oxo-1,4-dihydio-quinoline-3-carbonitrile

An amount of 7-methoxy-4-oxo-1,4-dihydro-quinoline-3-carbonitrile (30 g, 0.15 mol) was stirred in trifluoroacetic acid (450 mL), and to this was added portionwise over 3.5 hours, ammonium nitrate (30 g, 0.38 mol). The reaction mixture was evaporated to a black paste and subsequently stirred with ice water, saturated sodium bicarbonate solution, and filtered to obtain 32.3 g of the crude product. Additional purification was carried out by refluxing the crude material in acetic acid (1300 mL) for 0.5 hours. The mixture was cooled to room temperature, filtered and dried to give a brown solid (14.4 g, 40% yield), m.p. 240° C. decomp.; $^1$H NMR (DMSO-$d_6$) δ 12.9 (s, 1H), 8.80 (s, 1H), 8.54 (s, 1H), 7.27 (s, 1H), 4.02 (s, 3H); HRMS (EI) m/z 245.0408 (M+1). Analysis for $C_{11}H_7Cl_2N_3O_4.0.1H_2O_{0.1}CH_3CO_2C_2H_5$: Found: C, 53.24; H, 2.98; N, 16.35. Calcd: C, 53.46; H, 3.13; N, 16.41.

EXAMPLE 3

4-Chloro-7-methoxy-6-nitro-quinoline-3-carbonitrile

An amount of 7-methoxy-6-nitro-4-oxo-1,4-dihydro-quinoline-3-carbonitrile (5 g, 20.4 mmol) was stirred with phosporous oxychloride (24.7 g, 0.16 mol), and phosporous pentachloride (4.3 g, 0.02 mol), and heated at reflux for 2.5 hours. After cooling to room temperature, the black solid was subsequently washed with hexane, filtered, stirred with saturated sodium bicarbonate solution, and extracted with ethyl acetate. The organic layer was separated and filtered through a Magnesol pad and evaporated to dryness to give a brown solid (3.2 g, 59%), which was used without further purification, m.p. 214–215° C.; $^1$H NMR (DMSO-$d_6$) δ 9.28 (s, 1H), 8.85 (s, 1H), 7.91 (s, 1H), 4.13 (s, 3H); HRMS (EI) m/z 264.01711 (M+1). Analysis for $C_{11}H_6ClN_3O_3.0.02$ mol $CH_3(CH_2)_4CH_3$: Found: C, 50.70; H, 2.55; N, 16.07. Calcd: C, 50.33; H, 2.39; N, 15.84.

EXAMPLE 4

4-(3-Chloro-4-fluoro-phenylamino)-7-methoxy-6-nitro-quinoline-3-carbonitrile

An amount of 4-chloro-7-methoxy-6-nitro-quinoline-3-carbonitrile (7.1 g, 26.9 mmol), and 3-chloro-4-fluoro-phenylamine (3.9 g, 26.8 mmol), were stirred in 2-propanol (70 mL), and heated at reflux for 2 hours. The mixture was cooled to room temperature and stirred for an additional 20 hours. The reaction mixture was evaporated to dryness, stirred with ethyl acetate and saturated sodium bicarbonate solution. After separation of the layers, the organic layer was washed with saturated brine solution and dried on magnesium sulfate, to give a dark green powder (9.9 g, 99%), which was used without further purification.

$^1$H NMR (DMSO-$d_6$) δ 10.2 (s, 1H), 9.13 (s, 1H), 8.68 (s, 1H), 7.63 (mn, 2H), 7.49 (m, 1H), 7.39 (m, 1H), 4.08 (s, 3H); HRMS (EI) m/z 373.04915 (M+1); MS (ES) m/z 373.0 (M+1). Analysis for $C_{17}H_{10}OClFN_4O_3$: Found: C, 54.84; H, 2.59; N, 14.77. Calcd: C, 54.78; H, 2.70; N, 15.03.

EXAMPLE 5

6-Amino-4-(3-chloro-4-fluoro-phenylamino)-7-methoxy-quinoline-3-carbonitrile

An amount of 4-(3-chloro-4-fluoro-phenylamino)-7-methoxy-6-nitro-quinoline-3-carbonitrile (9.9 g, 0.27 mmol) was combined with ammonium chloride (11.4 g, 0.21 mol), iron powder (8.9 g, 0.16 mol), methanol (200 mL), and water (50 mL), and heated at reflux for 2 hours. An additional amount of iron (1.0 g, 0.018 mol) and ammonium chloride (1.0 g, 0.019 mol) were added and the mixture was refluxed for an additional 3.5 hours. The reaction mixture was filtered hot and the residue was washed with boiling methanol to extract the product. The filtrate was evaporated to a slurry and stirred with saturated sodium bicarbonate solution and ethyl acetate. The layers were separated, and the organic layer was dried over magnesium sulfate and evaporated to dryness to give a green powder (7.8 g, 85%), which was used without further purification.

$^1$H NMR (DMSO-d$_6$) δ 9.26 (s, 1H), 8.40 (s, 1H), 7.35 (t, 1H), 7.26 (m, 2H), 7.18 (s, 1H), 7.07 (m, 1H), 5.59 (s, 2H), 3.98 (s, 3H); HRMS (EI) m/z 342.0680 (M+1).

EXAMPLE 6

6-Amino-4-(3-chloro-4-fluoro-phenylamino)-7-hydroxy-quinoline-3-carbonitille

An amount of 6-amino-4-(3-chloro-4-fluoro-phenylamino)-7-methoxy-quinoline-3-carbonitrile (100 mg, 0.29 mmol) was heated with pyridine hydrochloride (1 g, 8.7 mmol) at 205° C. for 0.5 hours. The mixture was cooled to room temperature and stirred with ammonium hydroxide (1.5 mL) for 15 minutes and evaporated to a brown solid. The product was stirred in water, filtered, and dried to give a green powder (85.4 mg, 90% yield), which was used without further purification, mp 274–277° C.; $^1$H NMR (DMSO-d$_6$) δ 10.85 (bs, 1H), 9.18 (s, 1H), 8.34 (s, 1H), 7.34 (m, 1H), 7.23 (m, 1H), 7.15 (m, 2H), 7.03 (m, 1H), 5.43 (bs, 2H); HRMS (EI) m/z 359.0338 (M+1). Analysis for C$_{16}$H$_{10}$ClFN$_4$.O0.55H$_2$O: Found: C, 56.76; H, 3.16; N, 16.17. Calcd: C, 56.70; H, 3.28; N, 16.54.

EXAMPLE 7

9-(3-Chloro-4-fluoroanilino)-2,3-dihydro-1H-[1,4]oxazino[3,2-g]quinoline-8-carbonitrile An amount of 6-amino-4-(3-chloro-4-fluoro-phenylamino)-7-hydroxy-quinoline-3-carbonitrile (4 g, 12.2 mmol) was stirred in 2-ethoxyethanol (480 mL), and to this were added 1,2-dibromoethane (22.9 g, 12.2 mmol), and potassium carbonate (10.1 g, 73 mmol), and the mixture was heated at 135° C. for 0.5 hours. After cooling to room temperature, the mixture was filtered over a thin silica pad and evaporated to an oil. To this was added ethyl acetate and saturated brine solution, and the layers were separated. The organic layer was dried on sodium sulfate and evaporated to a brown oil. Purification was carried out by flash chromatography (70% ethyl acetate in hexane) to yield a yellow solid (1.95 g, 45% yield), m.p. 244–245° C.; $^1$H NMR (DMSO-d$_6$) δ 9.32 (s, 1H), 8.29 (s, 1H), 7.36 (m, 2H), 7.19 (s, 1H), 7.12 (m, 2H), 6.59 (s, 1H), 4.27 (m, 2H), 3.37 (m, 2H); HRMS (EI) m/z 355.07512 (M+1). Analysis for C$_{18}$H$_{12}$ClFN$_4$.O0.1H$_2$O.0.4CH$_3$CO$_2$C$_2$H$_5$: Found: C, 59.59; H, 3.66; N, 14.69. Calcd: C, 59.97; H, 3.93; N, 14.29.

EXAMPLE 8

1-[(2E)-4-Chloro-2-butenoyl]-9-(3-chloro-4-fluoroanilino)-2,3-dihydro-1H-[1,4]oxazino[3,2-g]quinoline-8-cabonitrile and 1-[(2E)-4-Bromo-2-butenoyl]-9-(3-chloro-4-fluoroanilino)-2,3-dihydro-1H-[1,4]oxazino[3,2-g]quinoline-8-carbonitrile An amount of 4-bromocrotonic acid t-butyldimethylsilyl ester (0.295 mL, 1.68 mmol) was stirred in dichloromethane (2 mL), and to this were added oxalyl chloride (0.195 mL, 2.24 mmol), and N,N-dimethylformamide (2 drops). The mixture was stirred for 2 hours and subsequently evaporated to an oil, dissolved in tetrahydrofuran (12 mL), and cooled to 0° C. This was added to a solution of 9-(3-chloro-4-fluoroanilino)-2,3-dihydro-1H-[1,4]oxazino[3,2-g]quinoline-8-carbonitrile (500 mg, 1.41 mmol) dissolved in tetrahydrofuran (20 mL), and N,N-diisopropylethylamine (0.972 mL, 5.6 mmol). After stirring at 0° C. for 3 hours, 4-N,N-dimethylaminopyridine (17 mg, 0.139 mmol) was added and the mixture was stirred for 16 hours. To this was added a second portion of 4-bromocrotonyl chloride (62 μL, 0.353 mmol), and after stirring for one hour the reaction was completed. The reaction mixture was stirred with a cold saturated sodium bicarbonate solution, and extracted with ethyl acetate. The organic layer was dried over sodium sulfate, filtered, and evaporated to yield the crude product (0.709 g). The aqeous layer was subsequently evaporated, extracted with ethyl acetate, dried over sodium sulfate, and evaporated to yield a yellow solid (0.11 g). Both crops were combined and purified by adding acetone and filtering off the pale precipitate (87.6 mg). The filtrate was purified by preparative chromatography (5% methanol in dichloromethane), to yield a second crop (0.4 g). Both were combined to give 0.488 g (72% yield) of a product which is a 1:1 mixture of the bromide and the chloride, m.p. 132–135° C.; $^1$H NMR (DMSO-d$_6$) δ 9.77 (bs, 2H), 8.79 (bs, 2H), 8.50 (s, 2H), 7.53–7.24 (m, 8H), 6.61–6.46 (m, 3H), 6.20–6.13 (m, 1H), 4.46 (m, 4H), 4.03 (m, 4H), 3.70–3.66 (m, 4H); HRMS (Cl) 501.0083 m/z (M+1). Analysis for (C$_{22}$H$_{15}$BrClFN$_4$O$_2$+C$_{22}$H$_{15}$BrCl$_2$FN$_4$O$_2$). 1.8 H$_2$O: Found: C, 52.14; H, 3.61; N, 10.85. Calcd: C, 51.97; H, 3.66; N, 11.07.

EXAMPLE 9

9-(3-Chloro-4-fluoroanilino)-1-[(2E)-4-(dimethylamino)-2-butenoyl]-2,3-dihydro-1H-[1,4]oxazino[3,2-g]quinoline-8-carbonitrile An amount of the mixture 1-[(2E)-4-chloro-2-butenoyl]-9-(3-chloro-4-fluoroanilino)-2,3-dihydro-1H-[1,4]oxazino [3,2-g]quinoline-8-carbonitrile and 1-[(2E)-4-bromo-2-butenoyl]-9-(3-chloro-4-fluoroanilino)-2,3-dihydro-1H-[1,4]oxazino[3,2-g]quinoline-8-carbonitrile (0.708 g, 1.458 mmol), was dissolved in N,N-dimethylformamide (1.89 mL), and to this was added N,N-diisopropylethylamine (0.303 mL, 1.75 mmol), and 0.875 mL (1.75 mmol) of a 2.0 M solution of dimethylamine in tetrahydrofuran The reaction mixture was stirred for one hour, stored for 16 hours in the refrigerator, and then stirred with saturated sodium bicarbonate solution and brine. The solid was filtered off and washed with acetone to give a beige product (372 mg, 52% yield); m.p. 199–200° C.; $^1$H NMR (DMSO-d$_6$) δ 9.70 (bs, 1H), 8.52 (s, 1H), 8.44 (bs, 1H), 7.47–7.37 (m, 3H), 7.25–7.23 (m, 1H), 6.86–6.79 (m, 1H), 6.62–6.57 (d, 1H), 4.44 (t, 2H), 4.06 (t, 2H), 3.02 (d, 2H), 2.06 (s, 6H); HRMS (Cl) m/z 466.1440 (M+1). Analysis for C$_{24}$H$_{21}$ClFN$_5$O$_2$.1.4H$_2$O: Found: C, 60.48; H, 4.85; N, 14.49; F, 4.02; Cl, 7.52. Calcd: C, 60.28; H, 4.73; N, 14.66; F, 3.98; Cl, 7.32.

EXAMPLE 10

9-(3-Chloro-4-fluoroanilino)-1-[4-(dimethylamino)butanoyl]-2,3-dihydro-1H-[1,4]oxazino[3,2-g]quinoline-8-carbonitrile An amount of 9-(3-chloro-4-fluoroanilino)-2,3-dihydro-1H-[1,4]oxazino[3,2-g]quinoline-8-carbonitril (400 mg, 1.13 mmol) was dissolved in tetrahydrofuran (24 mL) and cooled to 0° C. To this was added 4-chlorobutyryl chloride (0.21 mL, 1.9 mmol) and N,N-diisopropylethylamine (0.59 mL, 3.4 mmol), and the mixture was stirred at room temperature for 24 hours. To this was added ethyl acetate and sodium bicarbonate solution, and after separation of the layers, the organic layer was dried over sodium sulfate, filtered, and evaporated to a solid (0.643 g) as 9-(3-chloro-4-fluoroanilino)-1-[4-(chlorobutyryl)butanoyl]-2,3-dihydro-1H-[1,4]oxazino[3,2-g]quinoline-8-carbonitrile, which was used without further purification.

An amount of 500 mg (1.09 mmol) of 9-(3-chloro-4-fluoroanilino)-1-[4-(chlorobutyryl)butanoyl]-2,3-dihydro-1H-[1,4]oxazino[3,2-g]quinoline-8-carbonitrile was stirred in N,N-dimethylformamide (4.5 mL), and to this was added sodium iodide (0.163 g, 1.69 mmol), tetrabutylammonium iodide (0.80 g, 0.22 mmol), and dimethylamine solution in tetrahydrofuran 2M (11 mL, 21.8 mmol). The mixture was heated at 45° C. for 4 hours and stirred at room temperature for an additional 16 hours. To this was added ethyl acetate and sodium bicarbonate solution, and after separation of the layers, the organic phase was dried over sodium sulfate and evaporated to obtain the crude product. Purification of the crude product was carried out by flash chromatography (20% acetone in methanol), to give a tan solid (129 mg, 33% yield), m.p. 165° C.; $^1$H NMR (DMSO-$d_6$) δ 9.78 (bs, 1H), 8.69 (bs, 1H), 8.39 (s, 1H), 7.39 (m, 2H), 7.26 (s, 1H), 7.21 (m, 1H), 4.39 (t, 2H), 3.98 (t, 2H), 2.64 (t, 2H), 2.20 (t, 2H), 2.07 (s, 6H), 1.71 (m, 2H); HRMS (EI) m/z 467.1514 (M+1). Analysis for $C_{24}H_{23}ClFN_5O_2 \cdot 0.3H_2O \cdot 0.3C_2H_5CO_2CH_3$: Found: C, 60.22; H, 5.16; N, 14.12. Calcd: C, 60.56; H, 5.24; N, 14.01.

EXAMPLE 11

1-(4-Chlorobutyl)-9-(3-chloro-4-fluoroanilino)-2,3-dihydro-1H-[1,4]oxazino[3,2-g]quinoline-8-carbonitrile An amount of 9-(3-chloro-4-fluoroanilino)-2,3-dihydro-1H-[1,4]oxazino[3,2-g]quinoline-8-carbonitrile (650 mg, 1.84 mmol) was stirred in N,N-dimethylformamide (13 mL), and to this was added a solution of 4-chloro-butyraldehyde (2.0 g, 18.4 mmol) in trifluoroacetic acid (1.8 mL). To this was added sodium borohydride (128 mg, 3.4 mmol), portionwise, in 1.5 hours. The reaction mixture was stirred for 16 hours at room temperature, then stirred with saturated sodium bicarbonate solution, and extracted with ethyl acetate. The organic phase was washed with saturated brine solution, dried over sodium sulfate, evaporated to an oil and crashed out in hexane to yield a yellow solid (325 mg, 40%). A small portion was purified by flash chromatography (10% acetone in dichloromethane), to yield a yellow solid (112 mg, 17% yield), mp 78–79° C.; $^1$H NMR (DMSO-$d_6$) δ 9.34 (bs, 1H), 8.33 (s, 1H), 7.43 (m, 2H), 1.21 (m, 2H), 7.16 (s, 1H), 4.33 (t, 2H), 3.66 (t, 2H), 3.47 (m, 4H), 1.73 (m, 4H); HRMS (EI) 445.0987 (M+1). Analysis for $C_{22}H_{19}Cl_2FN_4O \cdot 0.5 H_2O$: Found: C, 58.22; H, 4.46; N, 12.24. Calcd: C, 58.11; H, 4.40; N, 12.33.

EXAMPLE 12

9-(3-Chloro-4-fluoroanilino)-1-[4-(dimethylamino) butyl]-2,3-dihydro-1H-[1,4]oxazino[3,2-g]quinoline-8-carbonitrile An amount of 1-(4-chlorobutyl)-9-(3-chloro-4-fluoroanilino)-2,3-dihydro-1H-[1,4]oxazino[3,2-g] quinoline-8-carbonitrile (150 mg, 0.34 mmol) was stirred in N,N-dimethylformamide (1.5 ml), and to this were added sodium iodide (76 mg, 0.51 mmol), tetrabutyl ammonium iodide (25.9 mg, 0.07 mmol), and dimethylamine in tetrahydrofuran (2M) (5.4 mL, 10.8 mmol). The mixture was heated at 45° C. for 4 hours, cooled to room temperature, and stirred with ethyl acetate and saturated sodium bicarbonate solution. After separation of the layers, the organic layer was dried over sodium sulfate and evaporated to an oil. Purification was performed by preparative thin layer chromatography (60% acetone in methanol) to give a yellow solid (89 mg, 58% yield), m.p. 105° C.; $^1$H NMR (DMSO-$d_6$) δ 9.50–9.00 (bs, 1H), 8.20 (s, 1H), 7.33 (t, 1H), 7.26 (dd, 1H), 7.23 (s, 1H), 7.07 (m, 2H), 4.30 t, 2H), 3.37 (m, 4H), 2.18 (t, 2H), 2.06 (s, 6H), 1.55 (m, 2H), 1.40 (m, 2H); HRMS (EI) m/z 453.1736 (M+1).

EXAMPLE 13

2-Methoxy-5-nitroacetanilide

To a stirred solution of 90 g (0.54 mol) of 2-methoxy-5-nitroaniline in 1100 mL of water was slowly added acetic acid (200 mL, 2.12 mol) at room temperature. The reaction mixture was stirred at room temperature for 1.5 hour, and subsequently filtered. The solid was washed with water, ether, and dried to give 133 g of crude yellow product (90% yield), mp 172–177° C.; $^1$H NMR (DMSO-$d_6$) δ 9.56 (s, 1H), 9.00 (d, J=3 Hz, 1H), 8.02 (dd, J=3 Hz, 9 Hz, 1H), 7.26 (d, J=9 Hz, 1H), 3.99 (s, 3H), 2.15 (s, 3H); MS (ES) n/z 211.1 (M+1).

EXAMPLE 14

N-(5-Amino-2-methoxyphenyl)acetamide

An amount of 30 g (0.14 mol) of 2-methoxy-5-nitroacetanilide was dissolved in 750 mL of methanol and 195 mL of water, and to this was added at room temperature 40 g (0.72 mol) of iron powder, and 53 g (0.99 mol) of ammonium chloride. The suspension was heated at 50° C. for 0.5 hour, then cooled to room temperature and filtered. The residue was washed with ethyl acetate, and the combined filtrate was evaporated to dryness. The solid was basified with saturated sodium bicarbonate solution, and extracted with ethyl acetate. The organic phase was dried over magnesium sulfate and evaporated to dryness to yield a brown solid (21 g, 83% yield), mp 83° C.; $^1$H NMR (DMSO-$d_6$) δ 8.85 (bs, 1H), 7.32 (d, J=2 Hz, 1H), 6.71 (d, J=8 Hz, 1H), 6.24 (dd, J=2 Hz, 8 Hz, 1H), 4.64 (s, 2H), 3.68 (s, 3H), 2.05 (s, 3H); MS (ES) m/z 181.1 (M+1). Analysis for $C_9H_{12}N_2O_2$: Found: C, 59.65; H, 6.63; N, 15.23. Calcd: C, 59.99; H, 6.71; N, 15.55.

EXAMPLE 15

Ethyl (E)-3-[3-(Acetylamino)-4-methoxyanilino]-2-cyano-2-propenoate and Ethyl (Z)-3-[3-(Acetylamino)-4-methoxyanilino]-2-cyano-2-propenoate An amount of 4.95 g (0.0275 mol) of N-(5-amino-2-methoxyphenyl)acetamide was heated with 2-cyano-3-ethoxy-acrylic acid ethyl ester (4.74 g, 0.028 mol), at 120° C. for 2 hours. A crystalline brown solid was formed and the reaction mixture was evaporated to dryness to give a brown solid which is a mixture of E and Z isomers (7.9 g, 95% yield), mp 155–160° C.; $^1$H NMR (DMSO-$d_6$) δ 10.85, 10.65 (dd, J=14 Hz, 1H), 9.23 (d, J=10 Hz, 1H), 8.31–8.00 (m, 2H), 7.23–7.02 (m, 2H), 4.26–4.13 (m, 2H), 3.83 (s, 3H), 2.106 (s, 3H), 1.44–1.29 (m, 3H); HRMS (EI) m/z 304.1290 (M+1). Analysis for $C_{15}H_{17}N_3O_4$: Found: C, 59.03; H, 5.51; N, 13.55. Calcd: C, 59.40; H, 5.65; N, 13.85.

EXAMPLE 16

N-(3-Cyano-6-methoxy-4-oxo-1,4-dihydro-7-quinolinyl)acetamide

An amount of 1 g (0.003 mol) of a mixture of ethyl (E)-3-[3-(acetylamino)-4-methoxyanilino]-2-cyano-2-propenoate and ethyl (Z)-3-[3-(acetylamino)-4-methoxyanilino]-2-cyano-2-propenoate was added to a stirring solution of biphenyl (16.3 mL, 0.10 mol) and phenyl ether (48.8 mL, 0.30 mol) at 256° C. After stirring for 2 hours at 256° C., the reaction mixture was cooled to room temperature, diluted with diethyl ether (130 mL), filtered, and evaporated to dryness to give a gray solid (0.53 g, 62% yield), mp 305–310° C.; $^1$H NMR (DMSO-$d_6$) δ 12.80 (s, 1H), 9.58 (s, 1H), 8.62 (s, 1H), 8.58 (m, 1H), 7.52 (s, 1H), 3.97 (s, 3H), 2.20 (s, 3H); HRMS (EI) m/z 257.0793 (M+1).

EXAMPLE 17

N-(4-Chloro-3-cyano-6-methoxy-7-quinolinyl)acetamide

An amount of 10 g (0.039 mol) of N-(3-cyano-6-methoxy-4-oxo-1,4-dihydro-7-quinolinyl)acetamide was subsequently stirred in 29 mL (0.31 mol) of phosphorus oxychloride, heated at 100° C. for 0.5 hours, and cooled to 0° C. To this was slowly added a saturated solution of sodium bicarbonate and ethyl acetate. After separation of the layers, the organic layer was washed with saturated brine, dried over sodium sulfate, and evaporated to give a brown solid (9.8 g, 73% yield), mp 230–235° C.; $^1$H NMR (DMSO-$d_6$) δ 9.77 (s, 11–1), 8.98 (s, 1H), 8.94 (s, 1H), 7.50 (s, 1H), 4.11 (s, 3H), 2.25 (s, 3H); HRMS (EI) m/z 275.0466 (M+1). Analysis for $C_{13}H_{10}ClN_3O_2 \cdot 0.75H_2O$: Found: C, 53.99; H, 3.83; N, 14.53. Calcd: C, 53.62; H, 3.68; N, 14.98.

EXAMPLE 18

N-[3-Cyano-4-(2,4-dichloro-5-methoxyanilino)-6-methoxy-7-quinolinyl]acetamide

An amount of 9.7 g (0.035 mol) of N-(4-chloro-3-cyano-6-methoxy-7-quinolinyl)acetamide was stirred in 97 ml of 2-ethoxyethanol. To this were added 2,4-dichloro-5-methoxyaniline (7.4 g, 0.038 mol), and 4.1 g (0.035 mol) pyridine hydrochloride, and the mixture was heated at 135° C. for 3 hours. The solvent was evaporated and the solid was stirred in saturated sodium bicarbonate solution and extracted with ethyl acetate. The organic phase was washed with saturated brine solution, dried over sodium sulfate and evaporated to dryness to give a brown solid (10.7 g, 71% yield), mp 267–270° C.; $^1$H NMR (DMSO-$d_6$) δ 9.94 (s, 1H), 9.01 (s, 1H), 8.99 (s, 1H), 8.42 (s, 1H), 7.97 (m, 1H), 7.86 (s, 1H), 7.53 (m, 1H), 4.12 (s, 3H), 3.88 (s, 3H), 2.27 (s, 3H); MS (ES) m/z 431.1 (M+1). Analysis for $C_{20}H_{16}Cl_2N_4O_3 \cdot 7H_2O$: Found: C, 43.23; H, 3.35; N, 10.24. Calcd: C, 43.06; H, 5.38; N, 10.05.

EXAMPLE 19

7-Amino-4-(2,4-dichloro-5-methoxyanilino)-6-methoxy-3-quinolinecarbonitrile

An amount of 5 g (0.012 mol) of N-[3-cyano-4-(2,4-dichloro-5-methoxyanilino)-6-methoxy-7-quinolinyl]acetamide was stirred in 37% hydrochloric acid (500 mL), and heated at 65° C. for 1 hour. The mixture was evaporated to a slurry, stirred in saturated sodium bicarbonate solution, and extracted with ethyl acetate. The organic phase was dried over sodium sulfate, filtered through a pad of silica gel, and evaporated to dryness to give a tan solid (1.9 g, 42% yield), mp 265° C. decomp.; $^1$H NMR (DMSO-$d_6$) δ 9.29 (s, 1H), 8.27 (s, 1H), 7.70 (s, 1H), 7.66 (s, 1H), 7.23 (s, 1H), 6.98 (s, 1H), 5.93 (s, 2H), 3.96 (s, 3H), 3.84 (s, 3H); MS (ES) m/z 389.2 (M+1). Analysis for $C_{18}H_{14}Cl_2N_4O_2$: Found: C, 55.80; H, 3.78; N, 14.67. Calcd: C, 55.54; H, 3.63; N, 14.39.

EXAMPLE 20

N-[3-Cyano-4-(2,4-dichloroanilino)-6-methoxy-7-quinolinyl]acetamide

An amount of 6 g .(0.022 mol) of N-(4-chloro-3-cyano-6-methoxy-7-quinolinyl)acetamide was stirred in 60 ml of 2-ethoxyethanol. To this were added 2,4-dichlorophenylamine (3.9 g, 0.024 mol), and 2.8 g (0.024 mol) pyridine hydrochloride, and the mixture was heated at 135° C. for 3 hours. The solvent was evaporated and the solid was stirred in ethyl acetate and filtered to give the HCl salt (8.1 g, 84%). A small portion was stirred in ethyl acetate and sodium hydroxide (1M). After separation of the layers, the organic layer was washed with saturated brine solution, dried over sodium sulfate, and evaporated to dryness to give a yellowish solid (92 mg, 1% yield), mp 245–246° C.; $^1$H NMR (DMSO-$d_6$) δ 9.65 (s, 1H), 9.56 (s, 1H), 8.72 (s, 1H), 8.43 (s, 1H), 7.90 (s, 1H), 7.80 (m, 1H), 7.53 (m, 2H), 4.04 (s, 3H), 2.22 (s, 3H); HRMS (EI) m/z 401.05647 (M+1). Analysis for $C_{19}H_{14}Cl_2N_4O_2 \cdot 0.1H_2O$: Found: C, 56.35; H, 3.42; N, 13.67. Calcd: C, 56.57; H, 3.52; N, 13.89.

EXAMPLE 21

7-Amino-4-(2,4-dichloroanilino)-6-hydroxy-3-quinolinecarbonitrile

An amount of 200 mg (0.50 mmol) of N-[3-cyano-4-(2,4-dichloroanilino)-6-methoxy-7-quinolinyl]acetamide, was stirred with pyridine hydrochloride (1.4 g, 12.5 mmol), and heated at 200° C. for 2 hours. The mixture was cooled to room temperature, stilled with ethyl acetate and saturated sodium bicarbonate solution, and filtered. The layers were separated, and the organic layer was subsequently washed with saturated brine solution, dried over sodium sulfate, and evaporated to a yellow oil. Purification was carried out by preparative thin layer chromatography (5% methanol in ethyl acetate), to yield a yellow solid (52 mg, 30% yield), mp 265° C. decomp.; $^1$H NMR (DMSO-$d_6$) δ 10.26 (bs, 1H), 8.93 (s, 1H), 8.34 (s, 1H), 7.66 (d, J=2 Hz, 1H), 7.35 (dd, J=9Hz, J=2Hz, 1H), 7.32 (s, 1H), 7.10 (d, J=9 Hz, 1H), 6.99 (s, 1H), 5.90 (s, 2H); HRMS (EI) m/z 344.0897 (M+1). Analysis for $C_{16}H_{10}Cl_2N_4O \cdot 0.5CH_3OH$: Found: C, 54.43; H, 3.12; N, 15.34. Calcd: C, 54.74; H, 3.32; N, 15.48.

EXAMPLE 22

9-(2,4-Dichloroanilino)-3,4-dihydro-2H-[1,4]oxazino[2,3-g]quinoline-8-carbonitrile An amount of 1100 mg (3.2 mmol) of 7-amino-4-(2,4-dichloroanilino)-6-hydroxy-3-quinolinecarbonitrile was stirred in 2-ethoxyethanol (250 mL), and to this were added 1,2-dibromoethane (6.5 g, 34 mmol), and potassium carbonate (2.7 g, 19.2 mmol). The mixture was heated at 150° C. for 0.5 hours, cooled to room temperature, and filtered through a Magnesol pad. The filtrate was evaporated to a brown oil, taken up in ethyl acetate and basified with saturated sodium bicarbonate solution. After separation of the layers, the organic layer was washed with saturated brine solution, dried over sodium sulfate, and evaporated to a brown oil. Purification was carried out by flash chromatography (ethyl acetate), to give a yellow solid (175 mg, 15% yield), mp 254–255° C.; $^1$H NMR (DMSO-$d_6$) δ 9.20 (s, 1H), 8.25 (s, 1H), 7.70 (dd, 2H), 7.41 (dd, 2H), 7.14 (s, 1H), 6.92 (s, 1H), 4.23 (t, 2H), 3.43 (t, 2H); I-IRMS (EI) m/z 371.04502 (M+1). Analysis for $C_{18}H_{12}Cl_2N_4O.0.1CH_3CO_2C_2H_5$: Found: C, 58.03; H, 3.45; N, 14.49. Calcd: C, 58.10; H, 3.37; N, 14.74.

EXAMPLE 23

4-(4-Chlorobutyl)-9-(2,4-dichloroanilino)-3,4-dihydo-2H-[1,4]oxazino[2,3-g]quinoline-8-carbonitrile An amount of 100 mg (0.27 mmol) of 9-(2,4-dichloroanilino)-3,4-dihydro-2H-[1,4]oxazino[2,3-g]quinoline-8-carbonitrile, was stirred in N,N-dimethylformamide (2 mL), and to this was added a solution of 4-chloro-butyraldehyde (719 mg, 6.8 mmol) in tetrahydrofuran (2 mL) and trifluoroacetic acid (1.4 mL). The reaction mixture was stirred at room temperature, and to this was added sodium borohydride (128 mg, 3.4 mmol) portionwise, in 1.5 hours. The mixture was stirred for 16 hours, basified with saturated sodium bicarbonate solution, and extracted with ethyl acetate. After separation of the layers, the organic layer was washed with saturated brine solution, dried over sodium sulfate and evaporated to an oil. Purification was done by flash chromatography (10% acetone in dichloromethane) to give a yellow solid (66 mg, 53% yield), m.p 56–57° C.; $^1$H NMR (DMSO-$d_6$) δ 9.92 (bs, 1H), 8.59 (s, 1H), 7.81 (d, 2H), 7.51 (m, 2H), 6.98 (s, 1H), 4.30 (t, 2H), 3.70 (t, 2H), 3.57 (t, 2H), 3.51 (t, 2H), 1.80 (m, 4H); HRMS (EI) m/z 461.06917 (M+1). Analysis for $C_{22}H_{19}Cl_3N_4O.0.7CH_3CO_2C_2H_5.3.9H_2O$ Found: C, 49.81; H, 3.78; N, 9.65. Calcd: C, 50.12; H, 5.46; N, 9.43.

EXAMPLE 24

9-(2,4-Dichloroanilino)-4-[4-(4-ethyl-1-piperazinyl)butyl]-3,4-dihydio-2H-[1,4]oxazino[2,3-g]quinoline-8-carbonitrile An amount of 120 mg (0.26 mmol) of 4-(4-chlorobutyl)-9-(2,4-dichloroanilino)-3,4-dihydro-2H-[1,4]oxazino[2,3-g]quinoline-8-carbonitrile was stirred in N,N-dimethylformamide (0.8 mL), and to this were aided sodium iodide (55 mg, 0.36 mmol), tetrabutylammonium iodide (58 mg, 0.16 mmol), and 1-ethylpiperazine (0.26 mL, 2.1 mmol). The mixture was heated at 50° C. for three hours, after which an additional amount of 1-ethylpiperazine (0.26 mL, 2.1 mmol), was added. The mixture was heated at 60° C. for 3 hours, and subsequently evaporated to a yellow oil, stirred with saturated sodium bicarbonate solution, and extracted with dichloromethane. The organic layer was washed with saturated brine solution, dried over sodium sulfate, and evaporated to a yellow oil. Purification was performed by flash chromatography (10% acetone in dichloromethane, then 70:30:5=dichloromethane: methanol: ammonium hydroxide), to give a yellow solid (74 mg, 53% yield), m.p 97–98° C.; $^1$H NMR (DMSO-$d_6$) δ 9.21 (s, 1H), 8.27 (s, 1H), 7.73 (d, 1H), 7.68 (s, 1H), 7.42 (dd, 2H), 6.70 (s, 1H), 4.27 (t, 2H), 3.49 (m, 4H), 2.31 (m, 12H), 1.62 (dd, J=7 Hz, 2H), 1.52 (dd, J=7 Hz, 2H), 0.97 (t, 3H); Analysis for $C_{28}H_{32}Cl_2N_6O.0.3CH_3CO_2C_2H_5.1H_2O$ Found: C, 60.29; H, 5.94; N, 14.76. Calcd: C, 60.00; H, 6.23; N, 14.38.

What is claimed is:
1. A compound of Formula (I)

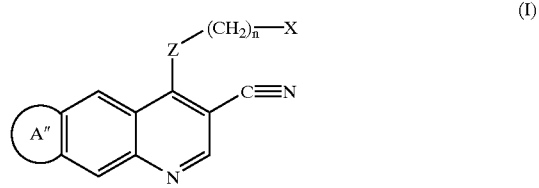

wherein:
Z is —NH—, —O—, —S(O)$_a$—, or —NR—;
R is alkyl of 1 to 6 carbon atoms, or carboalkyl of 2 to 7 carbon atoms;
X is cycloalkyl of 3 to 7 carbon atoms, which may be optionally substituted with one or more alkyl of 1 to 6 carbon atom groups; or
X is pyridinyl, pyrimidinyl, or an aryl ring; wherein the pyridinyl, pyrimidinyl or aryl ring may be optionally mono-, di-, or tri-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or
X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

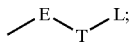

E is pyridinyl, pyrimidinyl, or an aryl ring; wherein the pyridinyl, pyrimidinyl or aryl ring may be optionally mono-, di-, or tri-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at a carbon and is
—NH(CH$_2$)$_m$—, —O(CH$_2$)$_m$—, —S(O)$_a$—(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S(O)$_a$—, or —(CH$_2$)$_m$NR—;

L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 t o 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A" is a moiety selected from the group

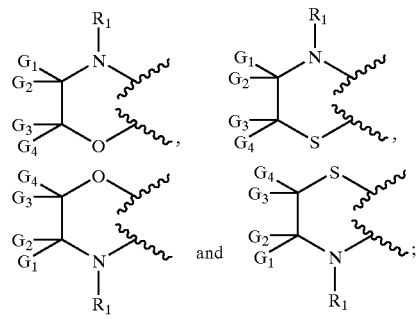

$G_1$, $G_2$, $G_3$ and $G_4$ are independently selected from the group consisting of hydrogen, and alkyl of 1 to 6 carbon atoms;
$R_1$ is —H, $R_{11}$—CH$_2$—, —$R_{12}$,

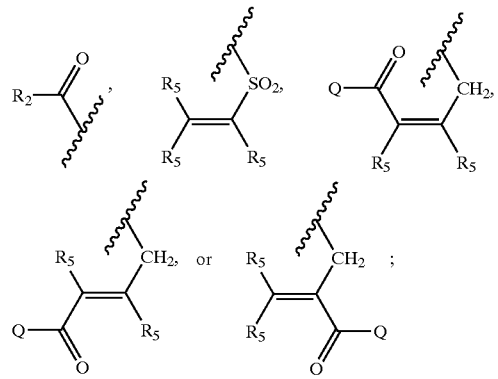

$R_{11}$ is —H, alkyl of 1 to 5 carbon atoms, aryl, or $R_{13}$—(C(R$_6$)$_2$)$_k$—;
$R_{13}$ is

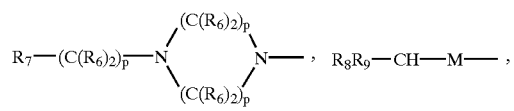

$R_7$—, $R_7$—(C(R$_6$)$_2$)$_p$—M—, or Het-(C(R$_6$)$_2$)$_q$—W—,
$R_7$ is —H, —NR$_6$R$_6$, —OR$_6$, —J, —N(R$_6$)$_3$$^+$, or —NR$_6$(OR$_6$);

M is 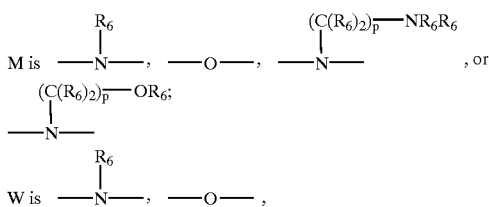

or a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, and tetrahydropyran, optionally mono- or di-substituted on carbon by —$R_6$, hydroxy, —$N(R_6)_2$, —$OR_6$, —$(C(R_6)_2)_sOR_6$, or —$(C(R_6)_2)_sN(R_6)_2$; or optionally mono-substituted on nitrogen with —$R_6$; and optionally mono or di-substituted on a saturated carbon with divalent radicals —O—, or —$O(C(R_6)_2)_sO$—;

$R_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms,

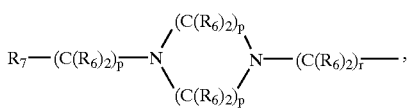

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)2)_rOR_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;

Q' is alkyl of 1 to 6 carbon atoms;

$R_2$ is selected from the group consisting of

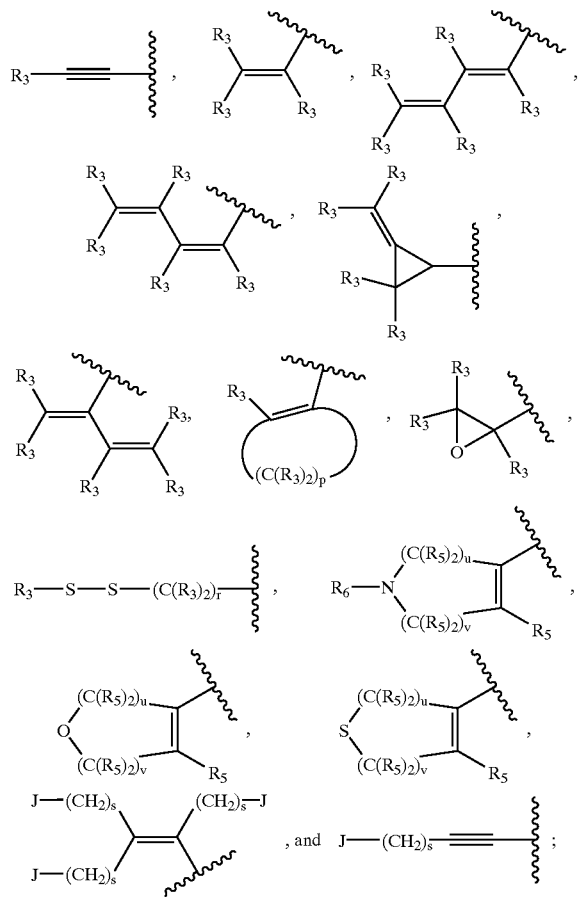

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;

$R_{3a}$ is

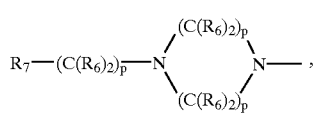

$R_7$—, $R_7$—$(C(R_6)_2)_p$—M—, $R_8R_9$—CH—M—, or Het-$(C(R_6)_2)_q$—W—;

a is 0 to 2;
k is 1,3 to 5;
n is 0 to 1;
m is 0 to 3;
p is 2 to 4;
q is 0 to 4;
r is 1 to 4;
s is 1 to 6;
u is 0 to 4 and v is 0 to 4, wherein the sum of u+v is 2 to 4;

provided that:
a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;

b. when $R_3$ is bound to sulfur, $R_3$ is not —H, carboxy, carboalkoxy, or carboalkyl;
c. when M is —O—, and $R_7$ is —$OR_6$, then p is 1 to 4;
d. when M is —O—, then k is 1 to 5;
e. when W is —O—, then k is 1 to 5;
f. when $R_7$ is —$OR_6$, then k is 1 to 5;
g. when W is not a bond with Het bonded through a nitrogen atom, q is 2 to 4, and when W is a bond, q is 0;

or a pharmaceutically acceptable salt thereof.

2. A compound according to claim 1 wherein Z is —NH—, n is 0, X is aryl and A" is the moiety

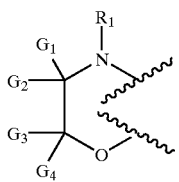

or a pharmaceutically acceptable salt thereof.

3. A compound according to claim 1, wherein Z is —NH—, n is 0, X is aryl and A" is the moiety

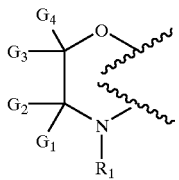

or a pharmaceutically acceptable salt thereof.

4. A compound according to claim 1, wherein Z is —NH—, n is 0, X is aryl and A" is the moiety

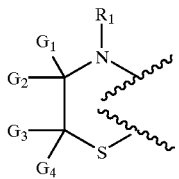

or a pharmaceutically acceptable salt thereof.

5. A compound according to claim 1, wherein Z is —NH—, n is 0, X is aryl and A" is the moiety

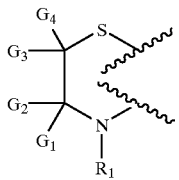

or a pharmaceutically acceptable salt thereof.

6. A compound according to claim 1, wherein Z is —NH—, n is 0, X is aryl and A" is the moiety

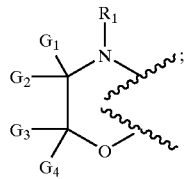

$G_1$, $G_2$, $G_3$, and $G_4$ are H;
or a pharmaceutically acceptable salt thereof.

7. A compound according to claim 1, wherein Z is —NH—, n is 0, X is aryl and A" is the moiety

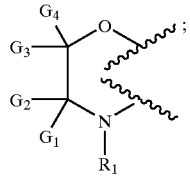

$G_1$, $G_2$, $G_3$, and $G_4$ are H;
or a pharmaceutically acceptable salt thereof.

8. A compound according to claim 1 wherein Z is —NH—, n is 0, X is aryl and A" is the moiety

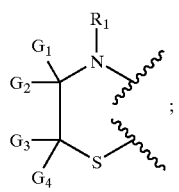

$G_1$, $G_2$, $G_3$, and $G_4$ are H;
or a pharmaceutically acceptable salt thereof.

9. The compound according to claim 1, wherein Z is —NH—, n is 0, X is aryl and A" is the moiety

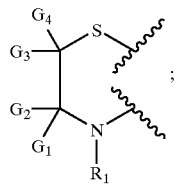

$G_1$, $G_2$, $G_3$, and $G_4$ are H;
or a pharmaceutically acceptable salt thereof.

10. A compound according to claim 1, wherein Z is —NH—, n is 0, X is aryl and A" is the moiety

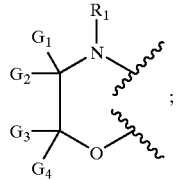

$R_1$ is selected from H, $R_2C(O)$— and $R_{11}$-$CH_2$—;
or a pharmaceutically acceptable salt thereof.

11. A compound according to claim 1, wherein Z is —NH—, n is 0, X is aryl and A" is the moiety

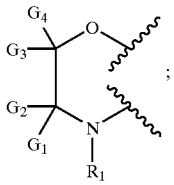

$R_1$ is selected from H, $R_2C(O)$— and $R_{11}$—$CH_2$—;
or a pharmaceutically acceptable salt thereof.

12. A compound according to claim 1, wherein Z is —NH—, n is 0, X is aryl and A" is the moiety

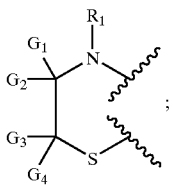

$R_1$ is selected from H, $R_2C(O)$— and $R_{11}$—$CH_2$—;
or a pharmaceutically acceptable salt thereof.

13. A compound according to claim 1, wherein Z is —NH—, n is 0, X is aryl and A" is the moiety

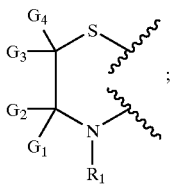

$R_1$ is selected from H, $R_2C(O)$— and $R_{11}$—$CH_2$—;
or a pharmaceutically acceptable salt thereof.

14. A compound according to claim 1, wherein Z is —NH—, n is 0, X is aryl and A" is the moiety

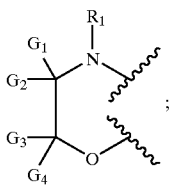

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

15. A compound according to claim 1, wherein Z is —NH—, n is 0, X is aryl and A" is the moiety

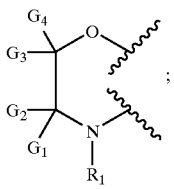

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

16. A compound according to claim 1, wherein Z is —NH—, n is 0, X is aryl and A" is the moiety

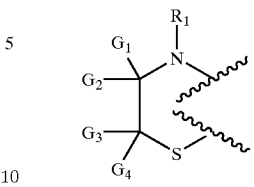

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

17. A compound according to claim 1, wherein Z is —NH—, n is 0, X is aryl and A" is the moiety

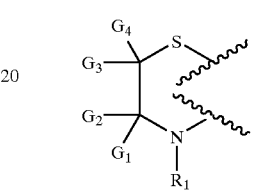

$R_1$ is selected from H, $R_2C(O)$— and $R_{11}$—$CH_2$—;
$G_1$, $G_2$, $G_3$, and $G_4$ are H;
or a pharmaceutically acceptable salt thereof.

18. The compound of claim 1, which is 9-(3-Chloro-4-fluoroanilino)-2,3-dihydro-1H-[1,4]oxazino[3,2-g]quinoline-8-carbonitrile or a pharmaceutically acceptable salt thereof.

19. The compound of claim 1, which is 1-[(2E)-4-Chloro-2-butenoyl]-9-(3-chloro-4-fluoroanilino)-2,3-dihydro-1H-[1,4]oxazino[3,2-g]quinoline-8-carbonitrile or a pharmaceutically acceptable salt thereof.

20. The compound according to claim 1, which is 1-[(2E)-4-Bromo-2-butenoyl]-9-(3-chloro-4-fluoroanilino)-2,3-dihydro-1H-[1,4]oxazino[3,2-g]quinoline-8-carbonitrile or a pharmaceutically acceptable salt thereof.

21. The compound according to claim 1, which is 9-(3-Chloro-4-fluoroanilino)-1-[(2E)-4-(dimethylamino)-2-butenoyl]-2,3-dihydro-1H-[1,4]oxazino[3,2-g]quinoline-8-carbonitrile or a pharmaceutically acceptable salt thereof.

22. The compound according to claim 1, which is 9-(3-Chloro-4-fluoroanilino)-1-[4-(dimethylamino)butanoyl]-2,3-dihydro-1H-[1,4]oxazino[3,2-g]quinoline-8-carbonitrile or a pharmaceutically acceptable salt thereof.

23. The compound according to claim 1, which is 1-(4-Chlorobutyl)-9-(3-chloro-4-fluoroanilino)-2,3-dihydro-1H-[1,4]oxazino[3,2-g]quinoline-8-carbonitrile or a pharmaceutically acceptable salt thereof.

24. The compound according to claim 1, which is 9-(3-Chloro-4-fluoroanilino)-1-[4-(dimethylamino)butyl]-2,3-dihydro-1H-[1,4]oxazino[3,2-g]quinoline-8-carbonitrile or a pharmaceutically acceptable salt thereof.

25. The compound according to claim 1, 9-(2,4-Dichloroanilino)-3,4-dihydro-2H-[1,4]oxazino[2,3-g]quinoline-8-carbonitrile or a pharmaceutically acceptable salt thereof.

26. The compound according to claim 1, 4-(4-Chlorobutyl)-9-(2,4-dichloroanilino)-3,4-dihydio-2H-[1,4]oxazino[2,3-g]quinoline-8-carbonitrile or a pharmaceutically acceptable salt thereof.

27. The compound of claim 1, which is 9-(2,4-Dichloroanilino)-4-[4-(4-ethyl-1-piperazinyl)butyl]-3,4-dihydro-2H-[1,4]oxazino[2,3-g]quinoline-8-carbonitnile, or a pharmaceutically acceptable salt thereof.-

28. A pharmaceutical composition comprising a compound of Formula (I)

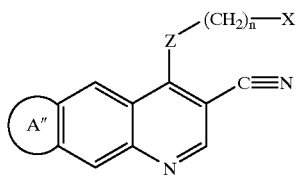

wherein:
Z is —NH—, —O—, —S(O)$_a$—, or —NR—;
R is alkyl of 1 to 6 carbon atoms, or carboalkyl of 2 to 7 carbon atoms;
X is cycloalkyl of 3 to 7 carbon atoms, which may be optionally substituted with one or more alkyl of 1 to 6 carbon atom groups; or
X is pyridinyl, pyrimidinyl, or an aryl ring; wherein the pyridinyl, pyrimidinyl or aryl ring may be optionally mono-, di-, or tri-substituted with a substituent independently selected from the group consisiting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or
X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

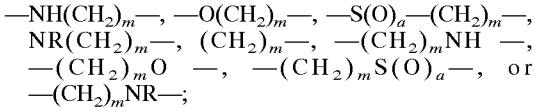

E is pyridinyl, pyrimidinyl, or an aryl ring; wherein the pyridinyl, pyrimidinyl or aryl ring may be optionally mono-, di-, or tri-substituted with a substituent selected from the group consisiting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;
T is substituted on E at a carbon and is
—NH(CH$_2$)$_m$—, —O(CH$_2$)$_m$—, —S(O)$_a$—(CH$_2$)$_m$—, NR(CH$_2$)$_m$—, (CH$_2$)$_m$—, —(CH$_2$)$_m$NH —, —(CH$_2$)$_m$O —, —(CH$_2$)$_m$S(O)$_a$—, or —(CH$_2$)$_m$NR—;
L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or
L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A" is a moiety selected from the group

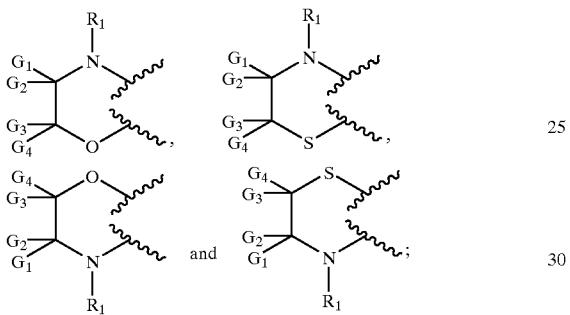

$G_1$, $G_2$, $G_3$ and $G_4$ are independently selected from the group consisting of hydrogen, and alkyl of 1 to 6 carbon atoms;

$R_1$ is —H, $R_{11}$—$CH_2$—, —$R_{12}$,

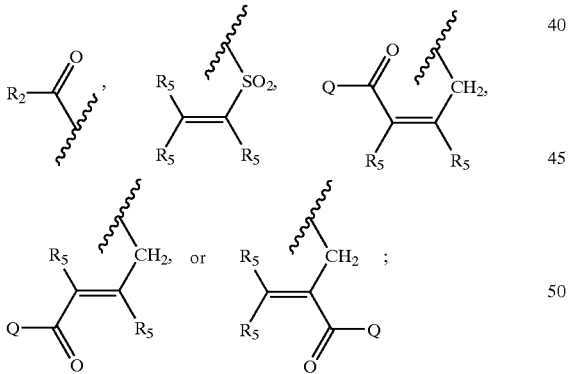

$R_{11}$ is —H, alkyl of 1 to 5 carbon atoms, aryl, or $R_{13}$—$(C(R_6)_2)_k$—;

$R_{13}$ is

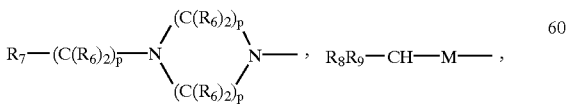

$R_7$—$R_7(C(R_6)_2)_p$—M— or Het-$(C(R_6)_2)_q$—W—;
$R_7$ is —H, —$NR_6R_6$, —$OR_6$, —J, —$N(R_6)_3^+$, or —$NR_6(OR_6)$;

M is

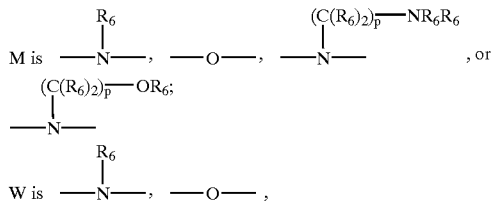

W is

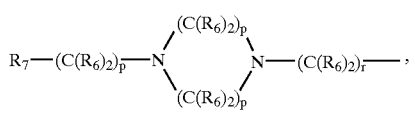

or a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, optionally mono- or di-substituted on carbon by —$R_6$, hydroxy, —$N(R_6)_2$, —$OR_6$ —$(C(R_6)_2)_sOR_6$, or —$(C(R_6)_2)_sN(R_6)_2$; or optionally mono-substituted on nitrogen with —$R_6$; and optionally mono or di-substituted on a saturated carbon with divalent radicals —O—, or —$O(C(R_6)_2)_sO$—;

$R_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1–3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms, $R_7$—$(C(R_6)_2)_p$—N$\begin{matrix}(C(R_6)_2)_p\\(C(R_6)_2)_p\end{matrix}$N—$(C(R_6)_2)_r$—, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)2)_rOR_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;
Q' is alkyl of 1 to 6 carbon atoms;
$R_2$ is selected from the group consisting of

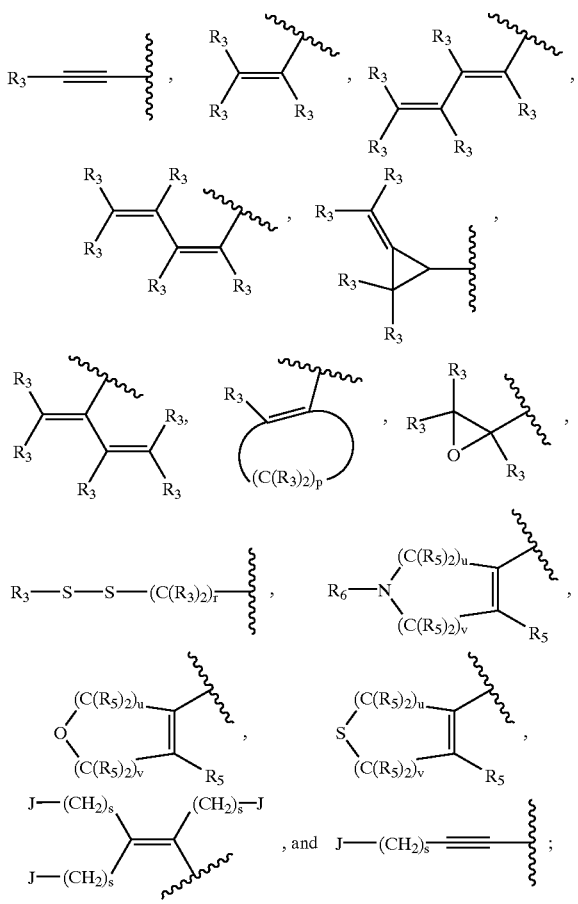

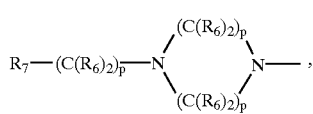

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;
$R_{3a}$ is

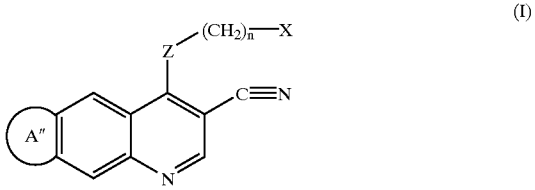

$R_7$—, $R_7$—$(C(R_6)_2)_p$—M—, $R_8R_9$—CH—M—, or Het-$(C(R_6)_2)_q$—W—,
a is 0–2;
k is 1, 3–5;
n is 0–1;
m is 0–3;
p is 2–4;
q is 0–4;
r is 1–4;
s is 1 to 6;
u is 0–4 and v is 0–4, wherein the sum of u+v is 2–4;
provided that:
  a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
  b. when $R_3$ is bound to sulfur, $R_3$ is not —H, carboxy, carboalkoxy, or carboalkyl;
  c. when M is —O—, and $R_7$ is —$OR_6$, then p is 1–4;
  d. when M is —O—, then k is 1 to 5;
  e. when W is —O—, then k is 1 to 5;
  f. when $R_7$ is —$OR_6$, then k is 1 to 5;
  g. when W is not a bond with Het bonded through a nitrogen atom, q is 2–4, and when W is a bond, q is 0;
or a pharmaceutically acceptable salt thereof and one or more pharmaceutically acceptable carriers or excipients.

29. A method of treating, inhibiting the growth of, or eradicating a neoplasm in a mammal in need thereof which comprises providing to said mammal an effective amount of a compound of Formula (I)

wherein:
Z is —NH—, —O—, —S(O)$_a$—, or —NR—;
R is alkyl of 1 to 6 carbon atoms, or carboalkyl of 2 to 7 carbon atoms;
X is cycloalkyl of 3 to 7 carbon atoms, which may be optionally substituted with one or more alkyl of 1 to 6 carbon atom groups; or
X is pyridinyl, pyrimidinyl, or an aryl ring; wherein the pyridinyl, pyrimidinyl or aryl ring may be optionally mono-, di-, or tri-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or
X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, methylmercapto, and benzoylamino; or X is the radical

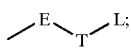

E is pyridinyl, pyrimidinyl, or an aryl ring; wherein the pyridinyl, pyrimidinyl or aryl ring may be optionally mono-, di-, or tri-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at a carbon and is
—NH(CH$_2$)$_m$—, —O(CH$_2$)$_m$—, —S(O)$_a$—(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S(O)$_a$—, or —(CH$_2$)$_m$NR—;

L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A" is a moiety selected from the group

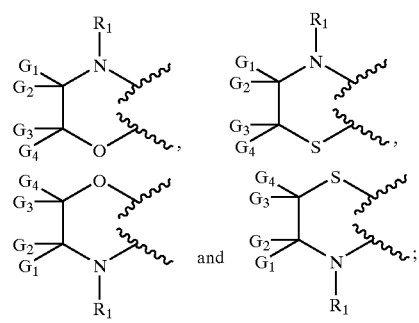

$G_1$, $G_2$, $G_3$ and $G_4$ are independently selected from the group consisting of hydrogen, and alkyl of 1 to 6 carbon atoms;

$R_1$ is —H, $R_{11}$—CH$_2$—, —$R_{12}$,

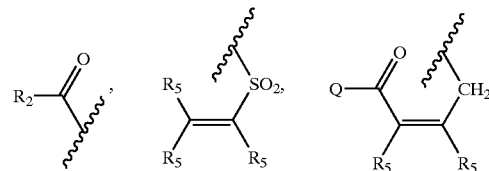

-continued

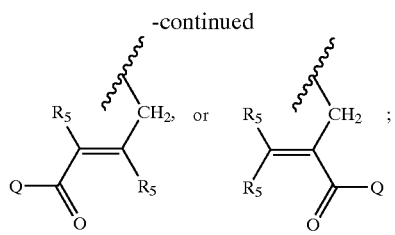

$R_{11}$, is —H, alkyl of 1 to 5 carbon atoms, aryl, or $R_{13}$—$(C(R_6)_2)_k$—;

$R_{13}$ is

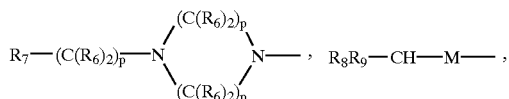

$R_7$—, $R_7$—$(C(R_6)_2)_p$—M—, or Het-$(C(R_6)_2)_q$—W—;

$R_7$ is —H, —$NR_6R_6$, —$OR_6$, —J, —$N(R_6)_3{}^+$ or —$NR_6(OR_6)$;

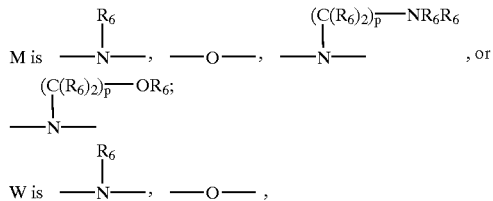

or a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, and tetrahydropyran, optionally mono- or di-substituted on carbon by —$R_6$, hydroxy, —$N(R_6)_2$, —$OR_6$, —$(C(R_6)_2)_sOR_6$, or —$(C(R_6)_2)_sN(R_6)_2$; or optionally mono-substituted on nitrogen with —$R_6$; and optionally mono or di-substituted on a saturated carbon with divalent radicals —O—, or —$O(C(R_6)_2)_sO$—;

$R_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms,

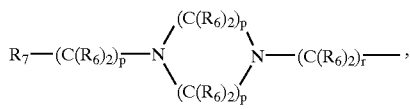

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)_2)_r$ $OR_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;

Q' is alkyl of 1 to 6 carbon atoms;

$R_2$ is selected from the group consisting of

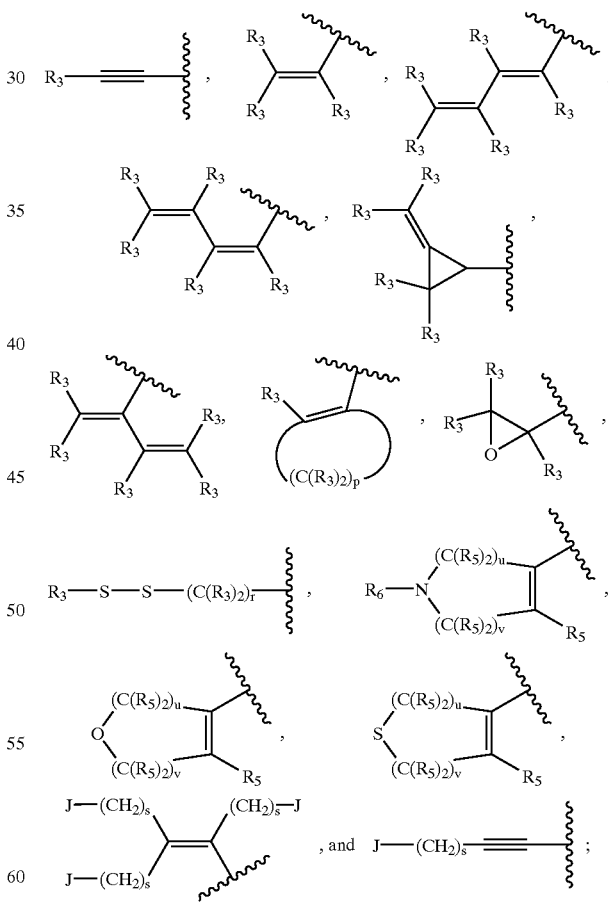

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;

$R_{3a}$ is

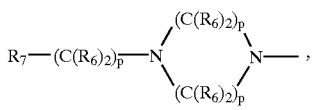

$R_7$—, $R_7$—$(C(R_6)_2)_p$—M—, $R_8R_9$—CH—M—, or Het-$(C(R_6)_2)_q$—W—;

k is 1,3 to 5;
n is 0 to;
m is 0 to 3;
p is 2 to 4;
q is 0 to 4;
r is 1 to 4;
s is 1 to 6;
u is 0 to 4 and v is 0 to 4, wherein the sum of u+v is 2 to 4;
provided that:
  a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
  b. when $R_3$ is bound to sulfur, $R_3$ is not —H, carboxy, carboalkoxy, or carboalkyl;
  c. when M is —O—, and $R_7$ is —$OR_6$, then p is 1 to 4;
  d. when M is —O—, then k is 1 to 5;
  e. when W is —O—, then k is 1 to 5;
  f. when $R_7$ is —$OR_6$, then k is 1 to 5;
  g. when W is not a bond with Het bonded through a nitrogen atom, q is 2 to 4, and when W is a bond, q is 0;

or a pharmaceutically acceptable salt thereof, wherein the neoplasm is selected from the group consisting of breast, kidney, bladder, mouth, larynx, esophagus, stomach, colon, ovary, lung, pancreas, liver, prostate, brain, and skin.

30. A method of treating, inhibiting the progression of, or eradicating polycystic kidney disease in a mammal in need thereof which comprises providing to said mammal an effective amount of a compound of Formula (I)

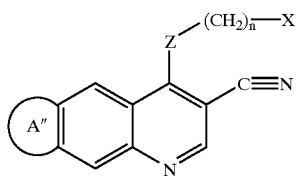

(I)

wherein:
Z is —NH—, —O—, —S(O)$_a$—, or —N—;
R is alkyl of 1 to 6 carbon atoms, or carboalkyl of 2 to 7 carbon atoms;
X is cycloalkyl of 3 to 7 carbon atoms, which may be optionally substituted with one or more alkyl of 1 to 6 carbon atom groups; or
X is pyridinyl, pyrimidinyl, or an aryl ring; wherein the pyridinyl, pyrimidinyl or aryl ring may be optionally mono-, di-, or tri-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

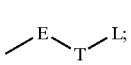

E is pyridinyl, pyrimidinyl, or an aryl ring; wherein the pyridinyl, pyrimidinyl or aryl ring may be optionally mono-, di-, or tri-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at a carbon and is
—NH(CH$_2$)$_m$—, —O(CH$_2$)$_m$—, —S(O)$_a$—(CH$_2$)$_m$—, —NR(CH$_2$)$_m$—, —(CH$_2$)$_m$—; —(CH$_2$)$_m$NH—, —(CH$_2$)$_m$O—, —(CH$_2$)$_m$S(O)$_a$—, or —(CH$_2$)$_m$NR—;

L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylaraino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A" is a moiety selected from the group

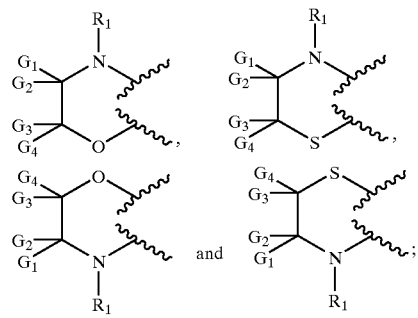

$G_1$, $G_2$, $G_3$ and $G_4$ are independently selected from the group consisting of hydrogen, and alkyl of 1 to 6 carbon atoms;

$R_1$ is —H, $R_{11}$—CH$_2$—, —$R_{12}$,

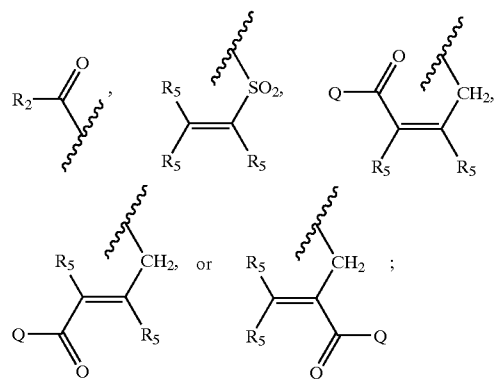

$R_{11}$ is —H, alkyl of 1 to 5 carbon atoms, aryl, or $R_{13}$—(C(R$_6$)$_2$)$_k$—;

$R_{13}$ is

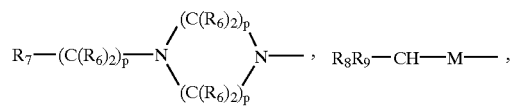

$R_7$—, $R_7$—(C(R$_6$)$_2$)$_p$—M—, or Het-(C(R$_6$)$_2$)$_q$—W—;
$R_7$ is —H, —NR$_6$R$_6$, —OR$_6$, —J, —N(R$_6$)$_3^+$, or —NR$_6$(OR$_6$);

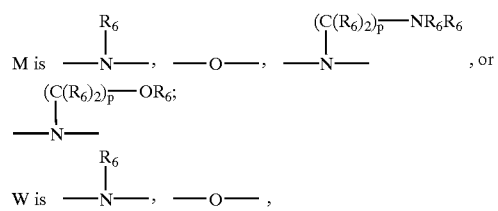

or a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, and tetrahydropyran, optionally mono- or di-substituted on carbon by —$R_6$, hydroxy, —$N(R_6)_2$, —$OR_6$, —$(C(R_6)_2)_s OR_6$, or —$(C(R_6)_2)_s N(R_6)_2$; or optionally mono-substituted on nitrogen with —$R_6$; and optionally mono or di-substituted on a saturated carbon with divalent radicals —O—, or —$O(C(R_6)_2)_s O$—;

$R_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms, $R_7$—$(C(R_6)_2)_{\overline{p}}$—N$\begin{smallmatrix}(C(R_6)_2)_p\\ \\(C(R_6)_2)_p\end{smallmatrix}$N—$(C(R_6)_2)_r$—, $R_7$—$(C(R_6)_2)_s$—, $R_7$—$(C(R_6)_2)_p$—M—$(C(R_6)_2)_r$—, $R_8 R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_r NR_6 R_6$, or —$(C(R_6)_2)_r OR_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;

Q' is alkyl of 1 to 6 carbon atoms;

$R_2$ is selected from the group consisting of $R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;

$R_{3a}$ is $R_7$—$(C(R_6)_2)_{\overline{p}}$—N$\begin{smallmatrix}(C(R_6)_2)_p\\ \\(C(R_6)_2)_p\end{smallmatrix}$N—, $R_7$—, $R_7$—$(C(R_6)_2)_p$—M—, $R_8 R_9$—CH—M—, or Het-$(C(R_6)_2)_q$—W—;

a is 0 to 2;
k is 1,3 to 5;
n is 0 to 1;
m is 0 to 3;
p is 2 to 4;
q is 0 to 4;
r is 1 to 4;
s is 1 to 6;
u is 0 to 4 and v is 0 to 4, wherein the sum of u+v is 2 to 4;

provided that:
a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
b. when $R_3$ is bound to sulfur, $R_3$ is not —H, carboxy, carboalkoxy, or carboalkyl;
c. when M is —O—, and $R_7$ is —$OR_6$, then p is 1 to 4;
d. when M is —O—, then k is 1 to 5;
e. when W is —O—, then k is 1 to 5;
f. when $R_7$ is —$OR_6$, then k is 1 to 5;
g. when W is not a bond with Het bonded through a nitrogen atom, q is 2 to 4, and when W is a bond, q is 0;

or a pharmaceutically acceptable salt thereof.

31. A method of treating, inhibiting, or eradicating colonic polyps in a mammal in need thereof which comprises providing to said mammal an effective amount of a compound of Formula (I)

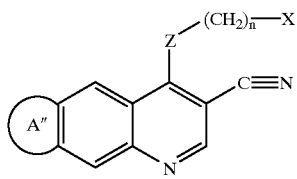

wherein:

Z is —NH—, —O—, —S(O)$_a$—, or —NR—;

R is alkyl of 1 to 6 carbon atoms, or carboalkyl of 2 to 7 carbon atoms;

X is cycloalkyl of 3 to 7 carbon atoms, which may be optionally substituted with one or more alkyl of 1 to 6 carbon atom groups; or X is pyridinyl, pyrimidinyl, or an aryl ring; wherein the pyridinyl, pyrimidinyl or aryl ring may be optionally mono-, di-, or tri-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

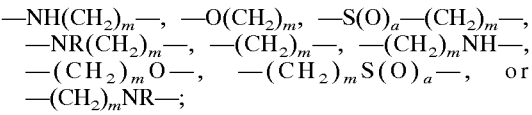

E is pyridinyl, pyrimidinyl, or an aryl ring; wherein the pyridinyl, pyrimidinyl or aryl ring may be optionally mono-, di-, or tri-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at a carbon and is
—NH(CH$_2$)$_m$—, —O(CH$_2$)$_m$, —S(O)$_a$—(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S(O)$_a$—, or —(CH$_2$)$_m$NR—;

L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, 0, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A' is a moiety selected from the group

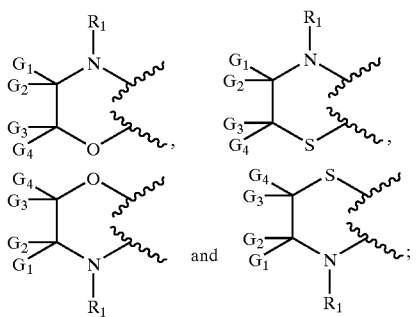

$G_1$, $G_2$, $G_3$ and $G_4$ are independently selected from the group consisting of hydrogen, and alkyl of 1 to 6 carbon atoms;

$R_1$ is —H, $R_{11}$—CH$_2$—, —$R_{12}$,

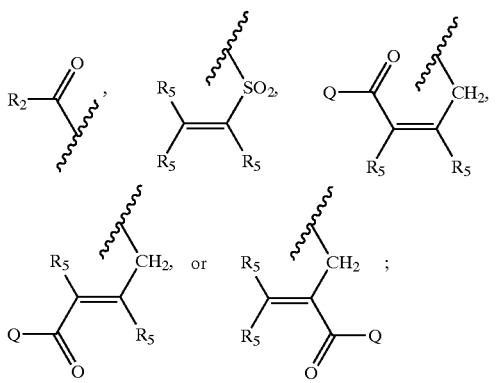

$R_{11}$ is —H, alkyl of 1 to 5 carbon atoms, aryl, or $R_{13}$—(C(R$_6$)$_2$)$_k$—;

$R_{13}$ is

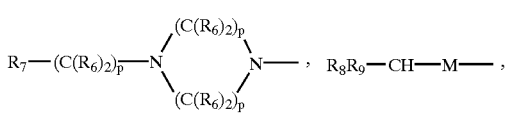

$R_7$—, $R_7$—(C(R$_7$(R$_6$)$_2$)$_p$—M—, or Het-(C(R$_6$)$_2$)$_q$—W—;

$R_7$ is —H, —NR$_6$R$_6$, —OR$_6$, —J, —N(R$_6$)$_3^+$, or —NR$_6$(OR$_6$);

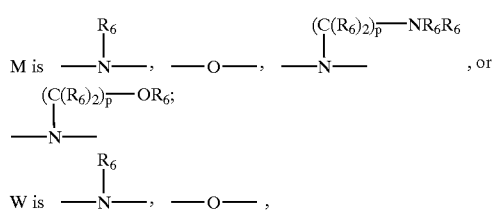

or a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, optionally mono- or di-substituted on carbon by —R$_6$, hydroxy, —N(R$_6$)$_2$, —OR$_6$, —(C(R$_6$)$_2$)$_s$OR$_6$, or —(C(R$_6$)$_2$)$_s$N(R$_6$)$_2$; or optionally mono-substituted on nitrogen with —R$_6$; and optionally mono or di-substituted on a saturated carbon with divalent radicals —O—, or —O(C(R$_6$)$_2$)$_s$O—;

$R_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms,

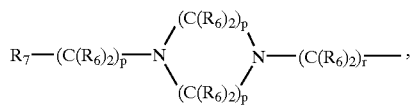

$R_7$—(C(R$_6$)$_2$)$_s$—, $R_7$(C(R$_6$)$_2$)$_p$—M—(C(R$_6$)$_2$)$_r$—, $R_8R_9$—CH—M—(C(R$_6$)$_2$)$_r$—, or Het-(C(R$_6$)$_2$)$_q$—W—(C(R$_6$)$_2$)$_r$—;

$R_8$, and $R_9$ are each, independently, —(C(R$_6$)$_2$)$_r$NR$_6$R$_6$, or —(C(R$_6$)$_2$)$_r$OR$_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;

Q' is alkyl of 1 to 6 carbon atoms;

$R_2$ is selected from the group consisting of

[chemical structures]

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;

$R_{3a}$ is

[chemical structure]

$R_7$—, $R_7$—$(C(R_6)_2)_p$—M—, $R_8R_9$—CH—M—, or Het-$(C(R_6)_2)_q$—W—;

a is 0 to 2;

l is 1,3 to 5;

n is 0 to 1;

m is 0 to 3;

p is 2 to 4;

q is to 4;

r is 1 to 4;

s is 1 to 6;

u is 0 to 4 and v is 0 to 4, wherein the sum of u+v is 2 to 4; provided that:
  a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
  b. when $R_3$ is bound to sulfur, $R_3$ is not —H, carboxy, carboalkoxy, or carboalkyl;
  c. when M is —O—, and $R_7$ is —$OR_6$, then p is 1 to 4;
  d. when M is —O—, then k is 1 to 5;
  e. when W is —O—, then k is 1 to 5;
  f. when $R_7$ is —$OR_6$, then k is 1 to 5;
  g. when W is not a bond with Het bonded through a nitrogen atom, q is 2 to 4, and when W is a bond, q is 0;

or a pharmaceutically acceptable salt thereof.

32. A method of treating or inhibiting the recurrence of stenopsis after corrective surgery on the heart valve in a mammal in need thereof which comprises providing to said mammal an effective amount of a PDGFr kinase inhibitor of Formula (1),

[chemical structure] (I)

wherein:

Z is —NH—, —O—, —$S(O)_a$—, or —NR—;

R is alkyl of 1 to 6 carbon atoms, or carboalkyl of 2 to 7 carbon atoms;

X is cycloalkyl of 3 to 7 carbon atoms, which may be optionally substituted with one or more alkyl of 1 to 6 carbon atom groups; or X is pyridinyl, pyrimidinyl, or an aryl ring; wherein the pyridinyl, pyrimidinyl or aryl ring may be optionally mono-, di-, or tri-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

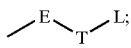

E is pyridinyl, pyrimidinyl, or an aryl ring; wherein the pyridinyl, pyrimidinyl or aryl ring may be optionally mono-, di-, or tri-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at a carbon and is
—NH(CH$_2$)$_m$—, —O(CH$_2$)$_m$—, S(O)$_a$—(CH$_2$)$_a$—, —NR(CH$_2$)$_m$—, —(CH$_2$)$_m$—, —(CH$_2$)$_m$NH—, —(CH$_2$)$_m$O—, —(CH$_2$)$_m$S(O)$_a$—, or —(CH$_2$)$_m$NR—;

L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoakyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A' is a moiety selected from the group

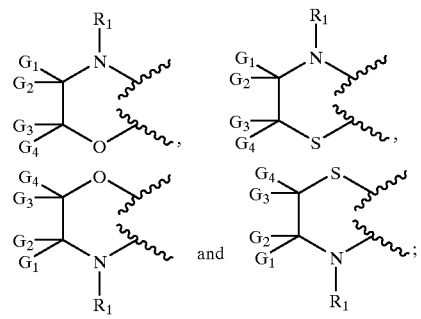

$G_1$, $G_2$, $G_3$ and $G_4$ are independently selected from the group consisting of hydrogen, and alkyl of 1 to 6 carbon atoms;

$R_1$ is —H, $R_{11}$—CH$_2$—, —$R_{12}$,

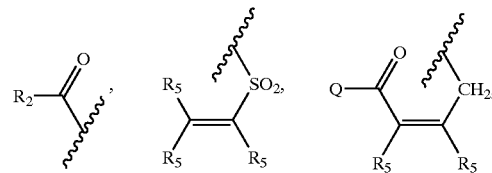

-continued

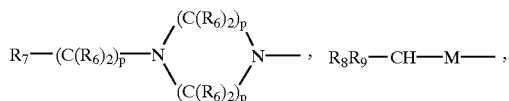

$R_{11}$, is —H, alkyl of 1 to 5 carbon atoms, aryl, or $R_{13}$—$(C(R_6)_2)_k$—;
$R_{13}$ is

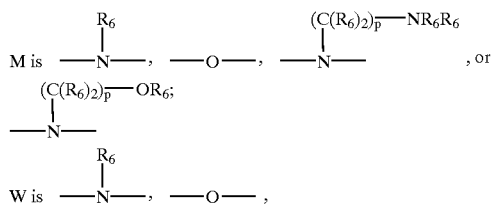

$R_7$—, $R_7$—$(C(R_6)_2)_p$—M—, or Het-$(C(R_6)_2)_q$—W—;
$R_7$ is —H, —$NR_6R_6$, —$OR_6$, —J, —$N(R_6)_3$, or —$NR_6(OR_6)$;

M is $-\overset{R_6}{\underset{|}{N}}-$, —O—, $-\overset{(C(R_6)_2)_{\overline{p}}-NR_6R_6}{\underset{|}{N}}-$, or $-\overset{(C(R_6)_2)_{\overline{p}}-OR_6}{\underset{|}{N}}-$;

W is $-\overset{R_6}{\underset{|}{N}}-$, —O—, or a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, and tetrahydropyran, optionally mono- or di-substituted on carbon by —$R_6$, hydroxy, —$N(R_6)_2$, —$OR_6$, —$(C(R_6)_2)_sOR_6$, or —$(C(R_6)_2)_sN(R_6)_2$; or optionally mono-substituted on nitrogen with —$R_6$; and
optionally mono or di-substituted on a saturated carbon with divalent radicals —O—, or —$O(C(R_6)_2)_sO$—;

$R_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms,

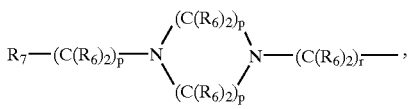

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_r$—$NR_6R_6$, or —$(C(R_6)_2)_r$ $OR_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;

Q' is alkyl of 1 to 6 carbon atoms;

$R_2$ is selected from the group consisting of

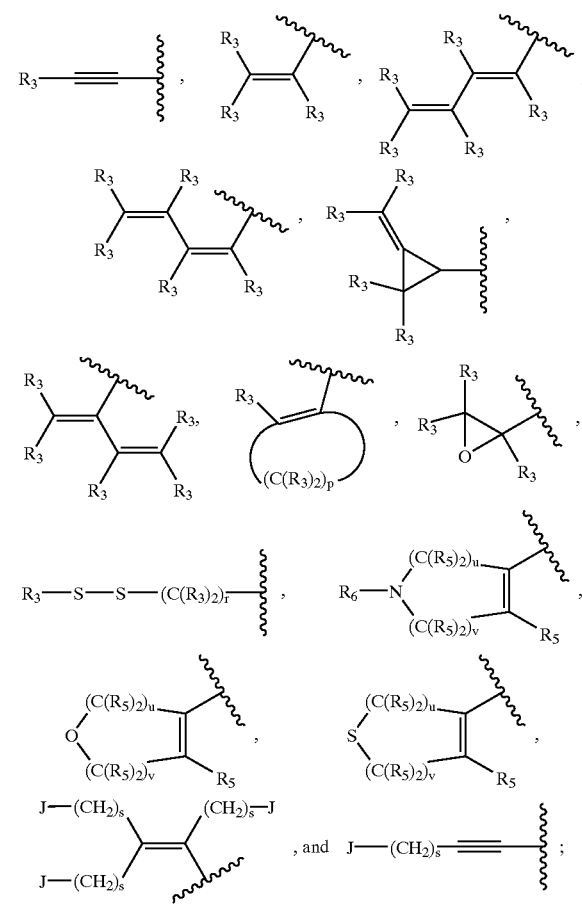

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;

$R_{3a}$ is

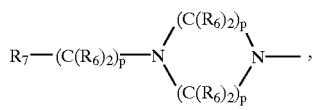

$R_7$—, $R_7$—$(C(R_6)_2)_p$—M—, $R_8R_9$—CH—M—, or Het-$(C(R_6)_2)_q$—W—;

a is 0 to 2;
k is 1, 3 to 5;
n is 0 to 1;
m is 0 to 3;
p is 2 to 4;
q is 0 to 4;
r is 1 to 4;
s is 1 to 6;
u is 0 to 4 and v is 0 to 4, wherein the sum of u+v is 2 to 4; provided that:
  a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
  b. when $R_3$ is bound to sulfur, $R_3$ is not —H, carboxy, carboalkoxy, or carboalkyl;
  c. when M is —O—, and $R_7$ is —$OR_6$, then p is 1 to 4;
  d. when M is —O—, then k is 1 to 5;
  e. when W is —O—, then k is 1 to 5;
  f. when $R_7$ is —$OR_6$, then k is 1 to 5;
  g. when W is not a bond with Het bonded through a nitrogen atom, q is 2 to 4, and when W is a bond, q is 0;
or a pharmaceutically acceptable salt thereof.

33. A method of treating, inhibiting or eradicating rheumatoid arthritis in a mammal in need thereof which comprises providing to said mammal an effective amount of a Zap-70 or Lck kinase inhibitor of Formula (I),

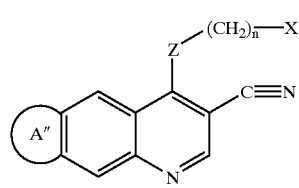

(I)

wherein:
Z is —NH—, —O—, —S(O)$_a$—, or —NR—;
R is alkyl of 1 to 6 carbon atoms, or carboalkyl of 2 to 7 carbon atoms;
X is cycloalkyl of 3 to 7 carbon atoms, which may be optionally substituted with one or more alkyl of 1 to 6 carbon atom groups; or
X is pyridinyl, pyrimidinyl, or an aryl ring; wherein the pyridinyl, pyrimidinyl or aryl ring may be optionally mono-, di-, or tri-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

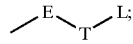

E is pyridinyl, pyrimidinyl, or an aryl ring; wherein the pyridinyl, pyrimidinyl or aryl ring may be optionally mono-, di-, or tri-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N- dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at a carbon and is
—NH(CH$_2$)$_m$—, —O(CH$_2$)$_m$—, —S(O)$_a$—(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S(O)$_a$—, or —(CH$_2$)$_m$NR—;

L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A' is a moiety selected from the group

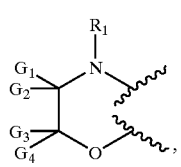 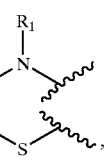

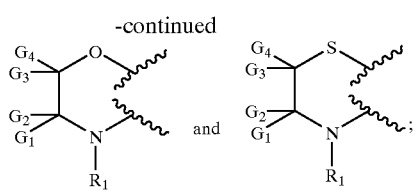

$G_1$, $G_2$, $G_3$ and $G_4$ are independently selected from the group consisting of hydrogen, and alkyl of 1 to 6 carbon atoms;

$R_1$ is —H, $R_{11}$—CH$_2$—, —$R_{12}$,

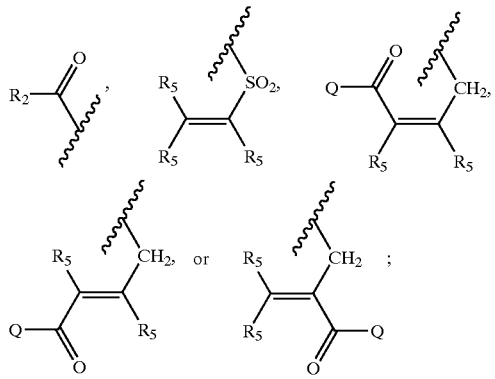

$R_{11}$ is —H, alkyl of 1 to 5 carbon atoms, aryl, or $R_{13}$—(C(R$_6$)$_2$)$_k$—;

$R_{13}$ is

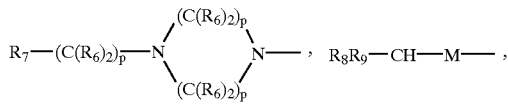

$R_7$—, $R_7$—(C(R$_6$)$_2$)$_p$—M—, or Het-(C(R$_6$)$_2$)$_q$—W—;

$R_7$ is —H, —NR$_6$R$_6$, —OR$_6$, —J, —N(R$_6$)$_3^+$, or —NR$_6$(OR$_6$);

M is

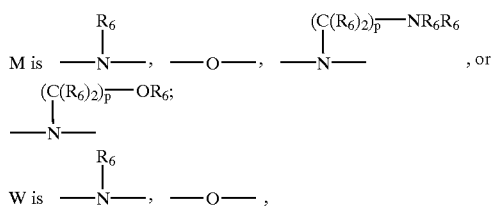

W is —N(R$_6$)—, —O—, or a bond

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, and tetrahydropyran, optionally mono- or di-substituted on carbon by —R$_6$, hydroxy, —N(R$_6$)$_2$, —OR$_6$, —(C(R$_6$)$_2$)$_s$OR$_6$, or —(C(R$_6$)$_2$)$_s$N(R$_6$)$_2$; or optionally mono-substituted on nitrogen with —R$_6$; and optionally mono or di-substituted on a saturated carbon with divalent radicals —O—, or —O(C(R$_6$)$_2$)$_s$O—;

R$_6$ is independently selected from —H, alkyl of 1 to 6 carbon atoms, alkenyl of 2 to 6 carbon atoms, alkynyl of 2 to 6 carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms,

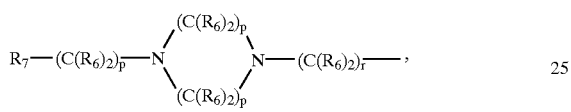

$R_7\text{—}(C(R_6)_2)_s\text{—}$, $R_7\text{—}(C(R_6)_2)_p\text{—}M\text{—}(C(R_6)_2)_r\text{—}$, $R_8R_9\text{—}CH\text{—}M\text{—}(C(R_6)_2)_r\text{—}$, or $Het\text{-}(C(R_6)_2)_q\text{—}W\text{—}(C(R_6)_2)_r\text{—}$;

$R_8$, and $R_9$ are each, independently, $\text{—}(C(R_6)_2)_r NR_6R_6$, or $\text{—}(C(R_6)_2)_r OR_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;

Q' is alkyl of 1 to 6 carbon atoms;

$R_2$ is selected from the group consisting of

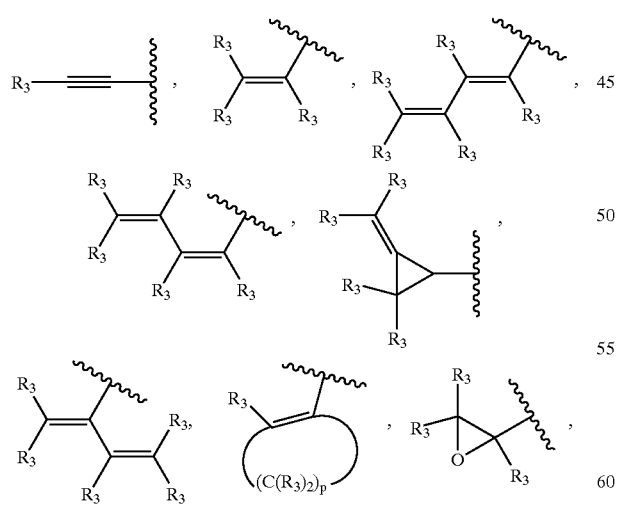

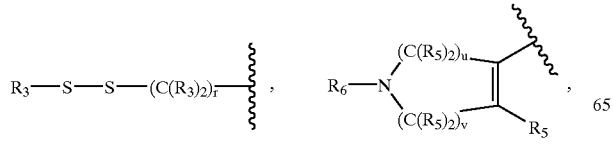

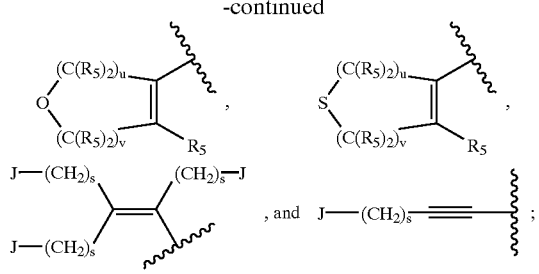

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}\text{—}(C(R_6)_2)_s\text{—}$;

$R_{3a}$ is

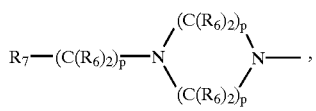

a is 0 to 2;

k is 1, 3 to 5;

n is 0 to 1;

m is 0 to 3;

p is 2 to 4;

q is 0 to 4;

r is 1 to 4;

s is 1 to 6;

u is 0 to 4 and v is 0 to 4, wherein the sum of u+v is 2 to 4;

provided that:
a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
b. when $R_3$ is bound to sulfur, $R_3$ is not —H, carboxy, carboalkoxy, or carboalkyl;
c. when M is —O—, and $R_7$ is —$OR_6$, then p is 1 to 4;
d. when M is —O—, then k is 1 to 5;
e. when W is —O—, then k is 1 to 5;
f. when $R_7$ is —$OR_6$, then k is 1 to 5;
g. when W is not a bond with Het bonded through a nitrogen atom, q is 2 to 4, and when W is a bond, q is 0;

or a pharmaceutically acceptable salt thereof.

34. A method of treating or inhibiting the progression of osteoporosis in a mammal in need thereof which comprises providing to said mammal an effective amount of a Src kinase inhibitor of Formula (I),

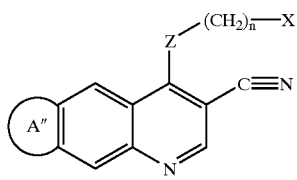

(I)

wherein:

Z is —NH—, —O—, —S(O)$_a$—, or —NR—

R is alkyl of 1 to 6 carbon atoms, or carboalkyl of 2 to 7 carbon atoms;

X is cycloalkyl of 3 to 7 carbon atoms, which may be optionally substituted with one or more alkyl of 1 to 6 carbon atom groups; or X is pyridinyl, pyrimidinyl, or an aryl ring; wherein the pyridinyl, pyrimidinyl or aryl ring may be optionally mono-, di-, or tri-substituted with a substituent independently selected from the group consisiting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent independently selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

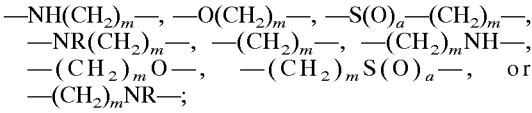

E is pyridinyl, pyrimidinyl, or an aryl ring; wherein the pyridinyl, pyrimidinyl or aryl ring may be optionally mono-, di-, or tri-substituted with a substituent selected from the group consisiting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at a carbon and is
—NH(CH$_2$)$_m$—, —O(CH$_2$)$_m$—, —S(O)$_a$—(CH$_2$)$_m$—, —NR(CH$_2$)$_m$—, —(CH$_2$)$_m$—, —(CH$_2$)$_m$NH—, —(CH$_2$)$_m$O—, —(CH$_2$)$_m$S(O)$_a$—, or —(CH$_2$)$_m$NR—;

L is an aryl ring; that is optionally mono-, di, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy, benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

A" is a moiety selected from the group

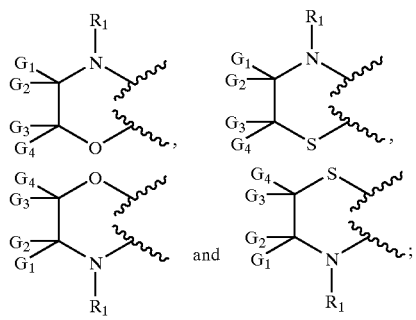

$G_1$, $G_2$, $G_3$ and $G_4$ are independently selected from the group consisting of hydrogen, and alkyl of 1 to 6 carbon atoms;

$R_1$ is —H, $R_{11}$—CH$_2$—, —$R_{12}$,

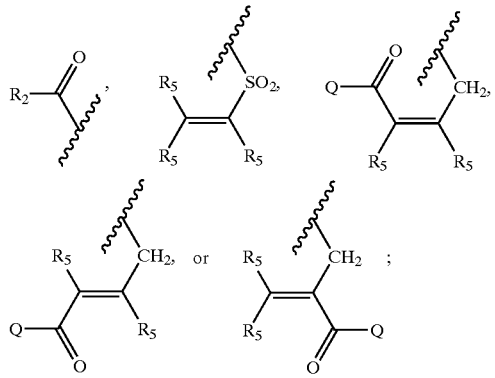

$R_{11}$ is —H, alkyl of 1 to 5 carbon atoms, aryl, or $R_{13}$—(C(R$_6$)$_2$)$_k$—;

$R_{13}$ is

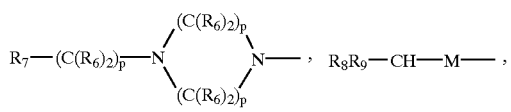

$R_7$—, $R_7$—(C(R$_6$)$_2$)$_p$—M—, or Het-(C(R$_6$)$_2$)$_q$—W—;

$R_7$ is —H, —NR$_6$R$_6$, —OR$_6$, —J, —N(R$_6$)$_3$$^+$, or —NR$_6$(OR$_6$);

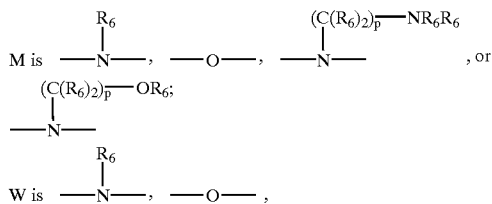

M is

W is or a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, and tetrahydropyran, optionally mono- or di-substituted on carbon by —R$_6$, hydroxy, —N(R$_6$)$_2$, —OR$_6$, —(C(R$_6$)$_2$)$_s$OR$_6$, or —(C(R$_6$)$_2$)$_s$N(R$_6$)$_2$; or optionally mono-substituted on nitrogen with —R$_6$; and optionally mono or di-substituted on a saturated carbon with divalent radicals —O—, or —O(C(R$_6$)$_2$)$_s$O—;

$R_6$ is independently selected from —H, alkyl of 1 to 6 carbon atoms, alkenyl of 2 to 6 carbon atoms, alkynyl of 2- to carbon atoms, cycloalkyl of 3 to 6 carbon atoms, carboalkyl of 2 to 7 carbon atoms, carboxyalkyl of 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms, hydroxy, carboxyl, carboalkoxy of 2 to 7 carbon atoms, phenoxy, phenyl, thiophenoxy, benzoyl, benzyl, phenylamino, benzylamino, alkanoylamino of 1 to 6 carbon atoms, and alkyl of 1 to 6 carbon atoms;

$R_{12}$ is alkylsulphonyl of 1 to 6 carbon atoms, carboalkoxy of 2 to 7 carbon atoms, or carboalkyl of 2 to 7 carbon atoms;

$R_5$ is hydrogen, alkyl of 1 to 6 carbon atoms, carboxy, carboalkoxy of 1 to 6 carbon atoms, aryl, carboalkyl of 2 to 7 carbon atoms,

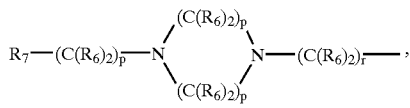

$R_7$—(C(R$_6$)$_2$)$_s$—, $R_7$—(C(R$_6$)$_2$)$_p$—M—(C(R$_6$)$_2$)$_r$—, $R_8$R$_9$—CH—M—(C(R$_6$)$_2$)$_r$—, or Het-(C(R$_6$)$_2$)$_q$—W—(C(R$_6$)$_2$)$_r$—;

$R_8$, and $R_9$ are each, independently, —(C(R$_6$)$_2$)$_r$NR$_6$R$_6$, or —(C(R$_6$)$_2$)$_r$ OR$_6$;

J is independently —H, —F, or —J';

J' is independently chlorine, bromine, iodine, tosylate (p-toluenesulfonate), or mesylate (methanesulfonate);

Q is Q', alkoxy of 1 to 6 carbon atoms, hydroxy, or hydrogen;
Q' is alkyl of 1 to 6 carbon atoms;
$R_2$ is selected from the group consisting of

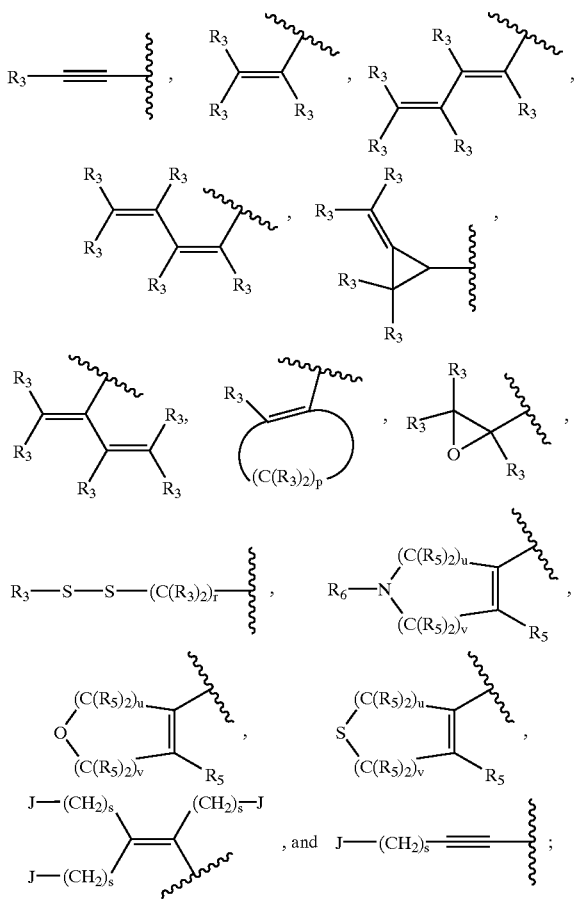

$R_3$ is independently selected from —H, alkyl of 1 to 6 carbon atoms, carboxy, carboalkoxy of 1 to 6 carbon atoms, aryl, carboalkyl of 2 to 7 carbon atoms, and $R_{3a}$—$(C(R_6)_2)_s$—;
$R_{3a}$ is

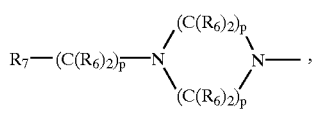

$R_7$—, $R_7$—$(C(R_6)_2)_p$—M—, $R_8R_9$—CH—M—, or Het-$(C(R_6)_2)_q$—W—;
a is 0 to 2;
k is 1, 3 to 5;
n is 0 to 1;
m is 0 to 3;
p is 2 to 4;
q is 0 to 4;
r is 1 to 4;
s is 1 to 6;
u is 0 to 4 and v is 0 to 4, wherein the sum of u+v is 2 to 4;
provided that:
  a. when —$R_6$ is alkenyl of 2 to 7 carbon atoms or alkynyl of 2 to 7 carbon atoms, said alkenyl of 2 to 7 carbon atoms or alkynyl of 2 to 7 carbon atoms is bound to a nitrogen or oxygen atom through a saturated carbon atom;
  b. when $R_3$ is bound to sulfur, $R_3$ is not —H, carboxy, carboalkoxy, or carboalkyl;
  c. when M is —O—, and $R_7$ is —$OR_6$, then p is 1 to 4;
  d. when M is —O—, then k is 1 to 5;
  e. when W is —O—, then k is 1 to 5;
  f. when $R_7$ is —$OR_6$, then k is 1 to 5;
  g. when W is not a bond with Het bonded through a nitrogen atom, q is 2 to 4, and when W is a bond, q is 0;
or a pharmaceutically acceptable salt thereof.

35. The method according to claim 29 wherein the neoplasm expresses EGFR or erbB2(Her2).

36. The method according to claim 29 wherein the neoplasm depends, on the MAPK pathway.

37. The method of claim 29 wherein the neoplasm depends, on the ECK/LERK-1 pathway.

38. The method according to claim 29 wherein the neoplasm depends, on the VEGF/KDR pathway.

39. The method of claim 29 wherein the neoplasm expresses Src or wherein the neoplasm depends on the Src pathway.

40. The method of claim 29 wherein the neoplasm expresses raf or wherein the neoplasm depends on the raf pathway.

41. The method of claim 29 wherein the neoplasm expresses EGFr, erbB-2, erbB-3 or erbB-4 or wherein the neoplasm depends on the EGFr, erbB-2, erbB-3 or erbB-4 pathway.

42. The method of claim 29 wherein the neoplasm expresses KDR or flt-1 or wherein the neoplasm depends on the KDR or flt-1 pathway.

43. The method of claim 29 wherein the neoplasm expresses PDGFr or wherein the neoplasm depends on the PDGFr pathway.

44. The method of claim 29 wherein the neoplasm expresses FGFr or wherein the neoplasm depends on the FGFr pathway.

45. The method of claim 29 wherein the neoplasm expresses tie-1 or tie-2 or wherein the neoplasm depends on the tie-1 or tie-2 pathway.

46. The method of claim 29 wherein the neoplasm expresses EPH or wherein the neoplasm depends on the EPH pathway.

47. The method of claim 29 wherein the neoplasm expresses a non-receptor tyrosine kinase including Abl, Jak, Fak, Syk or Csk or wherein the neoplasm depends on the Abl, Jak, Fak, Syk or Csk pathway.

48. The method of claim 29 wherein the neoplasm expresses mek or erk or wherein the neoplasm depends on the MAPK pathway.

49. The method of claim 29 wherein the neoplasm expresses a cyclin dependent kinase or wherein the neoplasm depends on a cyclin dependent kinase pathway.

50. The method of claim 29 wherein the neoplasm expresses a Src family kinase including Yes, Lck or Lyn or wherein the neoplasm depends on a Src family kinase pathway.

51. The method of claim 29 wherein the neoplasm expresses PKA, PKB or PKC or wherein the neoplasm depends on a PKA, PKB or PKC pathway.

* * * * *